(12) United States Patent
Thomas

(10) Patent No.: US 8,877,502 B2
(45) Date of Patent: Nov. 4, 2014

(54) PLASMID CURING

(75) Inventor: Christopher Morton Thomas, Birmingham (GB)

(73) Assignee: The University of Birmingham (GB)

( * ) Notice: Subject to any disclaimer, the term of this patent is extended or adjusted under 35 U.S.C. 154(b) by 684 days.

(21) Appl. No.: 12/299,843

(22) PCT Filed: May 9, 2007

(86) PCT No.: PCT/GB2007/001682
§ 371 (c)(1),
(2), (4) Date: Mar. 18, 2009

(87) PCT Pub. No.: WO2007/129087
PCT Pub. Date: Nov. 15, 2007

(65) Prior Publication Data
US 2010/0003738 A1    Jan. 7, 2010

(30) Foreign Application Priority Data

May 9, 2006    (GB) .................................. 0609124.3

(51) Int. Cl.
| | | |
|---|---|---|
| C12N 15/00 | (2006.01) | |
| C12N 15/63 | (2006.01) | |
| C12N 1/20 | (2006.01) | |
| C12N 15/74 | (2006.01) | |
| C07H 21/00 | (2006.01) | |
| C07H 21/02 | (2006.01) | |
| C07H 21/04 | (2006.01) | |
| C07H 19/06 | (2006.01) | |
| C07H 19/067 | (2006.01) | |
| C07H 19/073 | (2006.01) | |
| C07H 19/16 | (2006.01) | |
| C07H 19/167 | (2006.01) | |
| C07H 19/173 | (2006.01) | |

(52) U.S. Cl.
CPC ...................................... *C12N 15/63* (2013.01)

USPC ................... 435/455; 435/252.3; 435/252.31; 435/320.1; 435/476; 435/480; 536/22.1; 536/23.1; 536/23.2; 536/24.1; 536/24.2

(58) Field of Classification Search
None
See application file for complete search history.

(56) References Cited

U.S. PATENT DOCUMENTS

2006/0172398 A1 *    8/2006   Nomoto et al. ............... 435/135

OTHER PUBLICATIONS

Uraji et al (Genes Genetic System. 2002. vol. 77, pp. 1-9).*
Tatsuno et al (Infection and Immunity, 2001. vol. 69, No. 11, pp. 6660-6669).*
Lehnherr and Yarmolinsky (PNAS, 1995. vol. 92, pp. 3274-3277).*
Gottesman et al., JBC, 1993, vol. 268, No. 30, pp. 22618-22626.*
Bingle et al., "Regulatory circuits for plasmid survival" 4 Current Opinion in Microbiology 191-200 (2001).*

* cited by examiner

*Primary Examiner* — Celine Qian
*Assistant Examiner* — Nancy J Leith
(74) *Attorney, Agent, or Firm* — Berliner & Associates

(57) ABSTRACT

The present invention relates to plasmid curing, and particularly to efficient and stress-free methods for displacing resident or endogenous plasmids from a host cell, such as a bacterium. The invention extends to method of displacing a plasmid comprising a post-segregational killing system from a host cell, the method comprising introducing a recombinant nucleic acid molecule into a host cell harboring a plasmid comprising a post-segregational killing (PSK) system, characterized in that the recombinant nucleic acid molecule is adapted to neutralize the toxic effects of the plasmid's post-segregational killing system, and wherein the nucleic acid molecule is also adapted to outcompete or inhibit replication of the plasmid. The invention further extends to recombinant nucleic acid molecules that can be used in this method, as well as further uses of the methods and nucleic acid molecules of the invention.

2 Claims, 7 Drawing Sheets

Figure:1
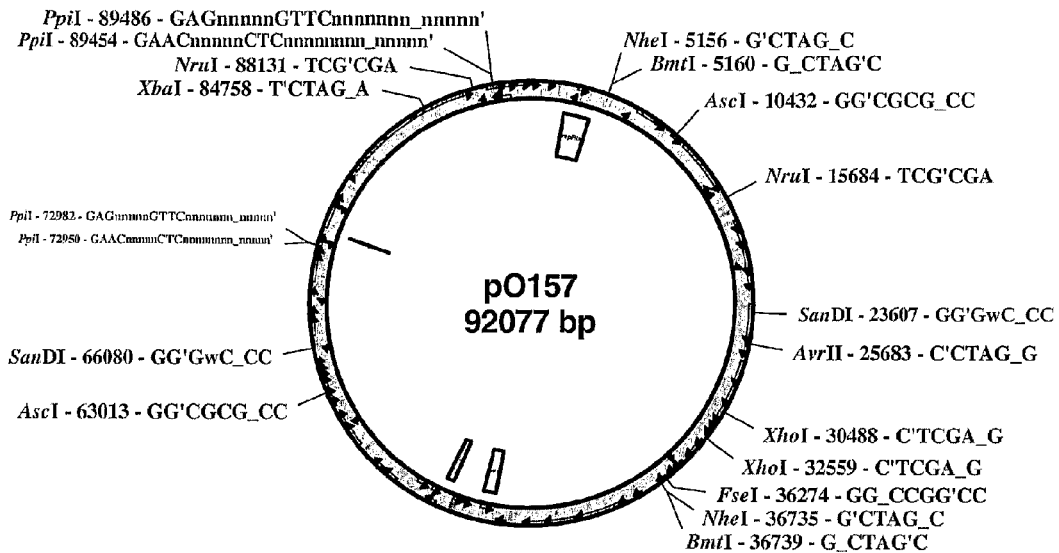
Figure:2
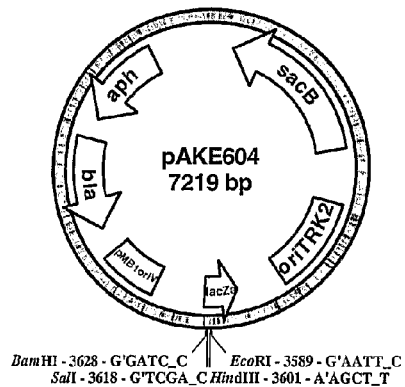

Figure:3: part 1
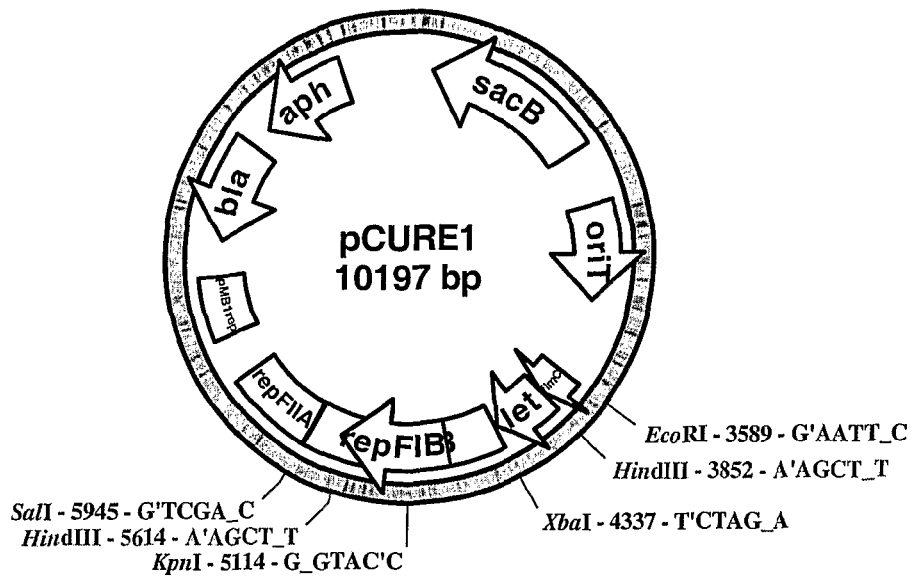
Figure:3: part 2
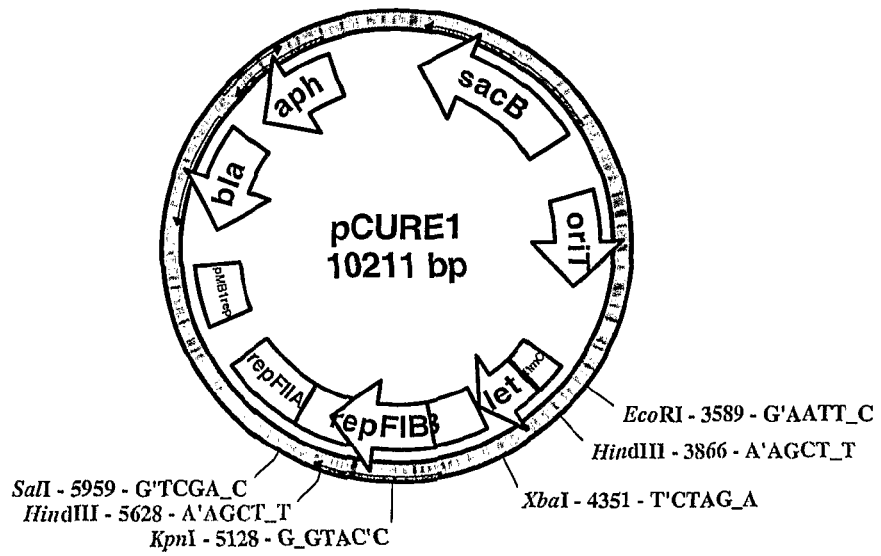

Figure: 4: part 1
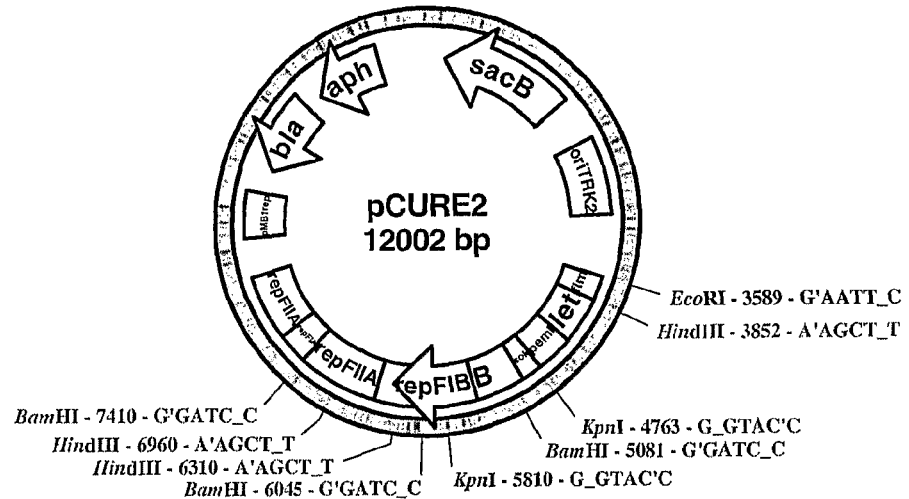
Figure: 4: part 2
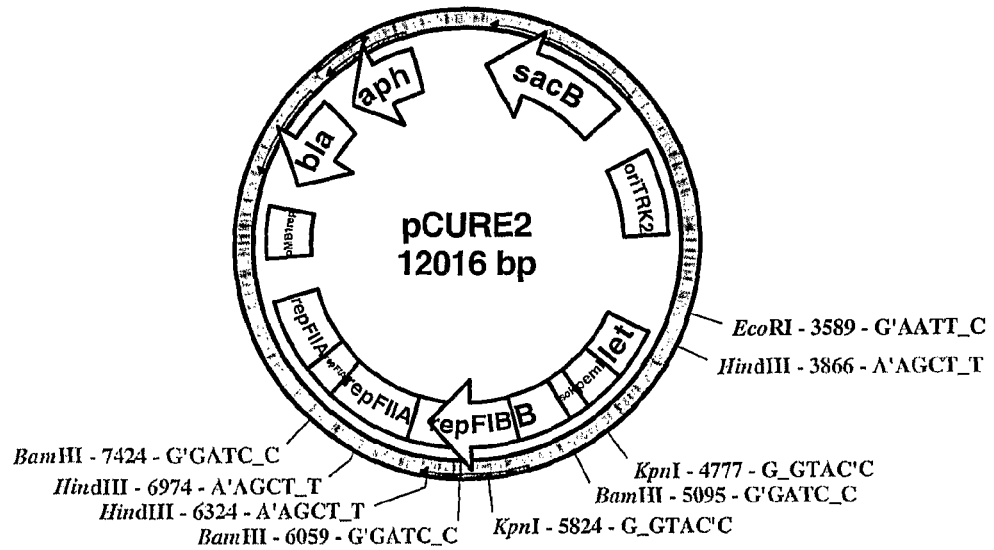

Figure: 5
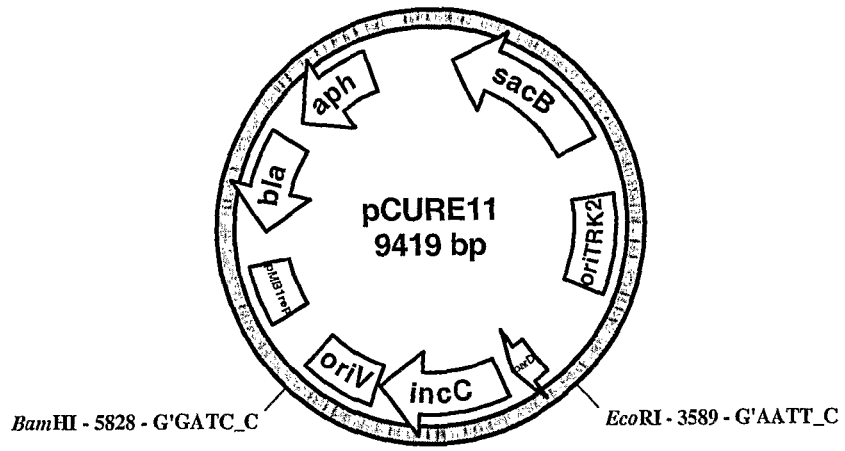
Figure: 6
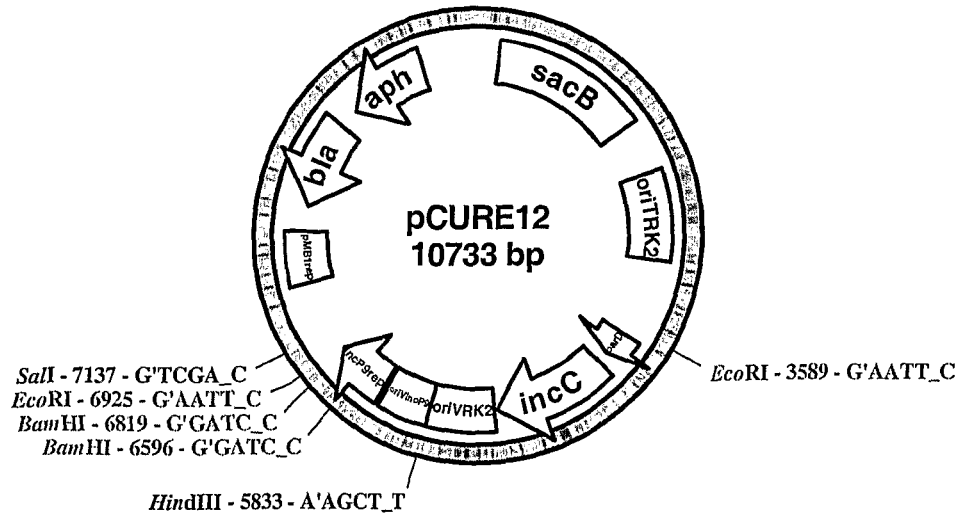

Figure:7
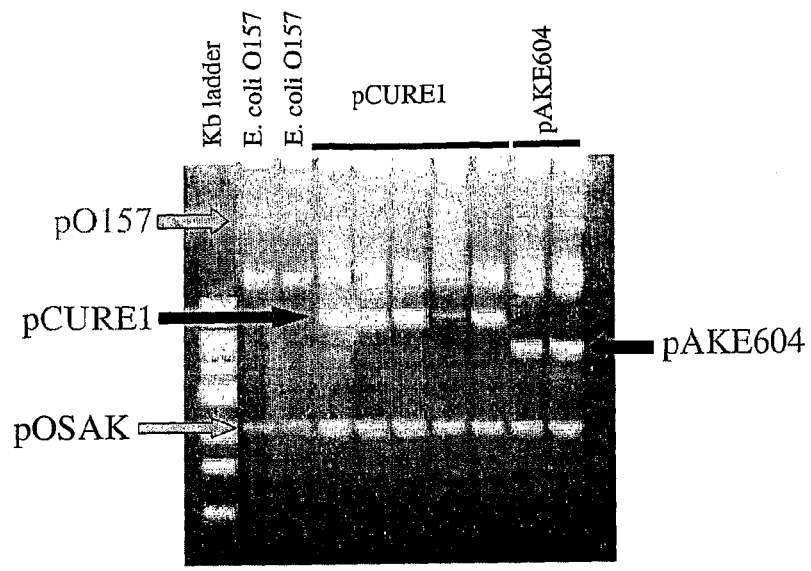
Figure:8
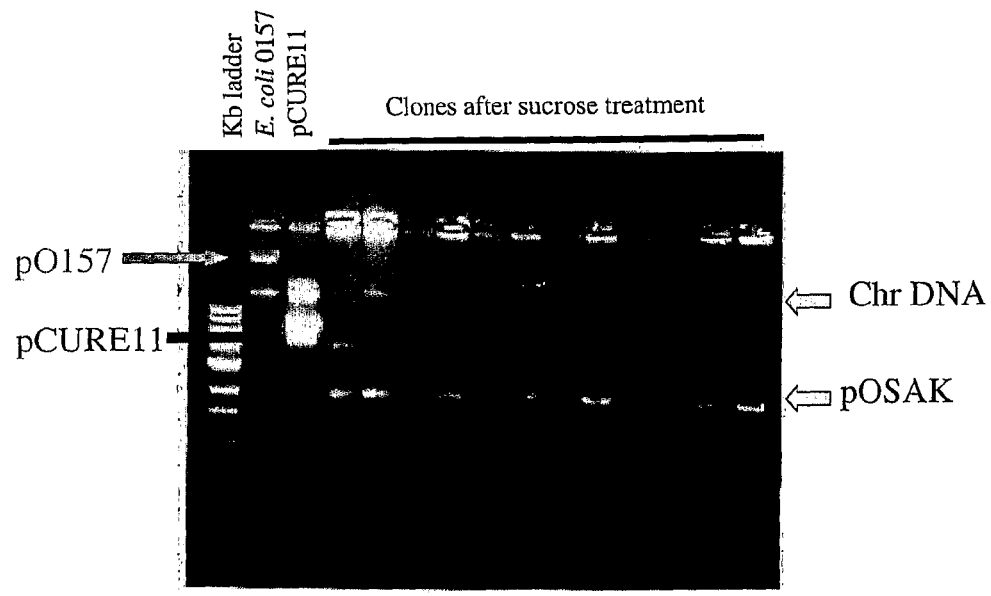

Figure:9
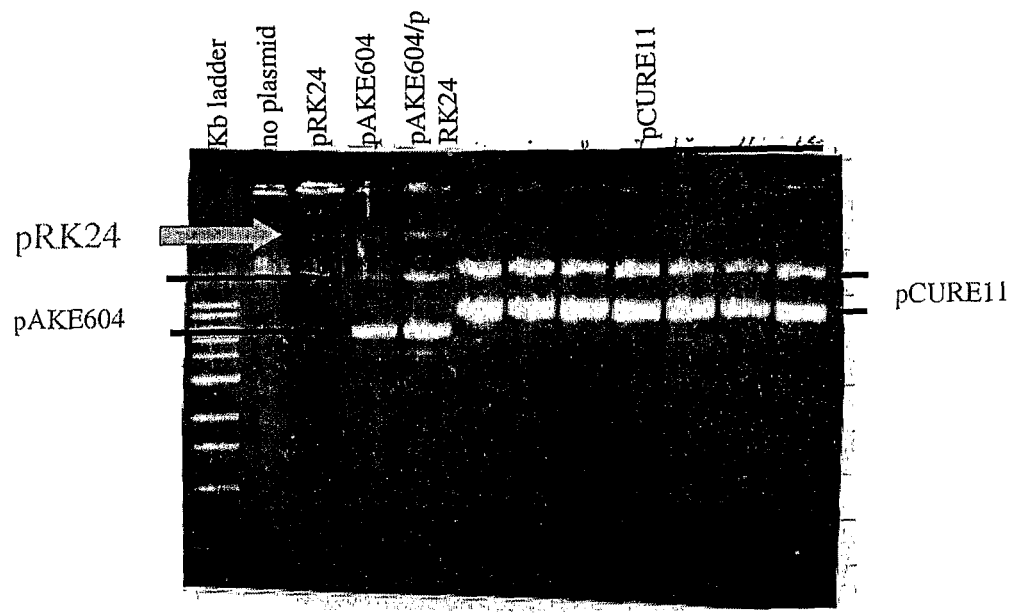
Figure:10
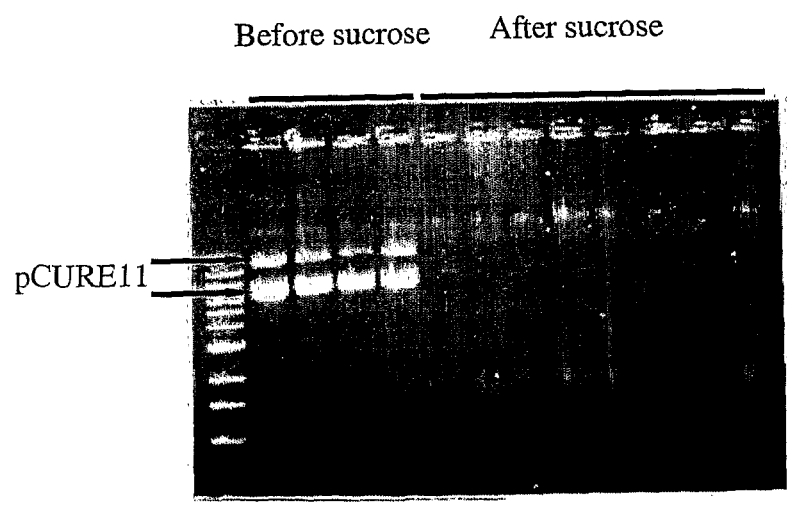

Figure:11
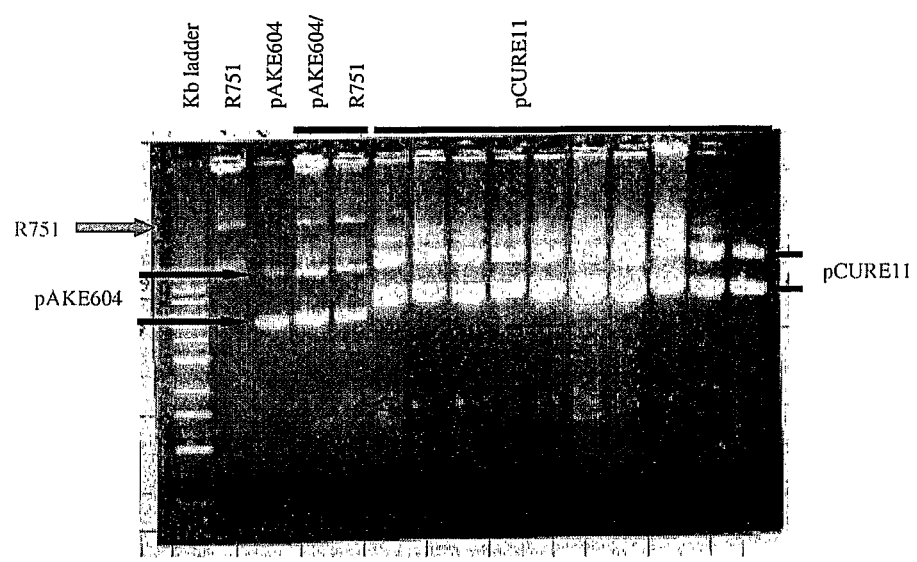

SEQUENCE LISTING

```
<160> NUMBER OF SEQ ID NOS: 33

<210> SEQ ID NO 1
<211> LENGTH: 7219
<212> TYPE: DNA
<213> ORGANISM: Artificial
<220> FEATURE:
<223> OTHER INFORMATION: Plasmid vector

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataatcg gcattttctt ttgcgttttt atttgttaac tgttaattgt ccttgttcaa     240
ggatgctgtc tttgacaaca gatgttttct tgcctttgat gttcagcagg aagctaggcg     300
caaacgttga ttgtttgtct gcgtagaatc ctctgtttgt catatagctt gtaatcacga     360
cattgtttcc tttcgcttga ggtacagcga agtgtgagta agtaaaggtt acatcgttag     420
gatcaagatc cattttaac acaaggccag ttttgttcag cggcttgtat gggccagtta     480
aagaattaga aacataacca agcatgtaaa tatcgttaga cgtaatgccg tcaatcgtca     540 ttttgatcc gcgggagtca gtgaacagat accatttgcc gttcatttta aagacgttcg     600
cgcgttcaat ttcatctgtt actgtgttag atgcaatcag cggtttcatc acttttttca     660
gtgtgtaatc atcgtttagc tcaatcatac cgagagcgcc gtttgctaac tcagccgtgc     720
```

```
gtttttatc gctttgcaga agttttgac tttcttgacg gaagaatgat gtgcttttgc      780
catagtatgc tttgttaaat aaagattctt cgccttggta gccatcttca gttccagtgt    840
ttgcttcaaa tactaagtat ttgtggcctt tatcttctac gtagtgagga tctctcagcg    900
tatggttgtc gcctgagctg tagttgcctt catcgatgaa ctgctgtaca ttttgatacg    960 ttttccgtc accgtcaaag attgatttat aatcctctac accgttgatg ttcaaagagc    1020
tgtctgatgc tgatacgtta acttgtgcag ttgtcagtgt ttgtttgccg taatgtttac    1080
cggagaaatc agtgtagaat aaacggattt ttccgtcaga tgtaaatgtg gctgaacctg    1140
accattcttg tgtttggtct tttaggatag aatcatttgc atcgaatttg tcgctgtctt    1200
taaagacgcg gccagcgttt ttccagctgt caatagaagt ttcgccgact ttttgataga    1260
acatgtaaat cgatgtgtca tccgcatttt taggatctcc ggctaatgca aagacgatgt    1320
ggtagccgtg atagtttgcg acagtgccgt cagcgttttg taatggccag ctgtcccaaa    1380
cgtccaggcc ttttgcagaa agatatttt taattgtgga cgaatcgaac tcaggaactt    1440 gatattttc attttttgc tgttcaggga tttgcagcat atcatggcgt gtaatatggg     1500
aaatgccgta tgtttcctta tatggctttt ggttcgtttc tttcgcaaac gcttgagttg    1560
cgcctcctgc cagcagtgcg gtagtaaagg ttaatactgt tgcttgtttt gcaaactttt    1620
tgatgttcat cgttcatgtc tcctttttta tgtactgtgt tagcggtctg cttcttccag    1680
ccctcctgtt tgaagatggc aagttagtta cgcacaataa aaaagacct aaaatatgta     1740 agggtgacg ccaaagtata cactttgccc tttacacatt ttaggtcttg cctgctttat     1800
cagtaacaaa cccgcgcgat ttacttttcg acctcattct attagactct cgtttggatt    1860
gcaactggtc tattttcctc ttttgtttga tagaaaatca taaaaggatt tgcagactac    1920
gggcctaaag aactaaaaaa tctatctgtt tcttttcatt ctctgtattt tttatagttt    1980
ctgttgcatg gcataaagt tgccttttta atcacaattc agaaaatatc ataatatctc     2040
atttcactaa ataatagtga acggcaggta tatgtgatgg gttaaaaagg atcgatcctc    2100
tagctagagt cgatcttcgc cagcagggcg aggatcgtgg catcaccgaa ccgcgccgtg    2160
cgcgggtcgt cggtgagcca gagtttcagc aggccgccca ggcggcccag gtcgccattg    2220
atgcgggcca gctcgcggac gtgctcatag tccacgacgc ccgtgatttt gtagccctgg    2280
ccgacggcca gcaggtaggc cgacaggctc atgccgcccg ccgccgcctt ttcctcaatc    2340
gctcttcgtt cgtctggaag gcagtacacc ttgataggtg ggctgccctt cctggttggc    2400
ttggtttcat cagccatccg cttgccctca tctgttacgc cggcggtagc cggccagcct    2460
cgcagagcag gattcccgtt gagcaccgcc aggtgcgaat aagggacagt gaagaaggaa    2520
cacccgctcg cgggtgggcc tacttcacct atcctgcccg gctgacgccg ttggatacac    2580
caaggaaagt ctacacgaac cctttggcaa atcctgtat atcgtgcgaa aaaggatgga    2640
tataccgaaa aaatcgctat aatgaccccg aagcagggtt atgcagcgga aaagcgctgc    2700
ttccctgctg ttttgtggaa tatctaccga ctggaaacag gcaaatgcag gaaattactg    2760
aactgagggg acaggcgaga gacgatgcca aagagctaca ccgacgagct ggccgagtgg    2820
gttgaatccc gcgcggccaa gaagcgccgg cgtgatgagg ctgcggttgc gttcctggcg    2880
gtgagggcgg atgtcgatat gcgtaaggag aaaataccgc atcaggcgca tgcatatttg    2940
aatgtattta gaaaaataaa caaaagagt ttgtagaaac gcaaaaggc catccgtcag     3000 gatgccttc tgcttaattt gatgcctggc agttatggc gggcgtcctg cccgccaccc      3060
tccgggccgt tgcttcgcaa cgttcaaatc cgctcccggc ggatttgtcc tactcaggag    3120
```

```
agcgttcacc gacaaacaac agataaaacg aaaggcccag tctttcgact gagcctttcg    3180
ttttatttga tgcctggcag ttccctactc tcgcatgggg agaccccaca ctaccatcgg    3240
cgctacggcg tttcacttct gagttcggca tggggtcagg tgggaccacc gcgctactgc    3300
cgccaggcaa attctgtttt atcagaccgc ttctgcgttc tgatttaatc tgtatcaggc    3360
tgaaaatctt ctctcatccg ccaaaacagc caagctcgcc attcgccatt caggctgcgc    3420
aactgttggg aagggcgatc ggtgcgggcc tcttcgctat tacgccagct ggcgaaaggg    3480
ggatgtgctg caaggcgatt aagttgggta acgccagggt tttcccagtc acgacgttgt    3540
aaaacgacgg ccagtgccaa gctcattacc ctgttatccc tacccggtga attctctaga    3600
aagcttctgc agccatggtc gacccgggga tccgggatta ccctgttatc cctagagctt    3660
ggcgtaatca tggtcatagc tgtttcctgt gtgaaattgt tatccgctca caattccaca    3720
caacatacga gccggaagca taaagtgtaa agcctggggt gcctaatgag tgagctaact    3780
cacattaatt gcgttgcgct cactgcccgc tttccagtcg ggaaacctgt cgtgccagct    3840
gcattaatga atcggccaac gcgcgggag aggcggtttg cgtattgggc gctcttccgc     3900
ttcctcgctc actgactcgc tgcgctcggt cgttcggctg cggcgagcgg tatcagctca    3960
ctcaaaggcg gtaatacggt tatccacaga atcaggggat aacgcaggaa agaacatgtg    4020
agcaaaaggc cagcaaaagg ccaggaaccg taaaaaggcc gcgttgctgg cgttttttcca   4080 taggctccgc cccctgacg agcatcacaa aaatcgacgc tcaagtcaga ggtggcgaaa     4140
cccgacagga ctataaagat accaggcgtt tccccctgga agctccctcg tgcgctctcc    4200
tgttccgacc ctgccgctta ccggatacct gtccgccttt ctcccttcgg gaagcgtggc    4260
gctttctcat agctcacgct gtaggtatct cagttcggtg taggtcgttc gctccaagct    4320
gggctgtgtg cacgaacccc ccgttcagcc cgaccgctgc gccttatccg gtaactatcg    4380
tcttgagtcc aacccggtaa gacacgactt atcgccactg gcagcagcca ctggtaacag    4440
gattagcaga gcgaggtatg taggcggtgc tacagagttc ttgaagtggt ggcctaacta    4500
cggctacact agaaggacag tatttggtat ctgcgctctg ctgaagccag ttaccttcgg    4560
aaaaagagtt ggtagctctt gatccggcaa acaaaccacc gctggtagcg gtggtttttt    4620
tgtttgcaag cagcagatta cgcgcagaaa aaaaggatct caagaagatc ctttgatctt    4680
ttctacgggg tctgacgctc agtggaacga aaactcacgt taagggattt tggtcatgag    4740
attatcaaaa aggatcttca cctagatcct tttaaattaa aaatgaagtt ttaaatcaat    4800
ctaaagtata tatgagtaaa cttggtctga cagttaccaa tgcttaatca gtgaggcacc    4860
tatctcagcg atctgtctat ttcgttcatc catagttgcc tgactccccg tcgtgtagat    4920
aactacgata cgggagggct taccatctgg ccccagtgct gcaatgatac cgcgagaccc    4980
acgctcaccg gctccagatt tatcagcaat aaaccagcca gccggaaggg ccgagcgcag    5040
aagtggtcct gcaactttat ccgcctccat ccagtctatt aattgttgcc gggaagctag    5100
agtaagtagt tcgccagtta atagtttgcg caacgttgtt gccattgcta caggcatcgt    5160
ggtgtcacgc tcgtcgtttg gtatggcttc attcagctcc ggttcccaac gatcaaggcg    5220
agttacatga tcccccatgt tgtgcaaaaa agcggttagc tccttcggtc ctccgatcgt    5280
tgtcagaagt aagttggccg cagtgttatc actcatggtt atggcagcac tgcataattc    5340
tcttactgtc atgccatccg taagatgctt ttctgtgact ggtgagtact caaccaagtc    5400
attctgagaa tagtgtatgc ggcgaccgag ttgctcttgc ccggcgtcaa tacgggataa    5460
taccgcgcca catagcagaa ctttaaaagt gctcatcatt ggaaaacgtt cttcggggcg    5520
```

```
aaaactctca aggatcttac cgctgttgag atccagttcg atgtaaccca ctcgtgcacc      5580
caactgatct tcagcatctt ttactttcac cagcgtttct gggtgagcaa aaacaggaag      5640
gcaaaatgcc gcaaaaaagg gaataagggc gacacggaaa tgttgaatac tcatactctt      5700
cctttttcaa tggggtgggc gaagaactcc agcatgagat cccgcgctg gaggatcatc       5760
cagccggcgt cccggaaaac gattccgaag cccaaccttt catagaaggc ggcggtggaa      5820
tcgaaatctc gtgatggcag gttgggcgtc gcttggtcgg tcatttcgaa ccccagagtc      5880
ccgctcagaa gaactcgtca agaaggcgat agaaggcgat gcgctgcgaa tcgggagcgg      5940
cgataccgta aagcacgagg aagcggtcag cccattcgcc gccaagctct tcagcaatat      6000
cacgggtagc caacgctatg tcctgatagc ggtccgccac acccagccgg ccacagtcga      6060
tgaatccaga aaagcggcca ttttccacca tgatattcgg caagcaggca tcgccatggg      6120
tcacgacgag atcctcgccg tcgggcatgc gcgccttgag cctggcgaac agttcggctg      6180
gcgcgagccc ctgatgctct tcgtccagat catcctgatc gacaagaccg gcttccatcc      6240
gagtacgtgc tcgctcgatg cgatgtttcg cttggtggtc gaatgggcag gtagccggat      6300
caagcgtatg cagccgccgc attgcatcag ccatgatgga tactttctcg gcaggagcaa      6360
ggtgagatga caggagatcc tgccccggca cttcgcccaa tagcagccag tcccttcccg      6420
cttcagtgac aacgtcgagc acagctgcgc aaggaacgcc cgtcgtggcc agccacgata      6480
gccgcgctgc ctcgtcctgc agttcattca gggcaccgga caggtcggtc ttgacaaaaa      6540
gaaccgggcg cccctgcgct gacagccgga acacggcggc atcagagcag ccgattgtct      6600
gttgtgccca gtcatagccg aatagcctct ccacccaagc ggccggagaa cctgcgtgca      6660
atccatcttg ttcaatcatg cgaaacgatc ctcatcctgt ctcttgatca gatcttgatc      6720
ccctgcgcca tcagatcctt ggcggcaaga agccatcca gtttactttg cagggcttcc       6780
caaccttacc agagggcgcc ccagctggca attccggttc gcttgctgtc cataaaaccg      6840
cccagtctag ctatcgccat gtaagcccac tgcaagctac ctgctttctc tttgcgcttg      6900
cgttttccct tgtccagata gcccagtagc tgacattcat ccggggtcag caccgtttct      6960
gcggactggc tttctacgtg ttccgcttcc tttagcagcc cttgcgccct gagtgcttgc      7020
ggcagcgtga agctattatt gaagcattta tcagggttat tgtctcatga gcggatacat      7080
atttgaatgt atttagaaaa ataaacaaat aggggttccg cgcacatttc cccgaaaagt      7140
gccacctgac gtctaagaaa ccattattat catgacatta acctataaaa ataggcgtat      7200
cacgaggcgc cttttcgtc                                                   7219

<210> SEQ ID NO 2
<211> LENGTH: 10197
<212> TYPE: DNA
<213> ORGANISM: Artificial
<220> FEATURE:
<223> OTHER INFORMATION: Derivative of vector pAKE604

<400> SEQUENCE: 2
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accataatcg gcattttctt ttgcgttttt atttgttaac tgttaattgt ccttgttcaa       240
ggatgctgtc tttgacaaca gatgttttct tgcctttgat gttcagcagg aagctaggcg       300
caaacgttga ttgtttgtct gcgtagaatc ctctgtttgt catatagctt gtaatcacga       360
```

| | |
|---|---|
| cattgtttcc tttcgcttga ggtacagcga agtgtgagta agtaaaggtt acatcgttag | 420 |
| gatcaagatc catttttaac acaaggccag ttttgttcag cggcttgtat gggccagtta | 480 |
| aagaattaga aacataacca agcatgtaaa tatcgttaga cgtaatgccg tcaatcgtca | 540 |
| tttttgatcc gcgggagtca gtgaacagat accatttgcc gttcatttta aagacgttcg | 600 |
| cgcgttcaat ttcatctgtt actgtgttag atgcaatcag cggtttcatc acttttttca | 660 |
| gtgtgtaatc atcgtttagc tcaatcatac cgagagcgcc gtttgctaac tcagccgtgc | 720 |
| gttttttatc gctttgcaga agttttttgac tttcttgacg gaagaatgat gtgcttttgc | 780 |
| catagtatgc tttgttaaat aaagattctt cgccttggta gccatcttca gttccagtgt | 840 |
| ttgcttcaaa tactaagtat ttgtggcctt tatcttctac gtagtgagga tctctcagcg | 900 |
| tatggttgtc gcctgagctg tagttgcctt catcgatgaa ctgctgtaca ttttgatacg | 960 |
| ttttttccgtc accgtcaaag attgatttat aatcctctac accgttgatg ttcaaagagc | 1020 |
| tgtctgatgc tgatacgtta acttgtgcag ttgtcagtgt ttgtttgccg taatgtttac | 1080 |
| cggagaaatc agtgtagaat aaacggattt ttccgtcaga tgtaaatgtg gctgaacctg | 1140 |
| accattcttg tgtttggtct tttaggatag aatcatttgc atcgaatttg tcgctgtctt | 1200 |
| taaagacgcg gccagcgttt ttccagctgt caatagaagt ttcgccgact ttttgataga | 1260 |
| acatgtaaat cgatgtgtca tccgcatttt taggatctcc ggctaatgca aagacgatgt | 1320 |
| ggtagccgtg atagtttgcg acagtgccgt cagcgttttg taatggccag ctgtcccaaa | 1380 |
| cgtccaggcc ttttgcagaa gagatatttt taattgtgga cgaatcgaac tcaggaactt | 1440 |
| gatatttttc atttttttgc tgttcaggga tttgcagcat atcatggcgt gtaatatggg | 1500 |
| aaatgccgta tgtttcctta tatggctttt ggttcgtttc tttcgcaaac gcttgagttg | 1560 |
| cgcctcctgc cagcagtgcg gtagtaaagg ttaatactgt tgcttgtttt gcaaactttt | 1620 |
| tgatgttcat cgttcatgtc tcctttttta tgtactgtgt tagcggtctg cttcttccag | 1680 |
| ccctcctgtt tgaagatggc aagttagtta cgcacaataa aaaaagacct aaaatatgta | 1740 |
| aggggtgacg ccaaagtata cactttgccc tttacacatt ttaggtcttg cctgctttat | 1800 |
| cagtaacaaa cccgcgcgat ttacttttcg acctcattct attagactct cgtttggatt | 1860 |
| gcaactggtc tatttttcctc ttttgtttga tagaaaatca taaaaggatt tgcagactac | 1920 |
| gggcctaaag aactaaaaaa tctatctgtt tcttttcatt ctctgtattt tttatagttt | 1980 |
| ctgttgcatg ggcataaagt tgccttttta atcacaattc agaaaatatc ataatatctc | 2040 |
| atttcactaa ataatagtga acggcaggta tatgtgatgg gttaaaaagg atcgatcctc | 2100 |
| tagctagagt cgatcttcgc cagcagggcg aggatcgtgg catcaccgaa ccgcgccgtg | 2160 |
| cgcgggtcgt cggtgagcca gagtttcagc aggccgccca gcggcccag tcgccattg | 2220 |
| atgcgggcca gctcgcggac gtgctcatag tccacgacgc ccgtgatttt gtagccctgg | 2280 |
| ccgacggcca gcaggtaggc cgacaggctc atgccggccg ccgccgcctt ttcctcaatc | 2340 |
| gctcttcgtt cgtctggaag gcagtacacc ttgataggtg gctgcccctt cctggttggc | 2400 |
| ttggtttcat cagccatccg cttgccctca tctgttacgc cggcggtagc cggccagcct | 2460 |
| cgcagagcag gattcccgtt gagcaccgcc aggtgcgaat aagggacagt gaagaaggaa | 2520 |
| cacccgctcg cgggtgggcc tacttcacct atcctgcccg gctgacgccg ttggatacac | 2580 |
| caaggaaagt ctacacgaac cctttggcaa atcctgtat atcgtgcgaa aaaggatgga | 2640 |
| tataccgaaa aaatcgctat aatgacccg aagcagggtt atgcagcgga aaagcgctgc | 2700 |
| ttccctgctg ttttgtggaa tatctaccga ctggaaacag gcaaatgcag gaaattactg | 2760 |

```
aactgagggg acaggcgaga gacgatgcca aagagctaca ccgacgagct ggccgagtgg   2820
gttgaatccc gcgcggccaa gaagcgccgg cgtgatgagg ctgcggttgc gttcctggcg   2880
gtgagggcgg atgtcgatat gcgtaaggag aaaataccgc atcaggcgca tgcatatttg   2940
aatgtattta gaaaataaaa caaaaagagt ttgtagaaac gcaaaaaggc catccgtcag   3000
gatggccttc tgcttaattt gatgcctggc agtttatggc gggcgtcctg cccgccaccc   3060
tccgggccgt tgcttcgcaa cgttcaaatc cgctcccggc ggatttgtcc tactcaggag   3120
agcgttcacc gacaaacaac agataaaacg aaaggcccag tctttcgact gagcctttcg   3180
ttttatttga tgcctggcag ttccctactc cgcatggggg agaccccaca ctaccatcgg   3240
cgctacggcg tttcacttct gagttcggca tggggtcagg tgggaccacc gcgctactgc   3300
cgccaggcaa attctgtttt atcagaccgc ttctgcgttc tgatttaatc tgtatcaggc   3360
tgaaaatctt ctctcatccg ccaaaacagc caagctcgcc attcgccatt caggctgcgc   3420
aactgttggg aagggcgatc ggtgcgggcc tcttcgctat tacgccagct ggcgaaaggg   3480
ggatgtgctg caaggcgatt aagttgggta acgccagggt tttcccagtc acgacgttgt   3540
aaaacgacgg ccagtgccaa gctcattacc ctgttatccc taccggtga attccaacac   3600 acaccagaca agagagctgc gtggtagttt catggccttc ttctccttgc gcaaagcgcg   3660
gtaagaggct atcctgatgt tgtctaagca tgcaggggcc tcgtgggtta atgaaaaatt   3720
aactacgggg cttttgtcct tctgccacac aacacgtaa caaaccacct tcacgtcatg   3780
aggcagaaag cctcaagcgc cgggcacatc atagcccata taccagcacg ctgaccacat   3840
tcacttttcc taagcttaca tccacaaaca gacgataacg gctctctctt ttataggtgt   3900
aaaccttaaa ctgcatttca ccagtccctg ttctcgtcag caaaagagcc gttcatttca   3960
ataaaccggg cgacctcagc catcccttcc tgattttccg cttttcagcg ttcggcacgc   4020
agacgacggg cttcattctg catggttgtg cttaccagac cggagatatt gacatcatat   4080
gccttgagca actgatagct gtcgctgtca actgtcactg taatacgctg cttcatagca   4140
cacctctttt tgacatactt cgggtataca tatcagtata tattcttatg ccgcaaaaat   4200
cagcgcgcaa atacgcatac tattatctgg cttttagtaa gccttatgta ttttacccttt   4260 cgttatgtta accaataaaa attaaaatct gccttataaa aacaaagcgt aattaccgca   4320
ttcccgtttc gtatggtcta gaggaggctc gatccagtaa acagatccat gaatgatcaa   4380
caaaggatcc attaaagatc cccataccgc tgcaaacctt gtcactcatg ggccgggacc   4440
acgatcacat aagcagtggc atgttactga taaactgtaa catgctaatg ataagctgta   4500
ttcagtaatc catatactga agtaagttaa tgacataaac tatggtcagt acgccagact   4560
cagctgttaa atacaggctg caggtttttc ttcagtcagt tagcgggct ctgacacacg   4620 atttgctgtt tattctttta ctgtccacag gcaggaggct ttctgaaaaa cgaaaattca   4680
gacatcaaaa aactgttcgg cgaggtggat aagtcgtccg gtgagctggt gacactgaca   4740
ccaaacaata caacaccgt acaacctgtg gcgctgatgc gtctgggcgt ttttgtaccg   4800
acccttaaat cactgaagaa cagtaaaaaa aatacactgt cacgtactga tgccacggaa   4860
gagctgacac gtctttccct ggccgtgct gagggattcg ataaggttga gatcaccggc   4920
ccccgcctgg atatggataa cgatttcaag acctgggtgg ggatcattca ttcctttgcc   4980
cgccataacg taattggtga caaagttgaa ctgccttttg tcgagtttgc aaaactgtgt   5040 ggtataacctt caagccagtc atcacgcagg ctgcgtgagc gcatcagccc ttccctgaaa   5100
cgcattgccg gtaccgtgat ctccttttcc cgcaccgatg agaagcacac ccgggaatac   5160
```

```
atcacccatc tggtacagtc agcctactac gatactgaac gggatattgt tcagttacag    5220
gctgatcccc gcctttttga actgtaccag tttgacagaa aggtccttct ccagcttaag    5280
gcgattaatg ccctgaagcg acgggagtcc gcccaggcac tctacacctt tatagagagc    5340
ctgccccggg atccggcacc ggtatcgctg gcgcggctgc gtgcacgcct caatctgaag    5400
tctcctgtat tttcccagaa ccagacggtc agacgggcaa tggagcagct gcgcgagatt    5460
ggatatcttg attacacgga gatccagcgg gggcggacaa aactcttctg cattcactac    5520
cggcgtcccc ggttaaaagc accgaatgat gagagtaagg aaaatccgtt gccaccttca    5580
cctgcggaaa aagtcagtcc ggagatggcg gagaagcttg ccctgcttga gaaactgggc    5640
atcacgctgg atgacctgga aaaactcttc aaatcccgct gaacataaac tgtagtcagt    5700
gaagagtgtt cctttactga ctacagctta tattatcagg tgcagtgagt ggtctgctca    5760
ctgcagttta tattcagttt cctgcagtgc tgcctgtagc tgagctgtca tctgccggtc    5820
ccttacgtga gtcaccccgt aacctgatgc tgaggcattg ctcccttcat aaaacatgac    5880
ttactcacta cagcttatat acatgctcca gcttatgtta tgtctgttct gctgaccaca    5940
gcttgtcgac tgaagatcag tcacaccatc ctgcacttac aatgcgcaga aggagcgagc    6000
acagaaagaa gtcttgaact tttccgagca tataactata ctccccgcat agctgaattg    6060
ttggctatac ggtttaagtg ggccccggta atcttctcag tcgccaaact ttctgaagat    6120
tatcggggtt tttgcttttc tggctcctgt aaatccacat cagaaccagt tccctgccac    6180
cttacggcgt ggccagccac aaaattcctt aaacgatcag taatctagca ctaatcttct    6240
gaacactcaa gaatgtaagc ccatcatcac acacatcgtt tttgcgcttc acttttttatc    6300
agtgcggtca gaacttcagc ctgagtcagg ccatcttcat gacacatttg catgagcatg    6360
gccttatact ttggttcaag aaatactttt acttccttga acgaagctct tttacgggcc    6420
actgataatc tttgtttctc tgcatcagaa agcggattcc cctttctgta tgctcgtttt    6480
gcgccagatg aggaagtcac tgcattttct gtctgcgaca tctcgcctcc tcaatactta    6540
aacagggatc gtttcgcaga ggatactaca gttttttgaa atcagcgact tgagaattgt    6600
gacgaagatc cgggattacc ctgttatccc tagagcttgg cgtaatcatg gtcatagctg    6660
tttcctgtgt gaaattgtta tccgctcaca attccacaca acatacgagc cggaagcata    6720
aagtgtaaag cctggggtgc ctaatgagtg agctaactca cattaattgc gttgcgctca    6780
ctgcccgctt tccagtcggg aaacctgtcg tgccagctgc attaatgaat cggccaacgc    6840
gcggggagag gcggttttgc gtattgggcgc tcttccgctt cctcgctcac tgactcgctg    6900
cgctcggtcg ttcggctgcg gcgagcggta tcagctcact caaaggcggt aatacggtta    6960
tccacagaat caggggataa cgcaggaaag aacatgtgag caaaaggcca gcaaaaggcc    7020
aggaaccgta aaaaggccgc gttgctggcg ttttccata ggctccgccc ccctgacgag    7080
catcacaaaa atcgacgctc aagtcagagg tggcgaaacc cgacaggact ataaagatac    7140
caggcgtttc ccctggaagc tccctcgtg cgctctcctg ttccgaccct gccgcttacc    7200
ggatacctgt ccgcctttct cccttcggga agcgtggcgc tttctcatag ctcacgctgt    7260
aggtatctca gttcggtgta ggtcgttcgc tccaagctgg gctgtgtgca cgaaccccc    7320
gttcagcccg accgctgcgc cttatccggt aactatcgtc ttgagtccaa cccggtaaga    7380
cacgacttat cgccactggc agcagccact ggtaacagga ttagcagagc gaggtatgta    7440
ggcggtgcta cagagttctt gaagtggtgg cctaactacg gctacactag aaggacagta    7500
tttggtatct gcgctctgct gaagccagtt accttcggaa aaagagttgg tagctcttga    7560
```

```
tccggcaaac aaaccaccgc tggtagcggt ggttttttg tttgcaagca gcagattacg    7620
cgcagaaaaa aaggatctca agaagatcct ttgatctttt ctacggggtc tgacgctcag    7680
tggaacgaaa actcacgtta agggattttg gtcatgagat tatcaaaaag gatcttcacc    7740
tagatccttt taaattaaaa atgaagtttt aaatcaatct aaagtatata tgagtaaact    7800
tggtctgaca gttaccaatg cttaatcagt gaggcaccta tctcagcgat ctgtctattt    7860
cgttcatcca tagttgcctg actccccgtc gtgtagataa ctacgatacg ggagggctta    7920
ccatctggcc ccagtgctgc aatgataccg cgagacccac gctcaccggc tccagattta    7980
tcagcaataa accagccagc cggaagggcc gagcgcagaa gtggtcctgc aactttatcc    8040
gcctccatcc agtctattaa ttgttgccgg gaagctagag taagtagttc gccagttaat    8100
agtttgcgca acgttgttgc cattgctaca ggcatcgtgg tgtcacgctc gtcgtttggt    8160
atggcttcat tcagctccgg ttcccaacga tcaaggcgag ttacatgatc ccccatgttg    8220
tgcaaaaaag cggttagctc cttcggtcct ccgatcgttg tcagaagtaa gttggccgca    8280
gtgttatcac tcatggttat ggcagcactg cataattctc ttactgtcat gccatccgta    8340
agatgctttt ctgtgactgg tgagtactca accaagtcat tctgagaata gtgtatgcgg    8400
cgaccgagtt gctcttgccc ggcgtcaata cgggataata ccgcgccaca tagcagaact    8460
ttaaaagtgc tcatcattgg aaaacgttct tcggggcgaa aactctcaag gatcttaccg    8520
ctgttgagat ccagttcgat gtaacccact cgtgcaccca actgatcttc agcatctttt    8580
actttcacca gcgtttctgg gtgagcaaaa acaggaaggc aaaatgccgc aaaaaaggga    8640
ataagggcga cacggaaatg ttgaatactc atactcttcc tttttcaatg gggtgggcga    8700
agaactccag catgagatcc ccgcgctgga ggatcatcca gccggcgtcc cggaaaacga    8760
ttccgaagcc caacctttca tagaaggcgg cggtggaatc gaaatctcgt gatggcaggt    8820
tgggcgtcgc ttggtcggtc atttcgaacc ccagagtccc gctcagaaga actcgtcaag    8880
aaggcgatag aaggcgatgc gctgcgaatc gggagcggcg ataccgtaaa gcacgaggaa    8940
gcggtcagcc cattcgccgc caagctcttc agcaatatca cgggtagcca acgctatgtc    9000
ctgatagcgg tccgccacac ccagccggcc acagtcgatg aatccagaaa agcggccatt    9060
ttccaccatg atattcggca agcaggcatc gccatgggtc acgacgagat cctcgccgtc    9120
gggcatgcgc gccttgagcc tggcgaacag ttcggctggc gcgagcccct gatgctcttc    9180
gtccagatca tcctgatcga caagaccggc ttccatccga gtacgtgctc gctcgatgcg    9240
atgtttcgct tggtggtcga atgggcaggt agccggatca agcgtatgca gccgccgcat    9300
tgcatcagcc atgatggata cttttctcgg caggagcaagg tgagatgaca ggagatcctg    9360
ccccggcact tcgcccaata gcagccagtc ccttcccgct tcagtgacaa cgtcgagcac    9420
agctgcgcaa ggaacgcccg tcgtggccag ccacgatagc cgcgctgcct cgtcctgcag    9480
ttcattcagg gcaccggaca ggtcggtctt gacaaaaaga accgggcgcc cctgcgctga    9540
cagccggaac acggcggcat cagagcagcc gattgtctgt tgtgcccagt catagccgaa    9600
tagcctctcc acccaagcgg ccggagaacc tgcgtgcaat ccatcttgtt caatcatgcg    9660
aaacgatcct catcctgtct cttgatcaga tcttgatccc ctgcgccatc agatccttgg    9720
cggcaagaaa gccatccagt ttactttgca gggcttccca accttaccag agggcgcccc    9780
agctggcaat tccggttcgc ttgctgtcca taaaaccgcc cagtctagct atcgccatgt    9840
aagcccactg caagctacct gctttctctt tgcgcttgcg ttttcccttg tccagatagc    9900
ccagtagctg acattcatcc ggggtcagca ccgtttctgc ggactggctt tctacgtgtt    9960
```

-continued

```
ccgcttcctt tagcagccct tgcgccctga gtgcttgcgg cagcgtgaag ctattattga   10020
agcatttatc agggttattg tctcatgagc ggatacatat ttgaatgtat ttagaaaaat   10080
aaacaaatag gggttccgcg cacatttccc cgaaaagtgc cacctgacgt ctaagaaacc   10140
attattatca tgacattaac ctataaaaat aggcgtatca cgaggcgccc tttcgtc      10197
```

<210> SEQ ID NO 3
<211> LENGTH: 12002
<212> TYPE: DNA
<213> ORGANISM: Artificial
<220> FEATURE:
<223> OTHER INFORMATION: Derivative of pCURE1 based on vector pAKE604

<400> SEQUENCE: 3

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataatcg gcattttctt ttgcgttttt atttgttaac tgttaattgt ccttgttcaa    240
ggatgctgtc tttgacaaca gatgttttct tgcctttgat gttcagcagg aagctaggcg    300
caaacgttga ttgtttgtct gcgtagaatc ctctgttttgt catatagctt gtaatcacga    360
cattgtttcc tttcgcttga ggtacagcga agtgtgagta agtaaaggtt acatcgttag    420
gatcaagatc cattttttaac acaaggccag ttttgttcag cggcttgtat gggccagtta    480
aagaattaga aacataacca agcatgtaaa tatcgttaga cgtaatgccg tcaatcgtca    540 ttttttgatcc gcgggagtca gtgaacagat accattgcc gttcatttta aagacgttcg    600
cgcgttcaat ttcatctgtt actgtgttag atgcaatcag cggtttcatc acttttttca    660
gtgtgtaatc atcgtttagc tcaatcatac cgagagcgcc gtttgctaac tcagccgtgc    720
gttttttatc gcttttgcaga agttttttgac tttcttgacg gaagaatgat gtgcttttgc    780
catagtatgc tttgttaaat aaagattctt cgccttggta gccatcttca gttccagtgt    840
ttgcttcaaa tactaagtat ttgtggcctt tatcttctac gtagtgagga tctctcagcg    900
tatggttgtc gcctgagctg tagttgcctt catcgatgaa ctgctgtaca ttttgatacg    960
tttttccgtc accgtcaaag attgatttat aatcctctac accgttgatg ttcaaagagc    1020
tgtctgatgc tgatacgtta acttgtgcag ttgtcagtgt ttgtttgccg taatgtttac    1080
cggagaaatc agtgtagaat aaacggattt ttccgtcaga tgtaaatgtg gctgaacctg    1140
accattcttg tgtttggtct tttaggatag aatcatttgc atcgaatttg tcgctgtctt    1200
taaagacgcg gccagcgttt ttccagctgt caatagaagt ttcgccgact ttttgataga    1260
acatgtaaat cgatgtgtca tccgcatttt taggatctcc ggctaatgca aagacgatgt    1320
ggtagccgtg atagtttgcg acagtgccgt cagcgttttg taatggccag ctgtcccaaa    1380
cgtccaggcc ttttgcagaa gagatatttt taattgtgga cgaatcgaac tcaggaactt    1440 gatattttc attttttttgc tgttcaggga tttcagcat atcatggcgt gtaatatggg    1500
aaatgccgta tgtttcctta tatggctttt ggttcgtttc tttcgcaaac gcttgagttg    1560
cgcctcctgc cagcagtgcg gtagtaaagg ttaatactgt tgcttgtttt gcaaactttt    1620
tgatgttcat cgttcatgtc tcctttttta tgtactgtgt tagcggtctg cttcttccag    1680
ccctcctgtt tgaagatggc aagttagtta cgcacaataa aaaagacct aaatatgta    1740 aggggtgacg ccaaagtata cactttgccc tttacacatt ttaggtcttg cctgctttat    1800
cagtaacaaa cccgcgcgat ttacttttcg acctcattct attagactct cgtttggatt    1860
```

```
gcaactggtc tattttcctc ttttgtttga tagaaaatca taaaaggatt tgcagactac    1920
gggcctaaag aactaaaaaa tctatctgtt tcttttcatt ctctgtattt tttatagttt    1980
ctgttgcatg gcataaagt tgccttttta atcacaattc agaaaatatc ataatatctc     2040
atttcactaa ataatagtga acggcaggta tatgtgatgg gttaaaaagg atcgatcctc    2100
tagctagagt cgatcttcgc cagcagggcg aggatcgtgg catcaccgaa ccgcgccgtg    2160
cgcgggtcgt cggtgagcca gagtttcagc aggccgccca ggcggcccag gtcgccattg    2220
atgcgggcca gctcgcggac gtgctcatag tccacgacgc ccgtgatttt gtagccctgg    2280
ccgacggcca gcaggtaggc cgacaggctc atgccgccg ccgccgcctt ttcctcaatc     2340
gctcttcgtt cgtctggaag gcagtacacc ttgataggtg ggctgcccct cctggttggc    2400
ttggtttcat cagccatccg cttgccctca tctgttacgc cggcggtagc cggccagcct    2460
cgcagagcag gattcccgtt gagcaccgcc aggtgcgaat aagggacagt gaagaaggaa    2520
cacccgctcg cgggtgggcc tacttcacct atcctgcccg gctgacgccg ttggatacac    2580
caaggaaagt ctacacgaac cctttggcaa atcctgtat atcgtgcgaa aaaggatgga     2640
tataccgaaa aaatcgctat aatgaccccg aagcagggtt atgcagcgga aaagcgctgc    2700
ttccctgctg ttttgtggaa tatctaccga ctggaaacag gcaaatgcag gaaattactg    2760
aactgagggg acaggcgaga gacgatgcca aagagctaca ccgacgagct ggccgagtgg    2820
gttgaatccc gcgcggccaa gaagcgccgg cgtgatgagg ctgcggttgc gttcctggcg    2880
gtgagggcgg atgtcgatat gcgtaaggag aaaataccgc atcaggcgca tgcatatttg    2940
aatgtattta gaaaaataaa caaaaagagt tgtagaaaac gcaaaaggc catccgtcag     3000 gatggccttc tgcttaattt gatgcctggc agtttatggc gggcgtcctg cccgccaccc    3060
tccgggccgt tgcttcgcaa cgttcaaatc cgctcccggc ggatttgtcc tactcaggag    3120
agcgttcacc gacaaacaac agataaaacg aaaggcccag tctttcgact gagcctttcg    3180
ttttatttga tgcctggcag ttccctactc tcgcatgggg agaccccaca ctaccatcgg    3240
cgctacggcg tttcacttct gagttcggca tggggtcagg tgggaccacc gcgctactgc    3300
cgccaggcaa attctgtttt atcagaccgc ttctgcgttc tgatttaatc tgtatcaggc    3360
tgaaaatctt ctctcatccg ccaaaacagc caagctcgcc attcgccatt caggctgcgc    3420
aactgttggg aagggcgatc ggtgcgggcc tcttcgctat tacgccagct ggcgaaaggg    3480
ggatgtgctg caaggcgatt aagttgggta acgccagggt ttcccagtc acgacgttgt     3540 aaaacgacgg ccagtgccaa gctcattacc ctgttatccc taccggtga attccaacac     3600 acaccagaca agagagctgc gtggtagttt catggccttc ttctccttgc gcaaagcgcg    3660
gtaagaggct atcctgatgt tgtctaagca tgcaggggcc tcgtgggtta atgaaaaatt    3720
aactacgggg cttttgtcct tctgccacac aacacggtaa caaaccacct tcacgtcatg    3780
aggcagaaag cctcaagcgc cgggcacatc atagcccata taccagcacg ctgaccacat    3840
tcacttttcc taagcttaca tccacaaaca gacgataacg gctctctctt ttataggtgt    3900
aaaccttaaa ctgcatttca ccagtccctg ttctcgtcag caaaagagcc gttcatttca    3960
ataaaccggg cgacctcagc catcccttcc tgattttccg ctttccagcg ttcggcacgc    4020
agacgacggg cttcattctg catggttgtg cttaccagac cggagatatt gacatcatat    4080
gccttgagca actgatagct gtcgctgtca actgtcactg taatacgctg cttcatagca    4140
cacctctttt tgacatactt cgggtataca tatcagtata tattcttatg ccgcaaaaat    4200
```

```
cagcgcgcaa atacgcatac tattatctgg ctttttagtaa gccttatgta ttttacctttt   4260 cgttatgtta accaataaaa attaaaatct gccttataaa aacaaagcgt aattaccgca   4320
ttcccgtttc gtatggtcta gcaccacgct gggtttactg tttggttgaa agttatattt   4380
ttattaaaca ttgtgcgtta aagcctggtg tgttttttta gtggatgtta tatttaaata   4440
taacttttat ggaggtgaag aatgcatacc acccgactga agagggttgg cggctcagtt   4500
atgctgaccg tcccaccggc actgctgaat gcgctgtctc tgggcacaga taatgaagtt   4560
ggcatggtca ttgataatgg ccggctgatt gttgagccgt acagacgccc gcaatattca   4620
ctggctgagc tactggcaca gtgtgatccg aatgctgaaa tatcagctga agaacgagaa   4680
tggctggatg caccggcgac tggtcaggag gaaatctgac atggaaagag gggaaatctg   4740
gcttgtctcg ctggatcggg tacctctcgc acagcgattt tcgtgtcaga taagtgaata   4800
tcaacagtgt gagacacacg atcaacacac accagacaag gaacttcgt ggtagtttca   4860 tggccttctt ctccttgcgc aaagcgcggt aagaggctat cctgatgtgg actagacata   4920
gggatgcctc gtggtggtta atgaaaatta acttactacg gggctatctt ctttctgcca   4980
cacaacacgg caacaaacca ccttcacgtc atgaggcaga aagcctcaag cggctagagg   5040
aggctcgatc cagtaaacag atccatgaat gatcaacaaa ggatccatta aagatcccca   5100
taccgctgca aaccttgtca ctcatgggcc gggaccacga tcacataagc agtggcatgt   5160
tactgataaa ctgtaacatg ctaatgataa gctgtattca gtaatccata tactgaagta   5220
agttaatgac ataaactatg gtcagtacgc cagactcagc tgttaaatac aggctgcagg   5280
tttttcttca gtcagttagc ggggctctga cacacgattt gctgtttatt ctttttactgt   5340 ccacaggcag gaggctttct ggaaaacgaa aattcagaca tcaaaaaact gttcggcgag   5400
gtggataagt cgtccggtga gctggtgaca ctgacaccaa acaataacaa caccgtacaa   5460
cctgtggcgc tgatgcgtct gggcgttttt gtaccgaccc ttaaatcact gaagaacagt   5520
aaaaaaaata cactgtcacg tactgatgcc acggaagagc tgacacgtct ttccctggcc   5580
cgtgctgagg gattcgataa ggttgagatc accggccccc gcctggatat ggataacgat   5640
ttcaagacct gggtggggat cattcattcc tttgcccgcc ataacgtaat tggtgacaaa   5700
gttgaactgc cttttgtcga gtttgcaaaa ctgtgtggta taccttcaag ccagtcatca   5760
cgcaggctgc gtgagcgcat cagcccttcc ctgaaacgca ttgccggtac cgtgatctcc   5820 tttttcccgca ccgatgagaa gcacacccgg gaatacatca cccatctggt acagtcagcc   5880
tactacgata ctgaacggga tattgttcag ttacaggctg atccccgcct ttttgaactg   5940
taccagtttg acagaaaggt ccttctccag cttaaggcga ttaatgccct gaagcgacgg   6000
gagtccgccc aggcactcta cacctttata gagagcctgc cccgggatcc ggcaccggta   6060
tcgctggcgc ggctgcgtgc acgcctcaat ctgaagtctc ctgtattttc ccagaaccag   6120
acggtcagac gggcaatgga gcagctgcgc gagattggat atcttgatta cacggagatc   6180
cagcgggggc ggacaaaact cttctgcatt cactaccggc gtccccggtt aaaagcaccg   6240
aatgatgaga gtaaggaaaa tccgttgcca ccttcacctg cggaaaaagt cagtccggag   6300
atggcggaga agcttgccct gcttgagaaa ctgggcatca cgctggatga cctggaaaaa   6360
ctcttcaaat cccgctgaac ataaactgta gtcagtgaag agtgttcctt tactgactac   6420
agcttatatt atcaggtgca gtgagtggtc tgctcactgc agtttatatt cagtttcctg   6480
cagtgctgcc tgtagctgag ctgtcatctg ccggtccctt acgtgagtca ccccgtaacc   6540
tgatgctgag gcattgctcc cttcataaaa catgacttac tcactacagc ttatatacat   6600
```

```
gctccagctt atgttatgtc tgttctgctg accacagctt gtcgagggaa cggactggaa   6660
acagacgtac tgacatccca ggaaacgatc ttgaaacgta aaccgtgcgc caacacaggt   6720
tacgttcata aagtaagtcg ctgattttag aaatctgtag tattctctgc aaacgatcta   6780
ggtttgatcc ttgaggagac agagatgtcg cagattgaaa atgcagtaac ttcctcatcg   6840
aaacgcattt acagaaaggg taatccctta tcttccgctg agaagaagag attatctatt   6900
tcacgaaaaa agacgacgca taaagagctc aatgttttca tacaaaacat acataaagaa   6960
agcttgcagc agctttgtga agagactgga actactcagg ctcaaatgat tgagctacta   7020
attgaacggg aaatggctaa aagagcctga gataagaagg tgaatgagta actttcttga   7080
tcgtctcgtc agtgagtgtt agattgctga tcgtctaaag aattttgatg gctggccacg   7140
ccgtaaggtg gcagggaact ggttctgatg aggtgcctac ccgggaccag aaaagcaaaa   7200
accccgataa tcttctcatt tcttggcggg aacgaaagat taacggggcc tacttaaact   7260
gtatagccac caatcaggct atgcagggag tatagtttta tgctcagaaa atttcaatac   7320
ttgtttctgt ggcatttact ccttccgtgc attgtaagtg caggcagaag tgactgacac   7380
ccgaacactt ttcactcatt accgacaggg gatccgccag acgactcata tcgtattttc   7440
cttccgcgat atcacttcca tgacgacagg atagtctgag ggttatctgt cacagatttg   7500
agggtggttc gtcacatttg ttctgaccta ctgagggtaa tttgtcacag ttttgctgtt   7560
tccttcagcc tgcatggatt ttctcatact ttttgaactg taattttaa ggaagccaaa    7620 tttgagggca gtttgtcaca gttgatttcc ttctcttcc cttcgtcatg tgacctgata    7680
tcgggggtta gttcgtcatc attgatgagg gttgattatc acagtttatt actctgaatt   7740
ggctatccgc tcgactgaag atcagtcaca ccatcctgca cttacaatgc gcagaaggag   7800
cgagcacaga aagaagtctt gaacttttcc gagcatataa ctatactccc cgcatagctg   7860
aattgttggc tataccggttt aagtgggccc cggtaatctt ctcagtcgcc aaactttctg   7920
aagattatcg gggttttgc ttttctggct cctgtaaatc cacatcagaa ccagttccct    7980
gccaccttac ggcgtggcca gccacaaaat tccttaaacg atcagtaatc tagcactaat   8040
cttctgaaca ctcaagaatg taagcccatc atcacacaca tcgttttgc gcttcacttt    8100 ttatcagtgc ggtcagaact tcagcctgag tcaggccatc ttcatgacac atttgcatga   8160
gcatggcctt atactttggt tcaagaaata ctttttactt cttgaacgaa gctcttttac   8220
gggccactga taatctttgt ttctctgcat cagaaagcgg attcccctttt ctgtatgctc   8280 gttttgcgcc agatgaggaa gtcactgcat tttctgtctg cgacatctcg cctcctcaat   8340
acttaaacag ggatcgtttc gcagaggata ctacagtttt ttgaaatcag cgacttgaga   8400
attgtgacga agatccggga ttaccctgtt atccctagag cttggcgtaa tcatggtcat   8460
agctgtttcc tgtgtgaaat tgttatccgc tcacaattcc acacaacata cgagccggaa   8520
gcataaagtg taaagcctgg ggtgcctaat gagtgagcta actcacatta attgcgttgc   8580
gctcactgcc cgctttccag tcgggaaacc tgtcgtgcca gctgcattaa tgaatcggcc   8640
aacgcgcggg gagaggcggt ttgcgtattg ggcgctcttc cgcttcctcg ctcactgact   8700
cgctgcgctc ggtcgttcgg ctgcggcgag cggtatcagc tcactcaaag gcggtaatac   8760
ggttatccac agaatcaggg gataacgcag gaaagaacat gtgagcaaaa ggccagcaaa   8820
aggccaggaa ccgtaaaaag gccgcgttgc tggcgttttt ccataggctc cgcccccctg   8880
acgagcatca caaaaatcga cgctcaagtc agaggtggcg aaacccgaca ggactataaa   8940
```

```
gataccaggc gtttcccct ggaagctccc tcgtgcgctc tcctgttccg accctgccgc   9000
ttaccggata cctgtccgcc tttctccctt cgggaagcgt ggcgctttct catagctcac   9060
gctgtaggta tctcagttcg gtgtaggtcg ttcgctccaa gctgggctgt gtgcacgaac   9120
cccccgttca gcccgaccgc tgcgccttat ccggtaacta tcgtcttgag tccaacccgg   9180
taagacacga cttatcgcca ctggcagcag ccactggtaa caggattagc agagcgaggt   9240
atgtaggcgg tgctacagag ttcttgaagt ggtggcctaa ctacggctac actagaagga   9300
cagtatttgg tatctgcgct ctgctgaagc cagttacctt cggaaaaaga gttggtagct   9360
cttgatccgg caaacaaacc accgctggta gcggtggttt ttttgtttgc aagcagcaga   9420
ttacgcgcag aaaaaaagga tctcaagaag atcctttgat cttttctacg ggtctgacg   9480 ctcagtggaa cgaaaactca cgttaaggga ttttggtcat gagattatca aaaggatct   9540 tcacctagat ccttttaaat taaaaatgaa gttttaaatc aatctaaagt atatatgagt   9600
aaacttggtc tgacagttac caatgcttaa tcagtgaggc acctatctca gcgatctgtc   9660
tatttcgttc atccatagtt gcctgactcc ccgtcgtgta gataactacg atacgggagg   9720
gcttaccatc tggccccagt gctgcaatga taccgcgaga cccacgctca ccggctccag   9780
atttatcagc aataaaccag ccagccggaa gggccgagcg cagaagtggt cctgcaactt   9840
tatccgcctc catccagtct attaattgtt gccgggaagc tagagtaagt agttcgccag   9900
ttaatagttt gcgcaacgtt gttgccattg ctacaggcat cgtggtgtca cgctcgtcgt   9960
ttggtatggc ttcattcagc tccggttccc aacgatcaag gcgagttaca tgatccccca  10020
tgttgtgcaa aaaagcggtt agctccttcg gtcctccgat cgttgtcaga agtaagttgg  10080
ccgcagtgtt atcactcatg gttatggcag cactgcataa ttctcttact gtcatgccat  10140
ccgtaagatg cttttctgtg actggtgagt actcaaccaa gtcattctga agtagtgta  10200 tgcggcgacc gagttgctct tgcccggcgt caatacggga taataccgcg ccacatagca  10260
gaactttaaa agtgctcatc attggaaaac gttcttcggg gcgaaaactc tcaaggatct  10320
taccgctgtt gagatccagt tcgatgtaac ccactcgtgc acccaactga tcttcagcat  10380
cttttacttt caccagcgtt tctgggtgag caaaaacagg aaggcaaaat gccgcaaaaa  10440
agggaataag ggcgacacgg aaatgttgaa tactcatact cttccttttt caatggggtg  10500
ggcgaagaac tccagcatga gatcccccgcg ctggaggatc atccagccgg cgtcccggaa  10560
aacgattccg aagcccaacc tttcatagaa ggcggcggtg aatcgaaat ctcgtgatgg  10620 caggttgggc gtcgcttggt cggtcatttc gaacccagga gtcccgctca aagaactcg  10680 tcaagaaggc gatagaaggc gatgcgctgc gaatcgggag cggcgatacc gtaaagcacg  10740
aggaagcggt cagcccattc gccgccaagc tcttcagcaa tatcacgggt agccaacgct  10800
atgtcctgat agcggtccgc cacacccagc cggccacagt cgatgaatcc agaaaagcgg  10860
ccattttcca ccatgatatt cggcaagcag gcatcgccat gggtcacgac gagatcctcg  10920
ccgtcgggca tgcgcgcctt gagcctggcg aacagttcgg ctggcgcgag ccctgatgc  10980 tcttcgtcca gatcatcctg atcgacaaga ccggcttcca tccgagtacg tgctcgctcg  11040
atgcgatgtt tcgcttggtg gtcgaatggg caggtagccg gatcaagcgt atgcagccgc  11100
cgcattgcat cagccatgat ggatactttc tcggcaggag caaggtgaga tgacaggaga  11160
tcctgccccg gcacttcgcc caatagcagc cagtcccttc ccgcttcagt gacaacgtcg  11220
agcacagctc cgcaaggaac gcccgtcgtg gccagccacg atagccgcgc tgcctcgtcc  11280
tgcagttcat tcagggcacc ggacaggtcg gtcttgacaa aaagaaccgg gcgcccctgc  11340
```

```
gctgacagcc ggaacacggc ggcatcagag cagccgattg tctgttgtgc ccagtcatag    11400
ccgaatagcc tctccaccca agcggccgga gaacctgcgt gcaatccatc ttgttcaatc    11460
atgcgaaacg atcctcatcc tgtctcttga tcagatcttg atccctgcg ccatcagatc     11520 cttggcggca agaaagccat ccagtttact ttgcagggct cccaacctt accagagggc     11580 gccccagctg gcaattccgg ttcgcttgct gtccataaaa ccgcccagtc tagctatcgc    11640
catgtaagcc cactgcaagc tacctgcttt ctctttgcgc ttgcgttttc ccttgtccag    11700
atagcccagt agctgacatt catccggggt cagcaccgtt tctgcggact ggctttctac    11760
gtgttccgct tcctttagca gcccttgcgc cctgagtgct gcggcagcg tgaagctatt     11820 attgaagcat ttatcagggt tattgtctca tgagcggata catatttgaa tgtatttaga    11880
aaaataaaca aatagggggtt ccgcgcacat ttccccgaaa agtgccacct gacgtctaag    11940
aaaccattat tatcatgaca ttaacctata aaaataggcg tatcacgagg cgcccttttcg   12000 tc                                                                    12002

<210> SEQ ID NO 4
<211> LENGTH: 9419
<212> TYPE: DNA
<213> ORGANISM: Artificial
<220> FEATURE:
<223> OTHER INFORMATION: Derivative of vector pAKE604

<400> SEQUENCE: 4
tcgcgcgttt cggtgatgac ggtgaaaacc tctgacacat gcagctcccg gagacggtca      60
cagcttgtct gtaagcggat gccggagcag acaagcccg tcagggcgcg tcagcgggtg      120
ttggcgggtg tcggggctgg cttaactatg cggcatcaga gcagattgta ctgagagtgc     180
accataatcg gcattttctt ttgcgttttt atttgttaac tgttaattgt ccttgttcaa     240
ggatgctgtc tttgacaaca gatgttttct tgcctttgat gttcagcagg aagctaggcg     300
caaacgttga ttgtttgtct gcgtagaatc ctctgtttgt catatagctt gtaatcacga     360
cattgtttcc tttcgcttga ggtacagcga agtgtgagta agtaaaggtt acatcgttag     420
gatcaagatc cattttaac acaaggccag ttttgttcag cggcttgtat gggccagtta      480
aagaattaga aacataacca agcatgtaaa tatcgttaga cgtaatgccg tcaatcgtca     540
tttttgatcc gcgggagtca gtgaacagat accatttgcc gttcattta aagacgttcg     600 cgcgttcaat ttcatctgtt actgtgttag atgcaatcag cggtttcatc acttttttca    660
gtgtgtaatc atcgtttagc tcaatcatac cgagagcgcc gtttgctaac tcagccgtgc     720 gtttttatc gctttgcaga agttttgac tttcttgacg gaagaatgat gtgcttttgc       780
catagtatgc tttgttaaat aaagattctt cgccttggta gccatcttca gttccagtgt     840
ttgcttcaaa tactaagtat ttgtggcctt tatcttctac gtagtgagga tctctcagcg    900
tatggttgtc gcctgagctg tagttgcctt catcgatgaa ctgctgtaca ttttgatacg    960
tttttccgtc accgtcaaag attgatttat aatcctctac accgttgatg ttcaaagagc   1020
tgtctgatgc tgatacgtta acttgtgcag ttgtcagtgt ttgtttgccg taatgtttac   1080
cggagaaatc agtgtagaat aaacggattt ttccgtcaga tgtaaatgtg ctgaacctg    1140 accattcttg tgtttggtct tttaggatag aatcatttgc atcgaatttg tcgctgtctt   1200
taaagacgcg gccagcgttt ttccagctgt caatagaagt ttcgccgact ttttgataga   1260
acatgtaaat cgatgtgtca tccgcatttt taggatctcc ggctaatgca aagacgatgt   1320
```

```
ggtagccgtg atagtttgcg acagtgccgt cagcgttttg taatggccag ctgtcccaaa    1380
cgtccaggcc ttttgcagaa gagatatttt taattgtgga cgaatcgaac tcaggaactt    1440
gatatttttc attttttttgc tgttcaggga tttgcagcat atcatggcgt gtaatatggg   1500
aaatgccgta tgtttcctta tatggctttt ggttcgtttc tttcgcaaac gcttgagttg    1560
cgcctcctgc cagcagtgcg gtagtaaagg ttaatactgt tgcttgtttt gcaaactttt    1620
tgatgttcat cgttcatgtc tccttttttta tgtactgtgt tagcggtctg cttcttccag   1680
ccctcctgtt tgaagatggc aagttagtta cgcacaataa aaaagacct aaaatatgta     1740 aggggtgacg ccaaagtata cactttgccc tttacacatt ttaggtcttg cctgctttat    1800
cagtaacaaa cccgcgcgat ttacttttcg acctcattct attagactct cgtttggatt    1860
gcaactggtc tattttcctc ttttgtttga tagaaaatca taaaaggatt tgcagactac    1920
gggcctaaag aactaaaaaa tctatctgtt tcttttcatt ctctgtattt tttatagttt    1980
ctgttgcatg gcataaagt tgccttttta atcacaattc agaaaatatc ataatatctc     2040
atttcactaa ataatagtga acggcaggta tatgtgatgg gttaaaaagg atcgatcctc    2100
tagctagagt cgatcttcgc cagcagggcg aggatcgtgg catcaccgaa ccgcgccgtg    2160
cgcgggtcgt cggtgagcca gagtttcagc aggccgccca ggcggcccag gtcgccattg    2220
atgcgggcca gctcgcggac gtgctcatag tccacgacgc ccgtgatttt gtagccctgg    2280
ccgacggcca gcaggtaggc cgacaggctc atgccgccg ccgccgcctt ttcctcaatc     2340
gctcttcgtt cgtctggaag gcagtacacc ttgataggtg ggctgccctt cctggttggc    2400
ttggtttcat cagccatccg cttgccctca tctgttacgc cggcggtagc cggccagcct    2460
cgcagagcag gattcccgtt gagcaccgcc aggtgcgaat aagggacagt gaagaaggaa    2520
cacccgctcg cgggtgggcc tacttcacct atcctgcccg gctgacgccg ttggatacac    2580
caaggaaagt ctacacgaac cctttggcaa atcctgtat atcgtgcgaa aaggatgga     2640 tataccgaaa aaatcgctat aatgaccccg aagcagggtt atgcagcgga aaagcgctgc    2700
ttccctgctg ttttgtggaa tatctaccga ctggaaacag gcaaatgcag gaaattactg    2760
aactgagggg acaggcgaga gacgatgcca aagagctaca ccgacgagct ggccgagtgg    2820
gttgaatccc gcgcggccaa gaagcgccgg cgtgatgagg ctgcggttgc gttcctggcg    2880 gtgagggcg atgtcgatat gcgtaaggag aaaataccgc atcaggcgca tgcatatttg    2940
aatgtattta gaaaaataaa caaaaagagt ttgtagaaac gcaaaaaggc catccgtcag    3000
gatggccttc tgcttaattt gatgcctggc agtttatggc gggcgtcctg cccgccaccc    3060
tccgggccgt tgcttcgcaa cgttcaaatc cgctcccggc ggatttgtcc tactcaggag    3120
agcgttcacc gacaaacaac agataaaacg aaaggcccag tctttcgact gagcctttcg    3180
ttttatttga tgcctggcag ttccctactc tcgcatgggg agaccccaca ctaccatcgg    3240
cgctacggcg tttcacttct gagttcggca tggggtcagg tgggaccacc gcgctactgc    3300
cgccaggcaa attctgtttt atcagaccgc ttctgcgttc tgatttaatc tgtatcaggc    3360
tgaaaatctt ctctcatccg ccaaaacagc caagctcgcc attcgccatt caggctgcgc    3420
aactgttggg aagggcgatc ggtgcgggcc tcttcgctat tacgccagct ggcgaaaggg    3480
ggatgtgctg caaggcgatt aagttgggta acgccagggt tttcccagtc acgacgttgt    3540
aaaacgacgg ccagtgccaa gctcattacc ctgttatccc tacccggtga attcagcgca    3600
ttttcccgac cttaatgcgc ctcgcgctgt agcctcacgc ccacatatgt gctaatgtgg    3660
ttacgtgtat tttatggagg ttatccaatg agccgcctga caatcgacat gacggaccag    3720
```

```
cagcaccaga gcctgaaagc cctggccgcc ttgcagggca agaccattaa gcaatacgcc   3780
ctcgaacgtc tgttccccgg tgacgctgat gccgatcagg catggcagga actgaaaacc   3840
atgctgggga accgcatcaa cgatgggctt gccggcaagg tgtccaccaa gagcgtcggc   3900
gaaattcttg atgaagaact cagcggggat cgcgcttgac ggcctacatc ctcacggctg   3960
ggatctaagg acgagtttta gcggctaaag gtgttgacgt gcgagaaatg tttagctaaa   4020
cttctctcat gtgctggcgg ctgtcaccgc tatgttcaac caaggcgcgg agcaaattat   4080
gggtgttatc catgaagaaa cggcttaccg aaagccagtt ccaggaggcg atccaggggc   4140
tggaagtggg gcagcagacc atcgagatag cgcggggcgt cttagtcgat gggaagccac   4200
aggcgacgtt cgcaacgtcg ctgggactga ccaggggcgc agtgtcgcaa gcggtgcatc   4260
gcgtgtgggc cgcgttcgag gacaagaact gcccgaggg gtacgcgcgg gtaacggcgg    4320
ttctgccgga acatcaggcg tacatcgtcc ggaagtggga agcggacgcc aagaaaaaac   4380
aggaaaccaa acgatgaaaa ctttggtcac ggccaaccag aaaggcggcg tcggcaagac   4440
ttcgacccct gtgcatcttg ccttcgactt tttcgagcgc ggcttgcggg ttgccgtgat   4500
cgacctggac ccccagggca atgcgtccta cacgctcaag gactttgcta ccggcctgca   4560
tgcaagcaag ctgttcggcg ctgtccctgc cggcggctgg accgaaaccg cacccgcagc   4620
cggcgacggc caggccgcgc gcctcgccct catcgagtcc aacccggtac tggcgaacgc   4680
cgaacggctg tcgctggacg acgcccgcga gctgttcggg gcgaacatca aggccctggc   4740
gaaccaaggc ttcgacgtgt gcctgatcga cacggccccg acccttggcg tcggcctggc   4800
ggccgccctc ttcgcggccg actatgtgct gtcccccatc gagcttgagg cgtacagcat   4860
ccagggcatc aagaagatgg tcacgaccat tgcgaacgtg cgccagaaga cgccaagct    4920 gcaattcctt ggcatggtgc ccagcaaggt cgatgcgcgg aatccgcgcc acgcgcgcca   4980
ccaagccgag ctgctggccg cgtaccccaa gatgatgatt ccggccaccg ttggcctgcg   5040
cagcagcatc gccgatgccc tcgcatccgg tgtgccggtc tggaagatca agaaaacggc   5100
cgcgcgcaag gcatcgaaag aggttcgcgc cctggctgat tacgtgttca cgaagatgga   5160
gatttcccaa tgactgcggc tcaagccaag accaccagtc gaggcgtgga ctcaaggctc   5220
tcgcgaatgg ctcgcgttgg aaactttcat tgacacttga ggggcaccgc agggaaattc   5280
tcgtccttgc gagaaccggc tatgtcgtgc tcgcatcga gcctgcgccc ttggcttgtc    5340
tcgcccctct ccgcgtcgct acggggcttc cagcgccttt ccgacgctca ccgggctggt   5400
tgccctcgcc gctgggctgg cggccgtcta tggccctgca aacgcgccag aaacgccgtc   5460
gaagccgtgt gcgagacacc gcggccgccg gcgttgtgga taccacgcgg aaaacttggc   5520
cctcactgac agatgagggg cggacgttga cacttgaggg gccgactcac ccggcgcggc   5580
gttgacagat gaggggcagg ctcgatttcg gccggcgacg tggagctggc cagcctcgca   5640
aatcggcgaa aacgcctgat tttacgcgag tttcccacag atgatgtgga caagcctggg   5700
gataagtgcc ctgcggtatt gacacttgag gggcgcgact actgacagat gaggggcgcg   5760
atccttgaca cttgagggc agagtgatga cagatgaggg gcgcacctat tgacatttga   5820
ggggctggga tccgggatta ccctgttatc cctagagctt ggcgtaatca tggtcatagc   5880
tgtttcctgt gtgaaattgt tatccgctca caattccaca caacatacga gccggaagca   5940
taaagtgtaa agcctggggt gcctaatgag tgagctaact cacattaatt gcgttgcgct   6000
cactgcccgc tttccagtcg ggaaacctgt cgtgccagct gcattaatga atcggccaac   6060
```

```
gcgcggggag aggcggtttg cgtattgggc gctcttccgc ttcctcgctc actgactcgc    6120
tgcgctcggt cgttcggctg cggcgagcgg tatcagctca ctcaaaggcg gtaatacggt    6180
tatccacaga atcaggggat aacgcaggaa agaacatgtg agcaaaaggc cagcaaaagg    6240
ccaggaaccg taaaaaggcc gcgttgctgg cgttttttcca taggctccgc cccctgacg    6300
agcatcacaa aaatcgacgc tcaagtcaga ggtggcgaaa cccgacagga ctataaagat    6360
accaggcgtt tccccctgga agctccctcg tgcgctctcc tgttccgacc ctgccgctta    6420
ccggatacct gtccgccttt ctcccttcgg gaagcgtggc gctttctcat agctcacgct    6480
gtaggtatct cagttcggtg taggtcgttc gctccaagct gggctgtgtg cacgaacccc    6540
ccgttcagcc cgaccgctgc gccttatccg gtaactatcg tcttgagtcc aacccggtaa    6600
gacacgactt atcgccactg gcagcagcca ctggtaacag gattagcaga gcgaggtatg    6660
taggcggtgc tacagagttc ttgaagtggt ggcctaacta cggctacact agaaggacag    6720
tatttggtat ctgcgctctg ctgaagccag ttaccttcgg aaaaagagtt ggtagctctt    6780
gatccggcaa acaaaccacc gctggtagcg gtggtttttt tgtttgcaag cagcagatta    6840
cgcgcagaaa aaaggatct caagaagatc ctttgatctt ttctacgggg tctgacgctc    6900
agtggaacga aaactcacgt taagggattt tggtcatgag attatcaaaa aggatcttca    6960
cctagatcct tttaaattaa aaatgaagtt ttaaatcaat ctaaagtata tatgagtaaa    7020
cttggtctga cagttaccaa tgcttaatca gtgaggcacc tatctcagcg atctgtctat    7080
ttcgttcatc catagttgcc tgactccccg tcgtgtagat aactacgata cgggagggct    7140
taccatctgg ccccagtgct gcaatgatac cgcgagaccc acgctcaccg gctccagatt    7200
tatcagcaat aaaccagcca gccggaaggg ccgagcgcag aagtggtcct gcaactttat    7260
ccgcctccat ccagtctatt aattgttgcc gggaagctag agtaagtagt tcgccagtta    7320
atagtttgcg caacgttgtt gccattgcta caggcatcgt ggtgtcacgc tcgtcgtttg    7380
gtatggcttc attcagctcc ggttcccaac gatcaaggcg agttacatga tcccccatgt    7440
tgtgcaaaaa agcggttagc tccttcggtc ctccgatcgt tgtcagaagt aagttggccg    7500
cagtgttatc actcatggtt atggcagcac tgcataattc tcttactgtc atgccatccg    7560
taagatgctt ttctgtgact ggtgagtact caaccaagtc attctgagaa tagtgtatgc    7620
ggcgaccgag ttgctcttgc ccggcgtcaa tacgggataa taccgcgcca catagcagaa    7680
ctttaaaagt gctcatcatt ggaaaacgtt cttcggggcg aaaactctca aggatcttac    7740
cgctgttgag atccagttcg atgtaaccca ctcgtgcacc caactgatct tcagcatctt    7800
ttactttcac cagcgtttct gggtgagcaa aaacaggaag gcaaaatgcc gcaaaaaagg    7860
gaataagggc gacacggaaa tgttaatac tcatactctt cctttttcaa tgggtgggc    7920
gaagaactcc agcatgagat cccgcgctg gaggatcatc cagccggcgt cccggaaaac    7980
gattccgaag cccaacctt catagaaggc ggcggtggaa tcgaaatctc gtgatggcag    8040
gttgggcgtc gcttggtcgg tcatttcgaa ccccagagtc cgctcagaa gaactcgtca    8100
agaaggcgat agaaggcgat gcgctgcgaa tcgggagcgg cgataccgta aagcacgagg    8160
aagcggtcag cccattcgcc gccaagctct tcagcaatat cacgggtagc caacgctatg    8220
tcctgatagc ggtccgccac acccagccgg ccacagtcga tgaatccaga aaagcggcca    8280
ttttccacca tgatattcgg caagcaggca tcgccatggg tcacgacgag atcctcgccg    8340
tcgggcatgc gcgccttgag cctggcgaac agttcggctg gcgcgagccc ctgatgctct    8400
tcgtccagat catcctgatc gacaagaccg gcttccatcc gagtacgtgc tcgctcgatg    8460
```

```
cgatgtttcg cttggtggtc aatgggcag gtagccggat caagcgtatg cagccgccgc     8520
attgcatcag ccatgatgga tactttctcg gcaggagcaa ggtgagatga caggagatcc     8580
tgccccggca cttcgcccaa tagcagccaa tcccttcccg cttcagtgac aacgtcgagc     8640
acagctgcgc aaggaacgcc cgtcgtggcc agccacgata gccgcgctgc ctcgtcctgc     8700
agttcattca gggcaccgga caggtcggtc ttgacaaaaa gaaccgggcg ccctgcgct     8760 gacagccgga acacgcggc atcagagcag ccgattgtct gttgtgccca gtcatagccg     8820
aatagcctct ccacccaagc ggccggagaa cctgcgtgca atccatcttg ttcaatcatg     8880
cgaaacgatc ctcatcctgt ctcttgatca gatcttgatc ccctgcgcca tcagatcctt     8940
ggcggcaaga aagccatcca gtttactttg cagggcttcc caaccttacc agagggcgcc     9000
ccagctggca attccggttc gcttgctgtc cataaaaccg cccagtctag ctatcgccat     9060
gtaagcccac tgcaagctac ctgctttctc tttgcgcttg cgttttccct tgtccagata     9120
gcccagtagc tgacattcat ccggggtcag caccgtttct gcggactggc tttctacgtg     9180
ttccgcttcc tttagcagcc cttgcgccct gagtgcttgc ggcagcgtga agctattatt     9240
gaagcattta tcaggggttat tgtctcatga gcggatacat atttgaatgt atttagaaaa     9300
ataaacaaat aggggttccg cgcacatttc cccgaaaagt gccacctgac gtctaagaaa     9360
ccattattat catgacatta acctataaaa ataggcgtat cacgaggcgc cctttcgtc     9419
```

<210> SEQ ID NO 5  
<211> LENGTH: 10733  
<212> TYPE: DNA  
<213> ORGANISM: Artificial  
<220> FEATURE:  
<223> OTHER INFORMATION: Derivative of pCURE11 based on vector pAKE604

<400> SEQUENCE: 5

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accataatcg gcattttctt ttgcgttttt atttgttaac tgttaattgt ccttgttcaa      240
ggatgctgtc tttgacaaca gatgttttct tgcctttgat gttcagcagg aagctaggcg      300
caaacgttga ttgtttgtct gcgtagaatc ctctgtttgt catatagctt gtaatcacga      360 cattgttttcc tttcgcttga ggtacagcga agtgtgagta agtaaaggtt acatcgttag      420
gatcaagatc cattttttaac acaaggccag ttttgttcag cggcttgtat gggccagtta      480
aagaattaga acataacca agcatgtaaa tatcgttaga cgtaatgccg tcaatcgtca      540
tttttgatcc gcgggagtca gtgaacagat accatttgcc gttcattttta aagacgttcg      600 cgcgttcaat ttcatctgtt actgtgttag atgcaatcag cggtttcatc actttttttca      660 gtgtgtaatc atcgtttagc tcaatcatac cgagagcgcc gtttgctaac tcagccgtgc      720
gttttttatc gctttgcaga agttttttgac tttcttgacg gaagaatgat gtgcttttgc      780
catagtatgc tttgttaaat aaagattctt cgccttggta gccatcttca gttccagtgt      840
ttgcttcaaa tactaagtat ttgtggcctt tatcttctac gtagtgagga tctctcagcg      900
tatggttgtc gcctgagctg tagttgcctt catcgatgaa ctgctgtaca ttttgatacg      960
tttttccgtc accgtcaaag attgatttat aatcctctac accgttgatg ttcaaagagc     1020
tgtctgatgc tgatacgtta acttgtgcag ttgtcagtgt tgtttgccg taatgtttac     1080
```

```
cggagaaatc agtgtagaat aaacggattt ttccgtcaga tgtaaatgtg gctgaacctg   1140
accattcttg tgtttggtct tttaggatag aatcatttgc atcgaatttg tcgctgtctt   1200
taaagacgcg gccagcgttt ttccagctgt caatagaagt ttcgccgact tttgataga   1260 acatgtaaat cgatgtgtca tccgcatttt taggatctcc ggctaatgca agacgatgt   1320 ggtagccgtg atagtttgcg acagtgccgt cagcgttttg taatggccag ctgtcccaaa   1380
cgtccaggcc ttttgcagaa gagatatttt taattgtgga cgaatcgaac tcaggaactt   1440
gatatttttc atttttttgc tgttcaggga tttgcagcat atcatggcgt gtaatatggg   1500
aaatgccgta tgtttcctta tatgctttt ggttcgtttc tttcgcaaac gcttgagttg   1560
cgcctcctgc cagcagtgcg gtagtaaagg ttaatactgt tgcttgtttt gcaaactttt   1620
tgatgttcat cgttcatgtc tccttttta tgtactgtgt tagcggtctg cttcttccag   1680
ccctcctgtt tgaagatggc aagttagtta cgcacaataa aaaagacct aaaatatgta   1740 aggggtgacg ccaaagtata cactttgccc tttacacatt ttaggtcttg cctgctttat   1800
cagtaacaaa cccgcgcgat ttacttttcg acctcattct attagactct cgtttggatt   1860
gcaactggtc tattttcctc ttttgtttga tagaaaatca taaaaggatt tgcagactac   1920
gggcctaaag aactaaaaaa tctatctgtt tcttttcatt ctctgtattt tttatagttt   1980
ctgttgcatg ggcataaagt tgccttttta atcacaattc agaaaatatc ataatatctc   2040
atttcactaa ataatagtga acggcaggta tatgtgatgg gttaaaaagg atcgatcctc   2100
tagctagagt cgatcttcgc cagcagggcg aggatcgtgg catcaccgaa ccgcgccgtg   2160
cgcgggtcgt cggtgagcca gagtttcagc aggccgccca ggcggcccag gtcgccattg   2220
atgcgggcca gctcgcggac gtgctcatag tccacgacgc ccgtgatttt gtagccctgg   2280
ccgacggcca gcaggtaggc cgacaggctc atgccggccg ccgccgcctt ttcctcaatc   2340
gctcttcgtt cgtctggaag gcagtacacc ttgataggtg ggctgcccctt cctggttggc   2400 ttggtttcat cagccatccg cttgccctca tctgttacgc cggcggtagc cggccagcct   2460
cgcagagcag gattcccgtt gagcaccgcc aggtgcgaat aagggacagt gaagaaggaa   2520
cacccgctcg cgggtgggcc tacttcacct atcctgcccg gctgacgccg ttggatacac   2580
caaggaaagt ctacacgaac cctttggcaa atcctgtat atcgtgcgaa aaaggatgga   2640
tataccgaaa aaatcgctat aatgaccccg aagcagggtt atgcagcgga aaagcgctgc   2700
ttccctgctg ttttgtggaa tatctaccga ctggaaacag gcaaatgcag gaaattactg   2760
aactgagggg acaggcgaga gacgatgcca aagagctaca ccgacgagct ggccgagtgg   2820
gttgaatccc gcgcggccaa gaagcgccgg cgtgatgagg ctgcggttgc gttcctggcg   2880
gtgagggcgg atgtcgatat gcgtaaggag aaaataccgc atcaggcgca tgcatatttg   2940
aatgtattta gaaaaataaa caaaaagagt tgtagaaaac gcaaaaaggc catccgtcag   3000 gatgccttc tgcttaattt gatgcctggc agtttatggc gggcgtcctg cccgccaccc   3060
tccgggccgt tgcttcgcaa cgttcaaatc cgctcccggc ggatttgtcc tactcaggag   3120
agcgttcacc gacaaacaac agataaaacg aaaggcccag tctttcgact gagcctttcg   3180
ttttatttga tgcctggcag ttccctactc tcgcatgggg agaccccaca ctaccatcgg   3240
cgctacggcg tttcacttct gagttcggca tggggtcagg tgggaccacc gcgctactgc   3300
cgccaggcaa attctgtttt atcagaccgc ttctgcgttc tgatttaatc tgtatcaggc   3360
tgaaaatctt ctctcatccg ccaaaacagc caagctcgcc attcgccatt caggctgcgc   3420
aactgttggg aagggcgatc ggtgcgggcc tcttcgctat tacgccagct ggcgaaaggg   3480
```

-continued

```
ggatgtgctg caaggcgatt aagttgggta acgccagggt tttcccagtc acgacgttgt    3540
aaaacgacgg ccagtgccaa gctcattacc ctgttatccc tacccggtga attcagcgca    3600
ttttcccgac cttaatgcgc ctcgcgctgt agcctcacgc ccacatatgt gctaatgtgg    3660
ttacgtgtat tttatggagg ttatccaatg agccgcctga caatcgacat gacggaccag    3720
cagcaccaga gcctgaaagc cctggccgcc ttgcagggca agaccattaa gcaatacgcc    3780
ctcgaacgtc tgttccccgg tgacgctgat gccgatcagg catggcagga actgaaaacc    3840
atgctgggga accgcatcaa cgatgggctt gccggcaagg tgtccaccaa gagcgtcggc    3900
gaaattcttg atgaagaact cagcggggat cgcgcttgac ggcctacatc ctcacggctg    3960
ggatctaagg acgagtttta gcggctaaag gtgttgacgt gcgagaaatg tttagctaaa    4020
cttctctcat gtgctggcgg ctgtcaccgc tatgttcaac caaggcgcgg agcaaattat    4080
gggtgttatc catgaagaaa cggcttaccg aaagccagtt ccaggaggcg atccagggc     4140 tggaagtggg gcagcagacc atcgagatag cgcggggcgt cttagtcgat gggaagccac    4200
aggcgacgtt cgcaacgtcg ctgggactga ccaggggcgc agtgtcgcaa gcggtgcatc    4260
gcgtgtgggc cgcgttcgag gacaagaact gcccgaggg gtacgcgcgg gtaacggcgg     4320
ttctgccgga acatcaggcg tacatcgtcc ggaagtggga agcggacgcc aagaaaaaac    4380
aggaaaccaa acgatgaaaa ctttggtcac ggccaaccag aaaggcggcg tcggcaagac    4440
ttcgacccct gtgcatcttg ccttcgactt tttcgagcgc ggcttgcggg ttgccgtgat    4500
cgacctggac ccccagggca atgcgtccta cacgctcaag gactttgcta ccggcctgca    4560
tgcaagcaag ctgttcggcg ctgtccctgc cggcggctgg accgaaaccg cacccgcagc    4620
cggcgacggc caggccgcgc gcctcgccct catcgagtcc aacccggtac tggcgaacgc    4680
cgaacggctg tcgctggacg acgcccgcga gctgttcggg gcgaacatca aggccctggc    4740
gaaccaaggc ttcgacgtgt gcctgatcga cacggcccg accttggcg tcggcctggc     4800 ggccgccctc ttcgcggccg actatgtgct gtcccccatc gagcttgagg cgtacagcat    4860
ccagggcatc aagaagatgg tcacgaccat tgcgaacgtg cgccagaaga acgcaagct    4920 gcaattcctt ggcatggtgc ccagcaaggt cgatgcgcgg aatccgcgcc acgcgcgcca    4980
ccaagccgag ctgctggccg cgtacccaa gatgatgatt ccggccaccg ttggcctgcg     5040
cagcagcatc gccgatgccc tcgcatccgg tgtgccggtc tggaagatca agaaaacggc    5100
cgcgcgcaag gcatcgaaag aggttcgcgc cctggctgat tacgtgttca cgaagatgga    5160
gatttcccaa tgactgcggc tcaagccaag accaccagtc gaggcgtgga ctcaaggctc    5220
tcgcgaatgg ctcgcgttgg aaactttcat tgacacttga ggggcaccgc agggaaattc    5280
tcgtccttgc gagaaccggc tatgtcgtgc tgcgcatcga gcctgcgccc ttggcttgtc    5340
tcgcccctct ccgcgtcgct acggggcttc cagcgccttt ccgacgctca ccgggctggt    5400
tgccctcgcc gctgggctgg cggccgtcta tggccctgca aacgcgccag aaacgccgtc    5460
gaagccgtgt gcgagacacc gcggccgccg cgttgtgga taccacgcgg aaaacttggc     5520
cctcactgac agatgagggg cggacgttga cacttgaggg gccgactcac ccggcgcggc    5580
gttgacagat gaggggcagg ctcgatttcg gccggcgacg tggagctggc cagcctcgca    5640
aatcggcgaa aacgcctgat tttacgcgag tttcccacag atgatgtgga caagcctggg    5700
gataagtgcc ctgcggtatt gacacttgag gggcgcgact actgacagat gaggggcgcg    5760
atccttgaca cttgaggggc agagtgatga cagatgaggg gcgcacctat tgacatttga    5820
```

```
ggggctggga tcaagcttcg tgatgagctg tcagtcgagc cgggcgggaa tgggtgacta      5880
gcgcaggcgc agccggagtc tgtcagccat tcacggctgg ccgccgccgg caggcgactt      5940
tgaggcccta acagccaagg caaatgcagc tggggttagg agatcataag aacgatgact      6000
tgccgaccct tgaaattcgc ggcctgcagg cttgcacctc gctcactgta tgcacgaacc      6060
cccgatcatc atccgtgagc gaccgtcgct cacaatctat gagctatccc tagctcatta      6120
tccatgagct aggttaggtc accctatgag ctaccccccc ttcatgagtt acccctagct      6180
catatgtgag agatatctca caggatttga gagataacgt gcacggatga gctacccatc      6240
gctcactaga tgagctaggg tatgcgtgaa ccatgaacga tatctaacaa atatgcacga      6300
tatcgatcac gcaattgcac cgtaggaggc ccaatggcca atgacaaaaa cgagatccgc      6360
gcctatgcgc agcctgccca cgcggtaca tgggtacaga ctgagcgcgc cggtcatgag       6420
gcatgggccg cactgactgc acaggcaccc cgcgcagcac agttgatgca catcctggta      6480
cagcacatgg ataagcaagg cgcgctgatc atcagccagg ccacgctggc caagctgatg      6540
gaaacgtccg tggccaccac caaacgcgcc atcgccatcc tgaccaagca caactggatc      6600
cagaccatca gtgtgggtgg ccaacggggt ggcacgctcg cttatgtagt gaacagccgg      6660
attgcatggg cggacaagag ggacaacctt cagtttgccc tgttcaacgc tcgggtactg      6720
gtttctaccg aggatcaggc tgatttgggc gatgccaagc tcaagcagct gccgacaatg      6780
gaagacggcg acattcagct acctgcgggt ccaggtatgg atccgcctgc gcaggagtcg      6840
ctggagggaa tgttgcctga tatgccctct attccccacg gtaactgagg caaggaccaa      6900
ggagggtgct ttatgtggaa gatcgaattc agtaaggatg accacggcat aggtcagttc      6960
ggcggcagtg tacgaatgaa tgatccagca ctgtggccgg ttacgccgga tacaaacgtt      7020
cccctcacgc cgctctgtac cttgaccgag gcactgttgc ccgtccggtt cttgccacct      7080
ggcatggcca tgaccgtgtt cattgcgccg aaccggaagg ccaacggctt caacttgtcg      7140
acgatccggg attaccctgt tatccctaga gcttggcgta atcatggtca tagctgtttc      7200
ctgtgtgaaa ttgttatccg ctcacaattc cacacaacat acgagccgga agcataaagt      7260
gtaaagcctg gggtgcctaa tgagtgagct aactcacatt aattgcgttg cgctcactgc      7320
ccgctttcca gtcgggaaac ctgtcgtgcc agctgcatta atgaatcggc caacgcgcgg      7380
ggagaggcgg tttgcgtatt gggcgctctt ccgcttcctc gctcactgac tcgctgcgct      7440
cggtcgttcg gctgcggcga gcggtatcag ctcactcaaa ggcggtaata cggttatcca      7500
cagaatcagg ggataacgca ggaaagaaca tgtgagcaaa aggccagcaa aaggccagga      7560
accgtaaaaa ggccgcgttg ctggcgtttt tccataggct ccgcccccct gacgagcatc      7620
acaaaaatcg acgctcaagt cagaggtggc gaaacccgac aggactataa agataccagg      7680
cgtttccccc tggaagctcc ctcgtgcgct ctcctgttcc gaccctgccg cttaccggat      7740
acctgtccgc ctttctccct tcgggaagcg tggcgctttc tcatagctca cgctgtaggt      7800
atctcagttc ggtgtaggtc gttcgctcca agctgggctg tgtgcacgaa ccccccgttc      7860
agcccgaccg ctgcgcctta tccggtaact atcgtcttga gtccaacccg gtaagacacg      7920
acttatcgcc actggcagca gccactggta acaggattag cagagcgagg tatgtaggcg      7980
gtgctacaga gttcttgaag tggtggccta actacggcta cactagaagg acagtatttg      8040
gtatctgcgc tctgctgaag ccagttacct tcggaaaaag agttggtagc tcttgatccg      8100
gcaaacaaac caccgctggt agcggtggtt ttttgtttg caagcagcag attacgcgca      8160
gaaaaaaagg atctcaagaa gatcctttga tcttttctac ggggtctgac gctcagtgga      8220
```

-continued

```
acgaaaactc acgttaaggg attttggtca tgagattatc aaaaaggatc ttcacctaga    8280
tccttttaaa ttaaaaatga agttttaaat caatctaaag tatatatgag taaacttggt    8340
ctgacagtta ccaatgctta atcagtgagg cacctatctc agcgatctgt ctatttcgtt    8400
catccatagt tgcctgactc cccgtcgtgt agataactac gatacgggag ggcttaccat    8460
ctggccccag tgctgcaatg ataccgcgag acccacgctc accggctcca gatttatcag    8520
caataaacca gccagccgga agggccgagc gcagaagtgg tcctgcaact ttatccgcct    8580
ccatccagtc tattaattgt tgccgggaag ctagagtaag tagttcgcca gttaatagtt    8640
tgcgcaacgt tgttgccatt gctacaggca tcgtggtgtc acgctcgtcg tttggtatgg    8700
cttcattcag ctccggttcc caacgatcaa ggcgagttac atgatccccc atgttgtgca    8760
aaaaagcggt tagctccttc ggtcctccga tcgttgtcag aagtaagttg gccgcagtgt    8820
tatcactcat ggttatggca gcactgcata attctcttac tgtcatgcca tccgtaagat    8880
gcttttctgt gactggtgag tactcaacca agtcattctg agaatagtgt atgcggcgac    8940
cgagttgctc ttgcccggcg tcaatacggg ataataccgc gccacatagc agaactttaa    9000
aagtgctcat cattggaaaa cgttcttcgg ggcgaaaact ctcaaggatc ttaccgctgt    9060
tgagatccag ttcgatgtaa cccactcgtg cacccaactg atcttcagca tcttttactt    9120
tcaccagcgt ttctgggtga gcaaaaacag gaaggcaaaa tgccgcaaaa aagggaataa    9180
gggcgacacg gaaatgttga atactcatac tcttcctttt tcaatggggt gggcgaagaa    9240
ctccagcatg agatccccgc gctggaggat catccagccg gcgtcccgga aaacgattcc    9300
gaagcccaac ctttcataga aggcggcggt ggaatcgaaa tctcgtgatg gcaggttggg    9360
cgtcgcttgg tcggtcattt cgaacccag agtcccgctc agaagaactc gtcaagaagg    9420
cgatagaagg cgatgcgctg cgaatcggga gcggcgatac cgtaaagcac gaggaagcgg    9480
tcagcccatt cgccgccaag ctcttcagca atatcacggg tagccaacgc tatgtcctga    9540
tagcggtccg ccacacccag ccggccacag tcgatgaatc cagaaaagcg gccattttcc    9600
accatgatat tcggcaagca ggcatcgcca tgggtcacga cgagatcctc gccgtcgggc    9660
atgcgcgcct tgagcctggc gaacagttcg gctggcgcga ccccgatg ctcttcgtcc    9720
agatcatcct gatcgacaag accggcttcc atccgagtac gtgctcgctc gatgcgatgt    9780
ttcgcttggt ggtcgaatgg gcaggtagcc ggatcaagcg tatgcagccg ccgcattgca    9840
tcagccatga tggatacttt ctcggcagga gcaaggtgag atgacaggag atcctgcccc    9900
ggcacttcgc ccaatagcag ccagtccctt cccgcttcag tgacaacgtc gagcacagct    9960
gcgcaaggaa cgcccgtcgt ggccagccac gatagccgcg ctgcctcgtc ctgcagttca    10020
ttcagggcac cggacaggtc ggtcttgaca aaaagaaccg ggcgcccctg cgctgacagc    10080
cggaacacgg cggcatcaga gcagccgatt gtctgttgtg cccagtcata gccgaatagc    10140
ctctccaccc aagcggccgg agaacctgcg tgcaatccat cttgttcaat catgcgaaac    10200
gatcctcatc ctgtctcttg atcagatctt gatccctgc gccatcagat ccttggcggc    10260
aagaaagcca tccagtttac tttgcagggc ttcccaacct taccagaggg cgccccagct    10320
ggcaattccg gttcgcttgc tgtccataaa accgcccagt ctagctatcg ccatgtaagc    10380
ccactgcaag ctacctgctt tctctttgcg cttgcgtttt ccttgtccca gatagcccag    10440
tagctgacat catccgggg tcagcaccgt ttctgcggac tggctttcta cgtgttccgc    10500
ttcctttagc agcccttgcg ccctgagtgc ttgcggcagc gtgaagctat tattgaagca    10560
```

-continued

```
tttatcaggg ttattgtctc atgagcggat acatatttga atgtatttag aaaaataaac    10620 aaatagggt tccgcgcaca tttccccgaa aagtgccacc tgacgtctaa gaaaccatta     10680
ttatcatgac attaacctat aaaaataggc gtatcacgag gcgccctttc gtc           10733
```

<210> SEQ ID NO 6
<211> LENGTH: 22
<212> TYPE: DNA
<213> ORGANISM: Artificial
<220> FEATURE:
<223> OTHER INFORMATION: Primer sequence

<400> SEQUENCE: 6

```
acattaaacg agagtaatcc cc                                              22
```

<210> SEQ ID NO 7
<211> LENGTH: 27
<212> TYPE: DNA
<213> ORGANISM: Artificial
<220> FEATURE:
<223> OTHER INFORMATION: Primer sequence

<400> SEQUENCE: 7

```
gtcgactgaa gatcagtcac accatcc                                         27
```

<210> SEQ ID NO 8
<211> LENGTH: 25
<212> TYPE: DNA
<213> ORGANISM: Artificial
<220> FEATURE:
<223> OTHER INFORMATION: Primer sequence

<400> SEQUENCE: 8

```
gctgacaagc tgtggtcagc agaac                                           25
```

<210> SEQ ID NO 9
<211> LENGTH: 26
<212> TYPE: DNA
<213> ORGANISM: Artificial
<220> FEATURE:
<223> OTHER INFORMATION: Primer sequence

<400> SEQUENCE: 9

```
tctagaggag gctcgatcca gtaaac                                          26
```

<210> SEQ ID NO 10
<211> LENGTH: 25
<212> TYPE: DNA
<213> ORGANISM: Artificial
<220> FEATURE:
<223> OTHER INFORMATION: Primer sequence

<400> SEQUENCE: 10

```
tctagaccat acgaaacggg aatgc                                           25
```

<210> SEQ ID NO 11
<211> LENGTH: 28
<212> TYPE: DNA
<213> ORGANISM: Artificial
<220> FEATURE:
<223> OTHER INFORMATION: Primer sequence

<400> SEQUENCE: 11

```
aagcttacat ccacaaacag acgataac                                        28
```

```
<210> SEQ ID NO 12
<211> LENGTH: 27
<212> TYPE: DNA
<213> ORGANISM: Artificial
<220> FEATURE:
<223> OTHER INFORMATION: Primer sequence

<400> SEQUENCE: 12
aagcttagga aaagtgaatg tggtcag                                          27

<210> SEQ ID NO 13
<211> LENGTH: 26
<212> TYPE: DNA
<213> ORGANISM: Artificial
<220> FEATURE:
<223> OTHER INFORMATION: Primer sequence

<400> SEQUENCE: 13
gaattccaac acacaccaga caagag                                           26

<210> SEQ ID NO 14
<211> LENGTH: 21
<212> TYPE: DNA
<213> ORGANISM: Artificial
<220> FEATURE:
<223> OTHER INFORMATION: Primer sequence

<400> SEQUENCE: 14
ggatccgcca gacgactcat a                                                21

<210> SEQ ID NO 15
<211> LENGTH: 23
<212> TYPE: DNA
<213> ORGANISM: Artificial
<220> FEATURE:
<223> OTHER INFORMATION: Primer sequence

<400> SEQUENCE: 15
ctcgagcgga tagccaattc aga                                              23

<210> SEQ ID NO 16
<211> LENGTH: 23
<212> TYPE: DNA
<213> ORGANISM: Artificial
<220> FEATURE:
<223> OTHER INFORMATION: Primer sequence

<400> SEQUENCE: 16
ctcgagggaa cggactggaa aca                                              23

<210> SEQ ID NO 17
<211> LENGTH: 25
<212> TYPE: DNA
<213> ORGANISM: Artificial
<220> FEATURE:
<223> OTHER INFORMATION: Primer sequence

<400> SEQUENCE: 17
ggatcccgtg tcggtaatga gtgaa                                            25

<210> SEQ ID NO 18
<211> LENGTH: 24
<212> TYPE: DNA
<213> ORGANISM: Artificial
<220> FEATURE:
<223> OTHER INFORMATION: Primer sequence
```

```
<400> SEQUENCE: 18
gctagcacca cgctgggttt actg                                            24

<210> SEQ ID NO 19
<211> LENGTH: 24
<212> TYPE: DNA
<213> ORGANISM: Artificial
<220> FEATURE:
<223> OTHER INFORMATION: Primer sequence

<400> SEQUENCE: 19
ggatccagcg agacaagcca gatt                                            24

<210> SEQ ID NO 20
<211> LENGTH: 26
<212> TYPE: DNA
<213> ORGANISM: Artificial
<220> FEATURE:
<223> OTHER INFORMATION: Primer sequence

<400> SEQUENCE: 20
ctggtacctc tcgcacagcg attttc                                          26

<210> SEQ ID NO 21
<211> LENGTH: 25
<212> TYPE: DNA
<213> ORGANISM: Artificial
<220> FEATURE:
<223> OTHER INFORMATION: Primer sequence

<400> SEQUENCE: 21
ttgctagccg cttgaggctt tctgc                                           25

<210> SEQ ID NO 22
<211> LENGTH: 24
<212> TYPE: DNA
<213> ORGANISM: Artificial
<220> FEATURE:
<223> OTHER INFORMATION: Primer sequence

<400> SEQUENCE: 22
ggatcccagc ccctcaaatg tcaa                                            24

<210> SEQ ID NO 23
<211> LENGTH: 24
<212> TYPE: DNA
<213> ORGANISM: Artificial
<220> FEATURE:
<223> OTHER INFORMATION: Primer sequence

<400> SEQUENCE: 23
ctcgaggcgt ggactcaagg ctct                                            24

<210> SEQ ID NO 24
<211> LENGTH: 24
<212> TYPE: DNA
<213> ORGANISM: Artificial
<220> FEATURE:
<223> OTHER INFORMATION: Primer sequence

<400> SEQUENCE: 24
gtcgactggt ggtcttggct tgag                                            24

<210> SEQ ID NO 25
<211> LENGTH: 24
```

```
<212> TYPE: DNA
<213> ORGANISM: Artificial
<220> FEATURE:
<223> OTHER INFORMATION: Primer sequence

<400> SEQUENCE: 25
agatctaagg acgagtttta gcgg                                              24

<210> SEQ ID NO 26
<211> LENGTH: 22
<212> TYPE: DNA
<213> ORGANISM: Artificial
<220> FEATURE:
<223> OTHER INFORMATION: Primer sequence

<400> SEQUENCE: 26
gaattcagcg cattttcccg ac                                                22

<210> SEQ ID NO 27
<211> LENGTH: 24
<212> TYPE: DNA
<213> ORGANISM: Artificial
<220> FEATURE:
<223> OTHER INFORMATION: Primer sequence

<400> SEQUENCE: 27
ggatcccagc cgtgaggatg tagg                                              24

<210> SEQ ID NO 28
<211> LENGTH: 10211
<212> TYPE: DNA
<213> ORGANISM: Artificial
<220> FEATURE:
<223> OTHER INFORMATION: Corrected sequence of pCURE 1 derived from
      pAKE604

<400> SEQUENCE: 28
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accataatcg gcattttctt ttgcgttttt atttgttaac tgttaattgt ccttgttcaa      240
ggatgctgtc tttgacaaca gatgttttct tgcctttgat gttcagcagg aagctaggcg      300
caaacgttga ttgtttgtct gcgtagaatc ctctgtttgt catatagctt gtaatcacga      360 cattgttttcc tttcgcttga ggtacagcga agtgtgagta agtaaaggtt acatcgttag      420
gatcaagatc cattttaac acaaggccag ttttgttcag cggcttgtat gggccagtta      480
aagaattaga aacataacca agcatgtaaa tatcgttaga cgtaatgccg tcaatcgtca      540
tttttgatcc gcgggagtca gtgaacagat accatttgcc gttcatttta aagacgttcg      600
cgcgttcaat ttcatctgtt actgtgttag atgcaatcag cggtttcatc acttttttca      660
gtgtgtaatc atcgtttagc tcaatcatac cgagagcgcc gtttgctaac tcagccgtgc      720
gttttttatc gctttgcaga agttttttgac tttcttgacg gaagaatgat gtgcttttgc      780
catagtatgc tttgttaaat aaagattctt cgccttggta gccatcttca gttccagtgt      840
ttgcttcaaa tactaagtat ttgtggcctt tatcttctac gtagtgagga tctctcagcg      900
tatggttgtc gcctgagctg tagttgcctt catcgatgaa ctgctgtaca ttttgatacg      960 ttttccgtc accgtcaaag attgattat aatcctctac accgttgatg ttcaaagagc     1020
tgtctgatgc tgatacgtta acttgtgcag ttgtcagtgt ttgtttgccg taatgtttac     1080
```

```
cggagaaatc agtgtagaat aaacggattt ttccgtcaga tgtaaatgtg gctgaacctg    1140
accattcttg tgtttggtct tttaggatag aatcatttgc atcgaatttg tcgctgtctt    1200
taaagacgcg gccagcgttt ttccagctgt caatagaagt ttcgccgact ttttgataga    1260
acatgtaaat cgatgtgtca tccgcatttt taggatctcc ggctaatgca aagacgatgt    1320
ggtagccgtg atagtttgcg acagtgccgt cagcgttttg taatggccag ctgtcccaaa    1380
cgtccaggcc ttttgcagaa gagatatttt taattgtgga cgaatcgaac tcaggaactt    1440 gatattttc attttttgc tgttcaggga tttgcagcat atcatggcgt gtaatatggg    1500
aaatgccgta tgtttcctta tatggctttt ggttcgtttc tttcgcaaac gcttgagttg    1560
cgcctcctgc cagcagtgcg gtagtaaagg ttaatactgt tgcttgtttt gcaaactttt    1620
tgatgttcat cgttcatgtc tccttttta tgtactgtgt tagcggtctg cttcttccag    1680
ccctcctgtt tgaagatggc aagttagtta cgcacaataa aaaagacct aaaatatgta    1740 aggggtgacg ccaaagtata cactttgccc tttacacatt ttaggtcttg cctgctttat    1800
cagtaacaaa cccgcgcgat ttacttttcg acctcattct attagactct cgtttggatt    1860
gcaactggtc tattttcctc ttttgtttga tagaaaatca taaaggatt tgcagactac    1920 gggcctaaag aactaaaaaa tctatctgtt tcttttcatt ctctgtattt tttatagttt    1980
ctgttgcatg gcataaagt tgccttttta atcacaattc agaaaatatc ataatatctc    2040
atttcactaa ataatagtga acggcaggta tatgtgatgg gttaaaaagg atcgatcctc    2100
tagctagagt cgatcttcgc cagcagggcg aggatcgtgg catcaccgaa ccgcgccgtg    2160
cgcgggtcgt cggtgagcca gagtttcagc aggccgccca ggcggcccag gtcgccattg    2220
atgcgggcca gctcgcggac gtgctcatag tccacgacgc ccgtgatttt gtagccctgg    2280
ccgacggcca gcaggtaggc cgacaggctc atgccggccg ccgccgcctt ttcctcaatc    2340
gctcttcgtt cgtctggaag gcagtacacc ttgataggtg ggctgcccctt cctggttggc    2400 ttggtttcat cagccatccg cttgccctca tctgttacgc cggcggtagc cggccagcct    2460
cgcagagcag gattcccgtt gagcaccgcc aggtgcgaat aagggacagt gaagaaggaa    2520
cacccgctcg cgggtgggcc tacttcacct atcctgcccg gctgacgccg ttggatacac    2580
caaggaaagt ctacacgaac cctttggcaa aatcctgtat atcgtgcgaa aaaggatgga    2640
tataccgaaa aaatcgctat aatgaccccg aagcagggtt atgcagcgga aaagcgctgc    2700
ttccctgctg ttttgtggaa tatctaccga ctggaaacag gcaaatgcag gaaattactg    2760
aactgagggg acaggcgaga gacgatgcca aagagctaca ccgacgagct ggccgagtgg    2820
gttgaatccc gcgcggccaa gaagcgccgg cgtgatgagg ctgcggttgc gttcctggcg    2880
gtgagggcgg atgtcgatat gcgtaaggag aaaataccgc atcaggcgca tgcatatttg    2940
aatgtattta gaaaaataaa caaaagagt ttgtagaaac gcaaaaggc catccgtcag    3000 gatgccttc tgcttaattt gatgcctggc agtttatggc gggcgtcctg cccgccaccc    3060
tccgggccgt tgcttcgcaa cgttcaaatc cgctcccggc ggatttgtcc tactcaggag    3120
agcgttcacc gacaaacaac agataaaacg aaaggcccag tctttcgact gagcctttcg    3180
ttttatttga tgcctggcag ttccctactc tcgcatgggg agaccccaca ctaccatcgg    3240
cgctacggcg tttcacttct gagttcggca tggggtcagg tgggaccacc gcgctactgc    3300
cgccaggcaa attctgtttt atcagaccgc ttctgcgttc tgatttaatc tgtatcaggc    3360
tgaaaatctt ctctcatccg ccaaaacagc caagctcgcc attcgccatt caggctgcgc    3420
```

-continued

```
aactgttggg aagggcgatc ggtgcgggcc tcttcgctat acgccagct ggcgaaaggg      3480
ggatgtgctg caaggcgatt aagttgggta acgccagggt tttcccagtc acgacgttgt    3540
aaaacgacgg ccagtgccaa gctcattacc ctgttatccc tacccggtga attcactagt    3600
gattattcca acacacacca gacaagagag ctgcgtggta gtttcatggc cttcttctcc    3660
ttgcgcaaag cgcggtaaga ggctatcctg atgttgtcta agcatgcagg ggcctcgtgg    3720
gttaatgaaa aattaactac ggggcttttg tccttctgcc acacaacacg gtaacaaacc    3780
accttcacgt catgaggcag aaagcctcaa gcgccgggca catcatagcc catataccag    3840
cacgctgacc acattcactt ttcctaagct tacatccaca aacagacgat aacggctctc    3900
tcttttatag gtgtaaacct taaactgcat ttcaccagtc cctgttctcg tcagcaaaag    3960
agccgttcat ttcaataaac cgggcgacct cagccatccc ttcctgattt tccgcttttcc   4020
agcgttcggc acgcagacga cgggcttcat tctgcatggt tgtgcttacc agaccggaga    4080
tattgacatc atatgccttg agcaactgat agctgtcgct gtcaactgtc actgtaatac    4140
gctgcttcat agcacacctc ttttgacat acttcgggta tacatatcag tatatattct     4200
tatgccgcaa aaatcagcgc gcaaatacgc atactattat ctggctttta gtaagcctta   4260
tgtattttac ctttcgttat gttaaccaat aaaaattaaa atctgcctta taaaaacaaa    4320
gcgtaattac cgcattcccg tttcgtatgg tctagaggag gctcgatcca gtaaacagat    4380
ccatgaatga tcaacaaagg atccattaaa gatccccata ccgctgcaaa ccttgtcact    4440
catgggccgg gaccacgatc acataagcag tggcatgtta ctgataaact gtaacatgct    4500
aatgataagc tgtattcagt aatccatata ctgaagtaag ttaatgacat aaactatggt    4560
cagtacgcca gactcagctg ttaaatacag gctgcaggtt tttcttcagt cagttagcgg    4620
ggctctgaca cacgatttgc tgtttattct tttactgtcc acaggcagga ggctttctgg    4680
aaaacgaaaa ttcagacatc aaaaaactgt tcggcgaggt ggataagtcg tccggtgagc    4740
tggtgacact gacaccaaac aataacaaca ccgtacaacc tgtggcgctg atgcgtctgg    4800
gcgttttgt accgaccctt aaatcactga agaacagtaa aaaaaataca ctgtcacgta      4860
ctgatgccac ggaagagctg acacgtcttt ccctggcccg tgctgaggga ttcgataagg    4920
ttgagatcac cggcccccgc ctggatatgg ataacgattt caagacctgg gtggggatca    4980
ttcattcctt tgcccgccat aacgtaattg gtgacaaagt tgaactgcct tttgtcgagt    5040
ttgcaaaact gtgtggtata ccttcaagcc agtcatcacg caggctgcgt gagcgcatca    5100
gccttccct gaaacgcatt gccggtaccg tgatctcctt tcccgcacc gatgagaagc       5160
acacccggga atacatcacc catctggtac agtcagccta ctacgatact gaacgggata    5220
ttgttcagtt acaggctgat ccccgccttt ttgaactgta ccagtttgac agaaaggtcc    5280
ttctccagct taaggcgatt aatgccctga agcgacggga gtccgcccag gcactctaca    5340
cctttataga gagcctgccc cgggatccgg caccggtatc gctggcgcgg ctgcgtgcac    5400
gcctcaatct gaagtctcct gtattttccc agaaccagac ggtcagacgg gcaatggagc    5460
agctgcgcga gattggatat cttgattaca cggagatcca gcggggcgg acaaaactct     5520
tctgcattca ctaccggcgt ccccggttaa agcaccgaa tgatgagagt aaggaaaatc     5580
cgttgccacc ttcacctgcg gaaaaagtca gtccggagat ggcggagaag cttgccctgc    5640
ttgagaaact gggcatcacg ctggatgacc tggaaaaact cttcaaatcc cgctgaacat    5700
aaactgtagt cagtgaagag tgttccttta ctgactacag cttatattat caggtgcagt    5760
gagtggtctg ctcactgcag tttatattca gtttcctgca gtgctgccag tagctgagct    5820
```

```
gtcatctgcc ggtcccttac gtgagtcacc ccgtaacctg atgctgaggc attgctccct      5880
tcataaaaca tgacttactc actacagctt atatacatgc tccagcttat gttatgtctg      5940
ttctgctgac cacagcttgt cgactgaaga tcagtcacac catcctgcac ttacaatgcg      6000
cagaaggagc gagcacagaa agaagtcttg aacttttccg agcatataac tatactcccc      6060
gcatagctga attgttggct atacggttta agtgggcccc ggtaatcttc tcagtcgcca      6120
aactttctga agattatcgg ggttttttgct tttctggctc ctgtaaatcc acatcagaac      6180
cagttccctg ccaccttacg gcgtggccag ccacaaaatt ccttaaacga tcagtaatct      6240
agcactaatc ttctgaacac tcaagaatgt aagcccatca tcacacacat cgttttttgcg      6300 cttcactttt tatcagtgcg gtcagaactt cagcctgagt caggccatct tcatgacaca      6360
tttgcatgag catggcctta tactttggtt caagaaatac ttttacttcc ttgaacgaag      6420
ctcttttacg ggccactgat aatctttgtt tctctgcatc agaaagcgga ttccccttc      6480 tgtatgctcg ttttgcgcca gatgaggaag tcactgcatt ttctgtctgc gacatctcgc      6540
ctcctcaata cttaaacagg gatcgtttcg cagaggatac tacagttttt tgaaatcagc      6600
gacttgagaa ttgtgacgaa gatccgggat taccctgtta tccctagagc ttggcgtaat      6660
catggtcata gctgtttcct gtgtgaaatt gttatccgct cacaattcca cacaacatac      6720
gagccggaag cataaagtgt aaagcctggg gtgcctaatg agtgagctaa ctcacattaa      6780
ttgcgttgcg ctcactgccc gctttccagt cgggaaacct gtcgtgccag ctgcattaat      6840
gaatcggcca acgcgcgggg agaggcggtt tgcgtattgg gcgctcttcc gcttcctcgc      6900
tcactgactc gctgcgctcg gtcgttcggc tgcggcgagc ggtatcagct cactcaaagg      6960
cggtaatacg gttatccaca gaatcagggg ataacgcagg aaagaacatg tgagcaaaag      7020
gccagcaaaa ggccaggaac cgtaaaaagg ccgcgttgct ggcgtttttc cataggctcc      7080 gccccccctga cgagcatcac aaaaatcgac gctcaagtca gaggtggcga acccgacag      7140 gactataaag ataccaggcg tttccccctg gaagctccct cgtgcgctct cctgttccga      7200
ccctgccgct taccggatac ctgtccgcct ttctcccttc gggaagcgtg gcgctttctc      7260
atagctcacg ctgtaggtat ctcagttcgg tgtaggtcgt tcgctccaag ctgggctgtg      7320
tgcacgaacc ccccgttcag cccgaccgct gcgccttatc cggtaactat cgtcttgagt      7380
ccaacccggt aagacacgac ttatcgccac tggcagcagc cactggtaac aggattagca      7440
gagcgaggta tgtaggcggt gctacagagt tcttgaagtg gtggcctaac tacggctaca      7500
ctagaaggac agtatttggt atctgcgctc tgctgaagcc agttaccttc ggaaaaagag      7560
ttggtagctc ttgatccggc aaacaaacca ccgctggtag cggtggtttt tttgtttgca      7620
agcagcagat tacgcgcaga aaaaaggat ctcaagaaga tcctttgatc ttttctacgg      7680
ggtctgacgc tcagtggaac gaaaactcac gttaagggat tttggtcatg agattatcaa      7740
aaaggatctt cacctagatc cttttaaatt aaaaatgaag ttttaaatca atctaaagta      7800
tatatgagta aacttggtct gacagttacc aatgcttaat cagtgaggca cctatctcag      7860
cgatctgtct atttcgttca tccatagttg cctgactccc cgtcgtgtag ataactacga      7920
tacgggaggg cttaccatct ggccccagtg ctgcaatgat accgcgagac ccacgctcac      7980
cggctccaga tttatcagca ataaaccagc cagccggaag ggccgagcgc agaagtggtc      8040
ctgcaacttt atccgcctcc atccagtcta ttaattgttg ccgggaagct agagtaagta      8100
gttcgccagt taatagtttg cgcaacgttg ttgccattgc tacaggcatc gtggtgtcac      8160
```

-continued

```
gctcgtcgtt tggtatggct tcattcagct ccggttccca acgatcaagg cgagttacat    8220
gatcccccat gttgtgcaaa aaagcggtta gctccttcgg tcctccgatc gttgtcagaa    8280
gtaagttggc cgcagtgtta tcactcatgg ttatggcagc actgcataat tctcttactg    8340
tcatgccatc cgtaagatgc ttttctgtga ctggtgagta ctcaaccaag tcattctgag    8400
aatagtgtat gcggcgaccg agttgctctt gcccggcgtc aatacgggat aataccgcgc    8460
cacatagcag aactttaaaa gtgctcatca ttggaaaacg ttcttcgggg cgaaaactct    8520
caaggatctt accgctgttg agatccagtt cgatgtaacc cactcgtgca cccaactgat    8580
cttcagcatc ttttactttc accagcgttt ctgggtgagc aaaaacagga aggcaaaatg    8640
ccgcaaaaaa gggaataagg gcgacacgga aatgttgaat actcatactc ttcctttttc    8700
aatggggtgg gcgaagaact ccagcatgag atccccgcgc tggaggatca tccagccggc    8760
gtcccggaaa acgattccga agcccaacct ttcatagaag gcggcggtgg aatcgaaatc    8820
tcgtgatggc aggttgggcg tcgcttggtc ggtcatttcg aacccagag tcccgctcag    8880 aagaactcgt caagaaggcg atagaaggcg atgcgctgcg aatcgggagc ggcgataccg    8940
taaagcacga ggaagcggtc agcccattcg ccgccaagct cttcagcaat atcacgggta    9000
gccaacgcta tgtcctgata gcggtccgcc acacccagcc ggccacagtc gatgaatcca    9060
gaaaagcggc cattttccac catgatattc ggcaagcagg catcgccatg ggtcacgacg    9120
agatcctcgc cgtcgggcat gcgcgccttg agcctggcga acagttcggc tggcgcgagc    9180
ccctgatgct cttcgtccag atcatcctga tcgacaagac cggcttccat ccgagtacgt    9240
gctcgctcga tgcgatgttt cgcttggtgg tcgaatgggc aggtagccgg atcaagcgta    9300
tgcagccgcc gcattgcatc agccatgatg gatactttct cggcaggagc aaggtgagat    9360
gacaggagat cctgccccgg cacttcgccc aatagcagcc agtcccttcc cgcttcagtg    9420
acaacgtcga gcacagctgc gcaaggaacg cccgtcgtgg ccagccacga tagccgcgct    9480
gcctcgtcct gcagttcatt cagggcaccg gacaggtcgg tcttgacaaa aagaaccggg    9540
cgcccctgcg ctgacagccg aacacggcg gcatcagagc agccgattgt ctgttgtgcc    9600
cagtcatagc cgaatagcct ctccacccaa gcggccggag aacctgcgtg caatccatct    9660
tgttcaatca tgcgaaacga tcctcatcct gtctcttgat cagatcttga tccctgcgc    9720 catcagatcc ttggcggcaa gaaagccatc cagtttactt tgcagggctt cccaacctta    9780
ccagagggcg ccccagctgg caattccggt tcgcttgctg tccataaaac cgcccagtct    9840
agctatcgcc atgtaagccc actgcaagct acctgctttc tctttgcgct tgcgttttcc    9900
cttgtccaga tagcccagta gctgacattc atccggggtc agcaccgttt ctgcggactg    9960
gctttctacg tgttccgctt cctttagcag cccttgcgcc ctgagtgctt gcggcagcgt    10020
gaagctatta ttgaagcatt tatcagggtt attgtctcat gagcggatac atatttgaat    10080
gtatttagaa aaataaacaa ataggggttc cgcgcacatt tccccgaaaa gtgccacctg    10140
acgtctaaga aaccattatt atcatgacat taacctataa aaataggcgt atcacgaggc    10200
gccctttcgt c                                                         10211
```

<210> SEQ ID NO 29
<211> LENGTH: 12016
<212> TYPE: DNA
<213> ORGANISM: Artificial
<220> FEATURE:
<223> OTHER INFORMATION: Corrected sequence of pCURE2 derived from pCURE1 and based on pAKE604

```
<400> SEQUENCE: 29
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataatcg gcattttctt ttgcgttttt atttgttaac tgttaattgt ccttgttcaa     240
ggatgctgtc tttgacaaca gatgttttct tgcctttgat gttcagcagg aagctaggcg     300
caaacgttga ttgtttgtct gcgtagaatc ctctgtttgt catatagctt gtaatcacga     360
cattgtttcc tttcgcttga ggtacagcga agtgtgagta agtaaaggtt acatcgttag     420
gatcaagatc cattttaac acaaggccag ttttgttcag cggcttgtat gggccagtta     480
aagaattaga aacataacca agcatgtaaa tatcgttaga cgtaatgccg tcaatcgtca     540
tttttgatcc gcgggagtca gtgaacagat accatttgcc gttcatttta aagacgttcg     600
cgcgttcaat ttcatctgtt actgtgttag atgcaatcag cggtttcatc acttttttca     660
gtgtgtaatc atcgtttagc tcaatcatac cgagagcgcc gtttgctaac tcagccgtgc     720
gttttttatc gctttgcaga agttttgac tttcttgacg gaagaatgat gtgcttttgc     780
catagtatgc tttgttaaat aaagattctt cgccttggta gccatcttca gttccagtgt     840
ttgcttcaaa tactaagtat ttgtggcctt tatcttctac gtagtgagga tctctcagcg     900
tatggttgtc gcctgagctg tagttgcctt catcgatgaa ctgctgtaca ttttgatacg     960
tttttccgtc accgtcaaag attgatttat aatcctctac accgttgatg ttcaaagagc    1020
tgtctgatgc tgatacgtta acttgtgcag ttgtcagtgt ttgtttgccg taatgtttac    1080
cggagaaatc agtgtagaat aaacggattt ttccgtcaga tgtaaatgtg gctgaacctg    1140
accattcttg tgtttggtct tttaggatag aatcatttgc atcgaatttg tcgctgtctt    1200
taaagacgcg gccagcgttt ttccagctgt caatagaagt ttcgccgact ttttgataga    1260
acatgtaaat cgatgtgtca tccgcatttt taggatctcc ggctaatgca aagacgatgt    1320
ggtagccgtg atagtttgcg acagtgccgt cagcgttttg taatggccag ctgtcccaaa    1380
cgtccaggcc ttttgcagaa gagatatttt taattgtgga cgaatcgaac tcaggaactt    1440 gatattttc attttttgc tgttcaggga tttgcagcat atcatggcgt gtaatatggg    1500
aaatgccgta tgtttcctta tatggctttt ggttcgtttc tttcgcaaac gcttgagttg    1560
cgcctcctgc cagcagtgcg gtagtaaagg ttaatactgt tgcttgtttt gcaaactttt    1620
tgatgttcat cgttcatgtc tccttttta tgtactgtgt tagcggtctg cttcttccag    1680
ccctcctgtt tgaagatggc aagttagtta cgcacaataa aaaagacct aaaatatgta    1740 agggtgacg ccaaagtata cactttgccc tttacacatt ttaggtcttg cctgctttat    1800
cagtaacaaa cccgcgcgat ttacttttcg acctcattct attagactct cgtttggatt    1860
gcaactggtc tattttcctc ttttgtttga tagaaaatca taaaggatt tgcagactac    1920 gggcctaaag aactaaaaaa tctatctgtt tcttttcatt ctctgtattt tttatagttt    1980
ctgttgcatg gcataaagt tgcctttta atcacaattc agaaaatatc ataatatctc    2040
atttcactaa ataatagtga acggcaggta tatgtgatgg gttaaaaagg atcgatcctc    2100
tagctagagt cgatcttcgc cagcagggcg aggatcgtgg catcaccgaa ccgcgccgtg    2160
cgcgggtcgt cggtgagcca gagtttcagc aggccgccca gcggcccag tcgccattg    2220 atgcgggcca gctcgcggac gtgctcatag tccacgacgc ccgtgatttt gtagccctgg    2280
ccgacggcca gcaggtaggc cgacaggctc atgccggccg ccgccgcctt ttcctcaatc    2340
```

```
gctcttcgtt cgtctggaag gcagtacacc ttgataggtg ggctgccctt cctggttggc   2400 ttggttttcat cagccatccg cttgccctca tctgttacgc cggcggtagc cggccagcct   2460
cgcagagcag gattcccgtt gagcaccgcc aggtgcgaat aagggacagt gaagaaggaa   2520
cacccgctcg cgggtgggcc tacttcacct atcctgcccg gctgacgccg ttggatacac   2580
caaggaaagt ctacacgaac cctttggcaa atcctgtat atcgtgcgaa aaggatgga   2640 tataccgaaa aaatcgctat aatgaccccg aagcagggtt atgcagcgga aaagcgctgc   2700
ttccctgctg ttttgtggaa tatctaccga ctggaaacag gcaaatgcag gaaattactg   2760
aactgagggg acaggcgaga gacgatgcca agagctaca ccgacgagct ggccgagtgg   2820
gttgaatccc gcgcggccaa gaagcgccgg cgtgatgagg ctgcggttgc gttcctggcg   2880
gtgagggcga atgtcgatat gcgtaaggag aaaataccgc atcaggcgca tgcatatttg   2940
aatgtattta gaaaaataaa caaaaagagt ttgtagaaac gcaaaaaggc catccgtcag   3000
gatggccttc tgcttaattt gatgcctggc agtttatggc gggcgtcctg cccgccaccc   3060
tccgggccgt tgcttcgcaa cgttcaaatc cgctcccggc ggatttgtcc tactcaggag   3120
agcgttcacc gacaaacaac agataaaacg aaaggcccag tctttcgact gagcctttcg   3180
ttttatttga tgcctggcag ttccctactc tcgcatgggg agaccccaca ctaccatcgg   3240
cgctacggcg tttcacttct gagttcggca tggggtcagg tggaccacc gcgctactgc   3300 cgccaggcaa attctgtttt atcagaccgc ttctgcgttc tgatttaatc tgtatcaggc   3360
tgaaaatctt ctctcatccg ccaaaacagc caagctcgcc attcgccatt caggctgcgc   3420
aactgttggg aagggcgatc ggtgcgggcc tcttcgctat tacgccagct ggcgaaaggg   3480
ggatgtgctg caaggcgatt aagttgggta acgccagggt tttcccagtc acgacgttgt   3540
aaaacgacgg ccagtgccaa gctcattacc ctgttatccc tacccggtga attcactagt   3600
gattattcca acacacacca gacaagagag ctgcgtggta gtttcatggc cttcttctcc   3660
ttgcgcaaag cgcggtaaga ggctatcctg atgttgtcta agcatgcagg ggcctcgtgg   3720
gttaatgaaa aattaactac ggggcttttg tccttctgcc acacaacacg gtaacaaacc   3780
accttcacgt catgaggcag aaagcctcaa gcgccgggca catcatagcc catataccag   3840
cacgctgacc acattcactt ttcctaagct tacatccaca aacagacgat aacggctctc   3900
tcttttatag gtgtaaacct taaactgcat ttcaccagtc cctgttctcg tcagcaaaag   3960
agccgttcat ttcaataaac cgggcgacct cagccatccc ttcctgattt tccgctttcc   4020
agcgttcggc acgcagacga cgggcttcat tctgcatggt tgtgcttacc agaccggaga   4080
tattgacatc atatgccttg agcaactgat agctgtcgct gtcaactgtc actgtaatac   4140
gctgcttcat agcacacctc tttttgacat acttcgggta tacatatcag tatatattct   4200
tatgccgcaa aaatcagcgc gcaaatacgc atactattat ctggctttta gtaagcctta   4260 tgtatttttac ctttcgttat gttaaccaat aaaaattaaa atctgcctta taaaacaaa   4320 gcgtaattac cgcattcccg tttcgtatgg tctagcacca cgctgggttt actgtttggt   4380
tgaaagttat attttttatta aacattgtgc gttaaagcct ggtgtgtttt tttagtggat   4440
gttatattta aatataactt ttatggaggt gaagaatgca taccacccga ctgaagaggg   4500
ttggcggctc agttatgctg accgtcccac cggcactgct gaatgcgctg tctctgggca   4560
cagataatga agttggcatg gtcattgata atggccggc gattgttgag ccgtacagac   4620
gcccgcaata ttcactggct gagctactgg cacagtgtga tccgaatgct gaaatatcag   4680
```

```
ctgaagaacg agaatggctg gatgcaccgg cgactggtca ggaggaaatc tgacatggaa    4740
agaggggaaa tctggcttgt ctcgctggat cgggtacctc tcgcacagcg attttcgtgt    4800
cagataagtg aatatcaaca gtgtgagaca cacgatcaac acacaccaga caagggaact    4860
tcgtggtagt ttcatggcct tcttctcctt gcgcaaagcg cggtaagagg ctatcctgat    4920
gtggactaga catagggatg cctcgtggtg gttaatgaaa attaacttac tacggggcta    4980
tcttcttttct gccacacaac acggcaacaa accaccttca cgtcatgagg cagaaagcct    5040
caagcggcta gaggaggctc gatccagtaa acagatccat gaatgatcaa caaaggatcc    5100
attaaagatc cccataccgc tgcaaacctt gtcactcatg gccgggacc acgatcacat    5160
aagcagtggc atgttactga taaactgtaa catgctaatg ataagctgta ttcagtaatc    5220
catatactga agtaagttaa tgacataaac tatggtcagt acgccagact cagctgttaa    5280
atacaggctg caggtttttc ttcagtcagt tagcggggct ctgacacacg atttgctgtt    5340
tattctttta ctgtccacag gcaggaggct ttctggaaaa cgaaaattca gacatcaaaa    5400
aactgttcgg cgaggtggat aagtcgtccg gtgagctggt gacactgaca ccaaacaata    5460
acaacaccgt acaacctgtg gcgctgatgc gtctgggcgt ttttgtaccg acccttaaat    5520
cactgaagaa cagtaaaaaa aatacactgt cacgtactga tgccacggaa gagctgacac    5580
gtctttccct ggcccgtgct gagggattcg ataaggttga gatcaccggc cccgcctgg    5640
atatggataa cgatttcaag acctgggtgg ggatcattca ttcctttgcc cgccataacg    5700
taattggtga caaagttgaa ctgccttttg tcgagtttgc aaaactgtgt ggtataccctt    5760
caagccagtc atcacgcagg ctgcgtgagc gcatcagccc ttccctgaaa cgcattgccg    5820
gtaccgtgat ctccttttcc cgcaccgatg agaagcacac ccgggaatac atcacccatc    5880
tggtacagtc agcctactac gatactgaac gggatattgt tcagttacag gctgatcccc    5940
gccttttga actgtaccag tttgacagaa aggtccttct ccagcttaag gcgattaatg    6000
ccctgaagcg acgggagtcc gcccaggcac tctacacctt tatagagagc ctgccccggg    6060
atccggcacc ggtatcgctg gcgcggctgc gtgcacgcct caatctgaag tctcctgtat    6120
tttcccagaa ccagacggtc agacgggcaa tggagcagct gcgcgagatt ggatatcttg    6180
attacacgga gatccagcgg gggcggacaa aactcttctg cattcactac cggcgtcccc    6240
ggttaaaagc accgaatgat gagagtaagg aaaatccgtt gccaccttca cctgcggaaa    6300
aagtcagtcc ggagatggcg gagaagcttg ccctgcttga gaaactgggc atcacgctgg    6360
atgacctgga aaaactcttc aaatcccgct gaacataaac tgtagtcagt gaagagtgtt    6420
cctttactga ctacagctta tattatcagg tgcagtgagt ggtctgctca ctgcagttta    6480
tattcagttt cctgcagtgc tgccagtagc tgagctgtca tctgccggtc ccttacgtga    6540
gtcaccccgt aacctgatgc tgaggcattg ctccccttcat aaaacatgac ttactcacta    6600
cagcttatat acatgctcca gcttatgtta tgtctgttct gctgaccaca gcttgtcgag    6660
ggaacggact ggaaacagac gtactgacat cccaggaaac gatcttgaaa cgtaaaccgt    6720
gcgccaacac aggttacgtt cataaagtaa gtcgctgatt ttagaaatct gtagtattct    6780
ctgcaaacga tctaggtttg atccttgagg agacagagat gtcgcagatt gaaaatgcag    6840
taacttcctc atcgaaacgc atttacagaa agggtaatcc cttatcttcc gctgagaaga    6900
agagattatc tatttcacga aaaaagacga cgcataaaga gctcaatgtt ttcatacaaa    6960
acatacataa agaagcttg cagcagcttt gtgaagagac tggaactact caggctcaaa    7020
tgattgagct actaattgaa cgggaaatgg ctaaaagagc ctgagataag aaggtgaatg    7080
```

```
agtaactttc ttgatcgtct cgtcagtgag tgttagattg ctgatcgtct aaagaatttt    7140
gatggctggc cacgccgtaa ggtggcaggg aactggttct gatgaggtgc ctacccggga    7200
ccagaaaagc aaaaacccg ataatcttct catttcttgg cgggaacgaa agattaacgg     7260
ggcctactta aactgtatag ccaccaatca ggctatgcag ggagtatagt tttatgctca    7320
gaaaatttca atacttgttt ctgtggcatt tactccttcc gtgcattgta agtgcaggca    7380
gaagtgactg acacccgaac actgttcact cattaccgac aggggatccg ccagacgact    7440
catatcgtat tttccttccg cgatatcact tccatgacga caggatagtc tgagggttat    7500
ctgtcacaga tttgagggtg gttcgtcaca tttgttctga cctactgagg gtaatttgtc    7560
acagttttgc tgtttccttc agcctgcatg gattttctca tacttttga actgtaattt     7620 ttaaggaagc caaatttgag ggcagtttgt cacagttgat ttccttctct ttcccttcgt    7680
catgtgacct gatatcgggg gttagttcgt catcattgat gagggttgat tatcacagtt    7740
tattactctg aattggctat ccgctcgact gaagatcagt cacaccatcc tgcacttaca    7800
atgcgcagaa ggagcgagca cagaaagaag tcttgaactt ttccgagcat ataactatac    7860
tccccgcata gctgaattgt tggctatacg gtttaagtgg gccccggtaa tcttctcagt    7920
cgccaaactt tctgaagatt atcggggttt ttgcttttct ggctcctgta aatccacatc    7980
agaaccagtt ccctgccacc ttacggcgtg gccagccaca aaattcctta aacgatcagt    8040
aatctagcac taatcttctg aacactcaag aatgtaagcc catcatcaca cacatcgttt    8100
ttgcgcttca ctttttatca gtgcggtcag aacttcagcc tgagtcaggc catcttcatg    8160
acacatttgc atgagcatgg ccttatactt tggttcaaga aatactttta cttccttgaa    8220
cgaagctctt ttacgggcca ctgataatct ttgtttctct gcatcagaaa gcggattccc    8280
ctttctgtat gctcgttttg cgccagatga ggaagtcact gcattttctg tctgcgacat    8340
ctcgcctcct caatacttaa acagggatcg tttcgcagag gatactacag tttttttgaaa   8400 tcagcgactt gagaattgtg acgaagatcc gggattaccc tgttatccct agagcttggc    8460
gtaatcatgg tcatagctgt ttcctgtgtg aaattgttat ccgctcacaa ttccacacaa    8520
catacgagcc ggaagcataa agtgtaaagc ctggggtgcc taatgagtga gctaactcac    8580
attaattgcg ttgcgctcac tgcccgcttt ccagtcggga aacctgtcgt gccagctgca    8640
ttaatgaatc ggccaacgcg cggggagagg cggtttgcgt attgggcgct cttccgcttc    8700
ctcgctcact gactcgctgc gctcggtcgt tcggctgcgg cgagcggtat cagctcactc    8760
aaaggcggta atacggttat ccacagaatc agggggataac gcaggaaaga acatgtgagc    8820
aaaaggccag caaaaggcca ggaaccgtaa aaaggccgcg ttgctggcgt ttttccatag    8880
gctccgcccc cctgacgagc atcacaaaaa tcgacgctca agtcagaggt ggcgaaaccc    8940
gacaggacta taaagatacc aggcgtttcc ccctggaagc tccctcgtgc gctctcctgt    9000
tccgaccctg ccgcttaccg gatacctgtc cgcctttctc ccttcgggaa gcgtggcgct    9060
ttctcatagc tcacgctgta ggtatctcag ttcggtgtag gtcgttcgct ccaagctggg    9120
ctgtgtgcac gaaccccccg ttcagcccga ccgctgcgcc ttatccggta actatcgtct    9180
tgagtccaac ccggtaagac acgacttatc gccactggca gcagccactg gtaacaggat    9240
tagcagagcg aggtatgtag gcggtgctac agagttcttg aagtggtggc ctaactacgg    9300
ctacactaga aggacagtat ttggtatctg cgctctgctg aagccagtta ccttcggaaa    9360
aagagttggt agctcttgat ccggcaaaca aaccaccgct ggtagcggtg gtttttttgt    9420
```

```
ttgcaagcag cagattacgc gcagaaaaaa aggatctcaa gaagatcctt tgatcttttc   9480
tacggggtct gacgctcagt ggaacgaaaa ctcacgttaa gggattttgg tcatgagatt   9540
atcaaaaagg atcttcacct agatccttttt aaattaaaaa tgaagtttta aatcaatcta   9600
aagtatatat gagtaaactt ggtctgacag ttaccaatgc ttaatcagtg aggcacctat   9660
ctcagcgatc tgtctatttc gttcatccat agttgcctga ctccccgtcg tgtagataac   9720
tacgatacgg gagggcttac catctggccc cagtgctgca atgataccgc gagacccacg   9780
ctcaccggct ccagatttat cagcaataaa ccagccagcc ggaagggccg agcgcagaag   9840
tggtcctgca actttatccg cctccatcca gtctattaat tgttgccggg aagctagagt   9900
aagtagttcg ccagttaata gtttgcgcaa cgttgttgcc attgctacag gcatcgtggt   9960
gtcacgctcg tcgtttggta tggcttcatt cagctccggt tcccaacgat caaggcgagt  10020
tacatgatcc cccatgttgt gcaaaaaagc ggttagctcc ttcggtcctc cgatcgttgt  10080
cagaagtaag ttggccgcag tgttatcact catggttatg gcagcactgc ataattctct  10140
tactgtcatg ccatccgtaa gatgcttttc tgtgactggt gagtactcaa ccaagtcatt  10200
ctgagaatag tgtatgcggc gaccgagttg ctcttgcccg gcgtcaatac gggataatac  10260
cgcgccacat agcagaactt taaaagtgct catcattgga aaacgttctt cggggcgaaa  10320
actctcaagg atcttaccgc tgttgagatc cagttcgatg taacccactc gtgcacccaa  10380
ctgatcttca gcatctttta ctttcaccag cgtttctggg tgagcaaaaa caggaaggca  10440
aaatgccgca aaaaagggaa taagggcgac acggaaatgt tgaatactca tactcttcct  10500
ttttcaatgg ggtgggcgaa gaactccagc atgagatccc cgcgctggag gatcatccag  10560
ccggcgtccc ggaaaacgat tccgaagccc aacctttcat agaaggcggc ggtggaatcg  10620
aaatctcgtg atggcaggtt gggcgtcgct tggtcggtca tttcgaaccc cagagtcccg  10680
ctcagaagaa ctcgtcaaga aggcgataga aggcgatgcg ctgcgaatcg ggagcggcga  10740
taccgtaaag cacgaggaag cggtcagccc attcgccgcc aagctcttca gcaatatcac  10800
gggtagccaa cgctatgtcc tgatagcggt ccgccacacc cagccggcca cagtcgatga  10860
atccagaaaa gcggccattt tccaccatga tattcggcaa gcaggcatcg ccatgggtca  10920
cgacgagatc ctcgccgtcg gcatgcgcg ccttgagcct ggcgaacagt tcggctggcg  10980
cgagcccctg atgctcttcg tccagatcat cctgatcgac aagaccggct tccatccgag  11040
tacgtgctcg ctcgatgcga tgtttcgctt ggtggtcgaa tgggcaggta gccggatcaa  11100
gcgtatgcag ccgccgcatt gcatcagcca tgatggatac tttctcggca ggagcaaggt  11160
gagatgacag gagatcctgc cccggcactt cgcccaatag cagccagtcc cttcccgctt  11220
cagtgacaac gtcgagcaca gctgcgcaag gaacgcccgt cgtggccagc cacgatagcc  11280
gcgctgcctc gtcctgcagt tcattcaggg caccggacag gtcggtcttg acaaaaagaa  11340
ccgggcgccc ctgcgctgac agccggaaca cggcggcatc agagcagccg attgtctgtt  11400
gtgcccagtc atagccgaat agcctctcca cccaagcggc cggagaacct gcgtgcaatc  11460
catcttgttc aatcatgcga aacgatcctc atcctgtctc ttgatcagat cttgatcccc  11520
tgcgccatca gatccttggc ggcaagaaag ccatccagtt tactttgcag gcttcccaa  11580 ccttaccaga gggcgcccca gctggcaatt ccggttcgct tgctgtccat aaaaccgccc  11640
agtctagcta tcgccatgta agcccactgc aagctacctg ctttctcttt gcgcttgcgt  11700
tttcccttgt ccagatagcc cagtagctga cattcatccg gggtcagcac cgtttctgcg  11760
gactggcttt ctacgtgttc cgcttccttt agcagccctt gcgccctgag tgcttgcggc  11820
```

-continued

```
agcgtgaagc tattattgaa gcatttatca gggttattgt ctcatgagcg gatacatatt    11880
tgaatgtatt tagaaaaata aacaaatagg ggttccgcgc acatttcccc gaaaagtgcc    11940
acctgacgtc taagaaacca ttattatcat gacattaacc tataaaaata ggcgtatcac    12000
gaggcgccct ttcgtc                                                   12016
```

```
<210> SEQ ID NO 30
<211> LENGTH: 25
<212> TYPE: DNA
<213> ORGANISM: Artificial
<220> FEATURE:
<223> OTHER INFORMATION: PpiI restriction endonuclease recognition
      sequence
<220> FEATURE:
<221> NAME/KEY: misc_feature
<222> LOCATION: (5)..(9)
<223> OTHER INFORMATION: n is a, c, g, or t
<220> FEATURE:
<221> NAME/KEY: misc_feature
<222> LOCATION: (13)..(25)
<223> OTHER INFORMATION: n is a, c, g, or t

<400> SEQUENCE: 30
gaacnnnnnc tcnnnnnnnn nnnnn                                           25
```

```
<210> SEQ ID NO 31
<211> LENGTH: 24
<212> TYPE: DNA
<213> ORGANISM: Artificial
<220> FEATURE:
<223> OTHER INFORMATION: PpiI restriction endonuclease complementary
      recognition sequence
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (13)..(24)
<223> OTHER INFORMATION: n is a, c, g, or t

<400> SEQUENCE: 31
gagnnnnngt tcnnnnnnnn nnnn                                            24
```

```
<210> SEQ ID NO 32
<211> LENGTH: 25
<212> TYPE: DNA
<213> ORGANISM: Artificial
<220> FEATURE:
<223> OTHER INFORMATION: PpiI restriction endonuclease complementary
      recognition sequence
<220> FEATURE:
<221> NAME/KEY: misc_feature
<222> LOCATION: (5)..(9)
<223> OTHER INFORMATION: n is a, c, g, or t
<220> FEATURE:
<221> NAME/KEY: misc_feature
<222> LOCATION: (13)..(25)
<223> OTHER INFORMATION: n is a, c, g, or t

<400> SEQUENCE: 32
gaacnnnnnc tcnnnnnnnn nnnnn                                           25
```

```
<210> SEQ ID NO 33
<211> LENGTH: 24
<212> TYPE: DNA
<213> ORGANISM: Artificial
<220> FEATURE:
<223> OTHER INFORMATION: PpiI restriction endonuclease complementary
      recognition sequence
```

```
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (13)..(24)
<223> OTHER INFORMATION: n is a, c, g, or t

<400> SEQUENCE: 33
gagnnnnngt tcnnnnnnnn nnnn                                              24
```

PLASMID CURING

REFERENCE TO SEQUENCE LISTING

A Sequence Listing is submitted herewith through EFS-Web as an ASCII compliant text file. The text file is named "7492107AST25.txt", was created on Feb. 3, 2014, and is 98 kilobytes in size. The Sequence Listing is incorporated by reference herein.

The present invention relates to plasmid curing, and particularly to efficient and stress-free methods for displacing resident or endogenous plasmids from a host cell, such as a bacterium. The invention extends to recombinant plasmids used in said methods, cells containing such plasmids, and also to kits for carrying out the methods.

Bacteria are a large group of single-celled micro-organisms, many of which cause infections and disease in animals and humans. For example, the Enterobacteriaceae are a large family of bacteria, which occur both commensally and pathogenically in the intestines, causing wide-spread disease. Most of the essential genes in a bacterium that are required for survival under normal or optimum conditions are contained in the chromosome. However, many bacteria also carry a variety of Mobile Genetic Elements (MGE) that can contribute significantly to their diversity and adaptability. These MGEs do not carry anything essential for survival under non-stressful circumstances, but may be important for specialised functions, such as the ability of the bacterium to form biofilms or to be resistant to antibiotics.

Plasmids are the most easily identified MGE, because they are physically separate from the chromosome and can be visualised by lysis and electrophoretic separation of the released DNA molecules. Plasmids are genetic elements that exist in bacteria and behave rather like mini-chromosomes. Although mounting DNA sequence information for the complete genomes of many bacterial species allows functional predictions using bioinformatics, it is still important and preferred to experimentally test the contribution of plasmids to their host's phenotype.

Classically to determine the phenotype(s) conferred by a plasmid, one needs to obtain both a plasmid-free segregant that has lost the plasmid and determine what properties, if any, have been lost, and also transfer the plasmid to a new strain and determine what new phenotype(s) is acquired along with the plasmid. A key part of this empirical work is displacement of the endogenous or resident plasmid from its natural host, which is a process called curing. While some plasmids seem to be naturally unstable and may be easily lost from the host, many are very persistent and active strategies are needed to obtain a plasmid-free bacterium.

By definition, plasmids are non-essential, except under certain conditions, such as when an antibiotic or an unusual nutrient is present. Thus, in rich growth conditions, it should be possible to displace the plasmid. However, because naturally occurring plasmids are the ones that have survived selective pressure over millions of years, they tend to be very stable. Hence, to find out what property they confer on the bacterium that carries them, it is essential to displace them to produce bacteria that lack the plasmid so that bacteria with and without the plasmid can be compared.

The classic strategy to cure a strain of its resident plasmid is to stress the bacteria in some way, for example by growth at high temperature, or in the presence of a detergent, mutagens or some other DNA modulating agents, such as intercalating agents. Unfortunately, these procedures are stressful to the host, and most suffer the problem that part of the bacterial stress response is to increase the mutation rate. This can result in alteration of the host's phenotype irrespective of whether the plasmid has being displaced or not, thereby seriously undermining the conclusions that can be drawn.

An alternative approach for curing a host cell of its endogenous plasmid is to use the property of "plasmid incompatibility" to displace the resident plasmid. Plasmid incompatibility is the inability of plasmids to co-exist, stably, within the same cell when they have similar or identical systems for plasmid replication and/or plasmid partition, i.e. the segregation of each plasmid into daughter cells during cell division. Two incompatible plasmids, which occupy the same cell will, in the absence of a selective pressure for both plasmids, tend to segregate or partition to different cells during cell division. The stable intracellular co-existence of one plasmid with another requires that each plasmid is able to control, independently of the other, its own replication/partition such that it can establish and maintain a stable copy number. However, the inability of a given plasmid to maintain a stable copy number in the presence of another plasmid is the characteristic feature of incompatibility.

Hence, if the two plasmids go through the same critical step, for example, is placed under selective pressure, then random selection will cause one or other plasmid to dominate, and eventually the other will be lost. This displacement of one plasmid by the other can become effectively unidirectional if one of the two plasmids contains a second replication system that is not affected by the other plasmid, especially if the second replication system has a naturally higher copy number. Under these circumstances, the normally lower copy number plasmid will react as if it has over-replicated and further replication of that plasmid type in the cell will be switched off, resulting in its displacement.

Tatsuno et al. (Infection and Immunity, 69, 6660-6669) attempted to cure the endogenous plasmid, pO157, from its *E. coli* host, by using the incompatibility of a mini-replicon derived from part of the pO157 genome. However, they observed inefficient curing, in which only 7 out of a total of 41 transformants screened had lost the plasmid. Hence, the method disclosed by this group was ineffective.

Independently of the processes that increase the probability of receiving a plasmid from a parent cell at division, there are very special strategies adopted by many plasmids that prevent plasmid-free segregants from surviving. Terms such as killer system, killing-anti-killing, post-segregational killing, toxin-antitoxin, poison-antidote, plasmid addiction system or programmed cell death are all used to describe the situation when the host cell is selectively killed if it has not received any copy of the plasmid. The molecular basis of this killing requires the existence of at least two plasmid genes: one specifying a stable toxic agent, and another coding for an unstable factor, which prevents lethal action of the gene encoding the toxic agent. While the toxins identified so far are always proteins, the antidote may be either antisense RNA (which inhibits translation of toxin mRNA) or a protein (that prevents the effect of the toxin in one way or another).

Hence, a significant problem encountered by researchers when attempting to cure a bacterium of its endogenous plasmids, is that unfortunately many plasmids encode a so-called Post-Segregational Killing System (PSK), which causes loss of viability of the bacterial cells that have lost their endogenous plasmid. This happens because the endogenous plasmid leaves behind either (i) protein, which becomes toxically active after loss of the plasmid; or (ii) mRNA, which is translated to produce a toxin. Action of the toxin, which is lethal to the host, is normally kept in check either:—(i) by regulators, which control expression of the mRNA that is left behind; by (ii) antidote proteins, which counteract the toxic effects of the toxin; or by (iii) antisense RNA, which binds to and neutralises the effects of the toxic mRNA. The regulators, the antidote proteins, and the antisense RNA are all encoded by the endogenous plasmid, and are unstable, and therefore decay once the endogenous plasmid that encodes them is no longer present in the host. Therefore, the result is death of the bacteria, from which the endogenous plasmid has been displaced.

Therefore, it will be appreciated that there are a number of factors involved with the displacement of an endogenous plasmid from a host bacterium, which need to be considered if efficient plasmid displacement is to be achieved in practise, such that the host cell remains viable. It is therefore an aim of the present invention to obviate or mitigate one or more of the problems of the prior art, whether identified herein or elsewhere, and to provide an improved method of curing endogenous plasmids from a host cell.

The inventors of the present invention appreciated that the significant problem involved with curing or displacing endogenous plasmids from a host cell is cell death, and that this is occurs when the endogenous plasmid encoded a Post-Segregational Killing system (PSK). Hence, in order to overcome the objective technical problem of cell death or lack of cell viability caused by plasmid displacement, the inventors set out to develop an improved method for displacing the endogenous plasmid from a host cell. In order to do this, the inventors designed a so-called recombinant displacement plasmid, which incorporated part of the PSK system encoded by the endogenous plasmid. To their surprise, the inventors found that use of such a recombinant displacement plasmid was very efficient at curing endogenous plasmids encoding a PSK system from the host cell.

Hence, according to a first aspect of the present invention, there is provided a method of displacing a plasmid comprising a post-segregational killing system from a host cell, the method comprising introducing a recombinant nucleic acid molecule into a host cell harbouring a plasmid comprising a post-segregational killing system, characterised in that the recombinant nucleic acid molecule is adapted to neutralise the toxic effects of the plasmid's post-segregational killing system, and wherein the nucleic acid molecule is also adapted to outcompete or inhibit replication of the plasmid.

The inventors have demonstrated that the method according to the first aspect has significant advantages over existing methods used for curing plasmids comprising a post-segregational killing system from host cells, which use only incompatibility determinants for the replication system of the plasmid. The method according to the invention does not involve having to stress the host cell in any way, for example by growth at high temperatures, or in the presence of a detergent, mutagen or some other DNA modulating agents, such as an intercalating agent. In addition, the method according to the invention avoids the stress of inducing and surviving the effects of post-segregational killing systems, or of other lethal gene products produced by the plasmid.

The above advantages of the method according to the invention are made possible by introducing into the host cell the recombinant nucleic acid molecule, which has two key features, namely that it is adapted to (i) outcompete or inhibit replication of the plasmid, and also (ii) neutralise the toxic effects of the plasmid's post-segregational killing system. This latter feature of the method of the invention (i.e. neutralisation of the plasmid's PSK system) has, to date, not been recognised in the design of existing plasmid displacement strategies. Furthermore, surprisingly, the inventors believe that the method according to the invention is applicable for curing any plasmid, which has a post-segregational killing system from any host cell where it is possible to predict the replication and stable inheritance regions of the resident plasmid, and also the sequence of the PSK system. By the term "displacing the plasmid from the host cell", we mean to remove or cure the plasmid from the host cell.

The plasmid being displaced (or cured) from the host cell may be any plasmid present in the host cell, having a PSK system. For example, the plasmid may be an exogenous plasmid, which has been introduced into the host cell, for example, by transformation, and which then subsequently needs to be displaced therefrom. By the term "exogenous plasmid", we mean a plasmid, which originates from, or is developed or produced by, a cell other than the host cell, but which is then introduced into the host cell by some means.

However, it is preferred that the method according to the invention is used to displace a plasmid that is an endogenous plasmid to the host cell, which needs to be displaced or cured therefrom. By the term "endogenous plasmid", we mean a plasmid, which originates from, or is developed or produced by, the host cell. The plasmid being displaced from the host cell may be either autonomously replicating in the host cell, or may be integrated in the host cell's genome.

It will be appreciated that the plasmid to be displaced from the host cell comprises a post-segregational killing system (PSK). By the term "post-segregational killing system" or "PSK" (which are used interchangeably herein), we mean any of the known mechanisms adopted by plasmids that prevent plasmid-free segregants from surviving. For example, any of the terms known in the art such as:—killer system; killing-anti-killing; post-segregational killing; toxin-antitoxin; poison-antidote; plasmid addiction system; or programmed cell death, are all terms that are used by the skilled technician to describe a suitable mechanism used to selectively kill a host cell if it does not contain a copy of the plasmid, and are therefore analogous to the term PSK system. The term PSK also encompasses other systems that have effectively the same properties, namely restriction modification systems and bacteriocin production/immunity systems. It will be appreciated that the PSK system usually comes into play after cell division.

It will be appreciated that the Post-Segregational Killing (PSK) system generally comprises two components, (i) a toxin and (ii) an antidote, both of which are preferably genetically encoded by the plasmid to be displaced from the host cell. The toxin gene may comprise a nucleic acid sequence, which is transcribed into mRNA, which mRNA may itself be toxic to the host cell, or which may be subsequently translated into a protein, which protein is toxic to the host cell and possibly to similar neighboring cells (as in the case of bacteriocins). The antidote gene preferably comprises a nucleic acid sequence, which encodes either:—(i) a regulator protein adapted to modulate (e.g. minimise or substantially prevent) expression of the toxin gene into mRNA; (ii) an antisense RNA, which is adapted to bind to and prevent the toxic action of the toxic mRNA; or (iii) an antidote protein, which is adapted to neutralise the toxic effects of the protein either by binding to it or by protecting the cell from its effects as in the case of DNA modification enzymes that protect against the effect of restriction enzymes.

It will be appreciated that expression of the toxin gene in the host cell, whether it encodes a toxic mRNA and/or a toxic protein, causes the problem that the host cell would otherwise die in the absence of the antidote, whether it comprises a regulator, antisense RNA and/or antidote protein. Hence, the nucleic acid molecule being introduced into the host cell is adapted to neutralise the toxic effects of the plasmid's PSK system to avoid host cell death, and this may be achieved in several ways. Preferably, the nucleic acid molecule introduced into the host cell in the method according to the invention is capable of genetically complementing the antidote part of the PSK system on the plasmid being displaced from the host cell. By the term "genetically complement", we mean that the nucleic acid molecule encodes at least a region of the same PSK system as on the plasmid being displaced so that once the plasmid has been displaced from the cell, the genes "lost" are compensated for or retained in the cell due to being encoded on the nucleic acid molecule.

It is most preferred that the nucleic acid molecule is capable of genetically complementing the antidote-encoding genes of the PSK system on the plasmid being displaced from the host cell. Some PSK systems may comprise more than one antidote-encoding gene, and in such cases, it is envisaged that the nucleic acid molecule is capable of genetically complementing at least one, and preferably each, antidote-encoding gene of the PSK system on the plasmid. Advantageously, the nucleic acid molecule genetically complements the antidote-encoding gene, which is subsequently lost upon displacement of the plasmid from the host, thereby ensuring that any toxins produced by the PSK system on the plasmid are neutralised, hence, maintaining cell viability.

Preferably, the nucleic acid molecule comprises at least a region of an antidote-encoding gene or a functional variant thereof of the PSK system encoded by the plasmid being displaced. It is preferred that the nucleic acid molecule comprises substantially the same sequence as that of the antidote-encoding gene of the PSK system in the plasmid being displaced. Hence, ideally, it is preferred that the sequence of the PSK system or at least the sequence of the antidote-encoding gene or genes on the plasmid is known so that this sequence may be used in the nucleic acid molecule so that genetic complementation may take place. It will be appreciated that although similar in function, the sequence of the genes making up various PSK systems will vary between organisms, and some examples are provided herein. Nevertheless, the skilled technician should know how to determine or at least predict the sequence of the antidote-encoding gene or genes of the PSK system encoded by the plasmid being displaced. However, it is also envisaged that the nucleic acid molecule may comprise a functional variant of the antidote-encoding gene of the PSK system of the plasmid being displaced.

By the term "functional variant of the PSK system", or "functional variant of an antidote-encoding gene", we mean that the sequence of the nucleic acid molecule (or the amino acid sequence encoded thereby) has at least 30%, preferably 40%, more preferably 50%, and even more preferably, 60% sequence identity with the amino acid/nucleic acid sequence of the PSK system, or at least the antidote-encoding gene on the plasmid being displaced. Examples of suitable sequences of PSK systems and antidote-encoding genes are provided herein (for the hok/sok system, X05813.1; for the ccd system, X00594.1; for the parD/E system, M61010). An amino acid/nucleic acid sequence with a greater identity than preferably 65%, more preferably 75%, even more preferably 85%, and even more preferably 90% to the sequence of the PSK system of the plasmid being displaced is also envisaged. Preferably, the sequence of the nucleic acid molecule or the amino acid encoded thereby has 92% identity, even more preferably 95% identity, even more preferably 97% identity, even more preferably 98% identity and, most preferably, 99% identity with the sequence of the PSK in use.

The skilled technician will appreciate how to calculate the percentage identity between two amino acid/polynucleotide/polypeptide sequences, for example, as described in http://wikiomics.org/wiki/Percentage_identity. In order to calculate the percentage identity between two amino acid/polynucleotide/polypeptide sequences, an alignment of the two sequences must first be prepared, followed by calculation of the sequence identity value.

The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences is then calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence, which hybridizes to nucleotide sequences referred to herein or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from polypeptide sequences referred to herein.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will known the nucleotide sequences encoding these amino acids.

The nucleic acid molecule may neutralise the toxic effects of the plasmid's PSK system in several ways. For example, the nucleic acid molecule being introduced into the host cell may encode a regulator protein, which is adapted to modulate expression of a toxin gene of the plasmid's PSK system into mRNA. Preferably, the regulator protein is adapted to minimise or substantially prevent expression of the plasmid's toxin gene. Hence, no toxic mRNA is produced by the plasmid being displaced and so the host cell is not killed after displacement of the plasmid.

Alternatively, or additionally, the nucleic acid molecule introduced into the host cell may encode antisense RNA, which is adapted to bind to and prevent the toxic action of any toxic mRNA (generally but not necessarily translation to produce a toxic protein), which may be produced by the plasmid being displaced. Hence, any toxic mRNA, which may be produced by the plasmid being displaced is neutralised, and so the host cell is not killed after displacement of the plasmid.

Alternatively, or additionally, the nucleic acid molecule introduced into the host cell may encode an antidote protein, which is adapted to bind to and prevent the toxic action of any toxic protein, which may be produced by the plasmid being displaced. Hence, any toxic protein, which may be produced by the plasmid being displaced is neutralised, and so the host cell is not killed after displacement of the plasmid.

Alternatively, or additionally, the nucleic acid molecule introduced into the host cell may encode a DNA modification enzyme, which is adapted to prevent the toxic action of any restriction endonuclease, which may be produced by the plasmid being displaced. Hence, any toxic protein, which may be produced by the plasmid being displaced is neutralised, and so the host cell is not killed after displacement of the plasmid.

Alternatively, or additionally, the nucleic acid molecule introduced into the host cell may encode an immunity protein, which protein is adapted to prevent the toxic action of any secreted toxin protein (generically called a bacteriocin), which may be produced by the plasmid being displaced. Hence, any toxic protein, which may be produced by the plasmid being displaced is neutralised, and so the host cell is not killed after displacement of the plasmid.

It will be appreciated that in each of the above cases, the provision of the antidote gene on the nucleic acid molecule being introduced into the host cell, and hence, the provision of the antidote to the host cell, prevents death of the host after the plasmid has been displaced or cured therefrom. Hence, it will be appreciated that an important feature of the method according to the invention is that the nucleic acid molecule, which is introduced into the host cell has the dual effect of both neutralising the toxic effects of the PSK system encoded by the plasmid being displaced, and in addition, out-competing replication of the plasmid. The result is that not only does the nucleic acid molecule cause the plasmid to be displaced from the host cell, but it also is capable of preventing host cell death, or any reduction in host cell viability, which would otherwise be caused by the toxic effects of toxic mRNA or toxic protein produced by the PSK system of the plasmid being displaced.

It will be appreciated that the nucleic acid molecule being introduced into the host cell is adapted to compete with or inhibit replication of the plasmid being displaced, and this may also be achieved in a number of different ways. For example, the nucleic acid molecule may act in a competitive manner, positively out-competing the replication functions of the plasmid being displaced. For example, the nucleic acid may contain all or selected parts of an origin of replication or one or more replicons from the plasmid being displaced from the host cell. The nucleic acid molecule may be adapted to replicate at a higher rate than the plasmid being displaced from the host cell. For example, the nucleic acid molecule may comprise an origin of replication or a replicon, which is capable of replicating the nucleic acid molecule at a higher rate than the replication of the plasmid being displaced.

By the term "replicon", we mean a nucleic acid sequence that comprises an origin of replication (e.g. oriV), and is capable of replicating as an individual unit in a suitable host cell.

As a result of this competition between the plasmid and the nucleic acid molecule and selection for those cells that retain the nucleic acid molecule, cells in which the plasmid is out-competed can be selected and therefore actively displaced from the host cell. The skilled technician will appreciate the different types of replicon that are available, depending on the type of host and the type of plasmid being displaced. An example of a suitable replicon for *E. coli* is oriC which uses the same replicon as the bacterial chromosome and does not appear to encode negative feedback loops, so that displacement of one oriC plasmid by another is primarily through competition.

Alternatively, or additionally, the nucleic acid molecule may be adapted to inhibit replication of the plasmid being displaced. For example, the nucleic acid molecule may encode an inhibitor molecule, which inhibits or prevents replication of the plasmid being displaced. The inhibitor molecule may be either RNA or protein. Hence, advantageously, as the inhibitor inhibits replication of the plasmid, the plasmid is thereby displaced from the host cell. An example of a suitable inhibitor for *E. coli* is the antisense RNA CopA of the IncFII replicon.

Alternatively, the inhibitory effect may be due to binding sites for a replication protein that plays both a negative and a positive role, and which allows 'handcuffing' and therefore blocking of the replication origin or other essential parts of the replicon.

It is preferred that the two features of the recombinant nucleic acid molecule (i.e. the antidote-encoding gene, and the replicon or inhibitor-encoding gene) are operatively linker together such that they are expressed in the host cell.

It will be appreciated that the nature of the nucleic acid molecule will be determined by the nature of the plasmid being displaced from the host, and also the host itself. Hence, the nucleic acid molecule may comprise RNA, but preferably comprises DNA. It is preferred that the nucleic acid molecule is derived from the same organism as the host cell in which it is being introduced, as this is thought to improve the likelihood of successful expression of the nucleic acid molecule and genes thereof, in the host cell.

The nucleic acid molecule may be introduced into the host cell by any suitable means as a "naked" or linear nucleic acid molecule. For example, linear nucleic acid molecules may be introduced into the cell by transformation or electroporation. The skilled technician will appreciate that appropriate linear DNA molecules comprising a suitable replicon can replicate and function efficiently in a host cell to thereby displace the plasmid. Alternatively, the nucleic acid molecule may be incorporated within a liposome, or a virus particle, which may then be subsequently introduced into the host cell. Alternatively, the nucleic acid molecule may be introduced into the host cell by conjugative transfer from a donor bacterium so long as the nucleic acid contains an appropriate transfer origin.

However, it is preferred that the nucleic acid molecule is circular. For example, the nucleic acid molecule may be contained within a suitable vector to form a recombinant vector. For example, the vector may comprise or be derived from a plasmid, cosmid, phage, or virus, or the like, which will be known to the skilled technician. Examples of a suitable virus (bacteriophages) for bacteria include lambda, P1 or M13. Examples of a suitable virus include a retrovirus, herpes virus, pox virus, vaccina virus, adenovirus, or lentovirus.

In embodiments where the nucleic acid molecule is in the form of a circular piece of DNA, it may be referred to as a "displacement plasmid" or "displacement vector". Such recombinant plasmids or vectors are highly useful for transforming the host cell with the nucleic acid molecule. In addition to the nucleic acid molecule encoding the antidote gene, the molecule also comprises functional genetic elements required for replication of the nucleic acid molecule in the host cell, and this allows the molecule to out-compete the replication of the plasmid being displaced. For example, the molecule may be designed such that it is capable of autonomously replicating in the host cell. In this case, the nucleic acid molecule preferably comprises elements that induce expression of the genes it encodes and preferably, replication of the nucleic acid molecule. Such elements may comprise a promoter and regulatory units associated with gene expression and replication.

Alternatively, the recombinant nucleic acid molecule may be designed such that it is capable of integrating into the genome of the host cell. In such embodiments, the nucleic acid molecule preferably comprises nucleic acid sequences, which favour targeted integration into the host's genome, for example, by homologous recombination. The host cell may be transformed with the nucleic acid molecule either as linear or circular DNA, resulting in the production of daughter cells, in which case regulation of expression of the molecule in the host cell may be required, for example with specific transcription factors or gene activators or repressors, and so on. Alternatively, the nucleic acid molecule may be designed to favour unstable or transient transformation of the host cell, in which case regulation of expression may be less important.

The method according to the invention comprises introducing the nucleic acid molecule into the host cell by any suitable means, which will be determined by the host cell itself. For example, the nucleic acid molecule may be introduced into the host by transfection, transformation, infection, microinjection, electroporation, cell fusion, protoplast fusion, conjugative transfer, or ballistic bombardment. For example, transfer may be by ballistic transfection with coated gold particles, or by liposomes containing the nucleic acid sequence, or by a viral vector (e.g. a lambda vector), or by means of providing direct nucleic acid uptake (e.g. divalent cation mediated transformation), or by application of the nucleic acid molecule directly into the host cell.

The nucleic acid molecule preferably comprises a gene encoding a selectable marker, which facilitates the cloning process, and which may be used to isolate host cells, which have been successfully transformed with the nucleic acid molecule. The choice of a suitable selectable marker will depend on the nature of the host cell, and will be known to the skilled technician. For example, in *E. coli* preferred markers may include the Kanamycin resistance gene, which will be known to the skilled technician.

Preferably, once the nucleic acid molecule has been introduced into the host cell, the method comprises a step of subjecting the host cell to conditions such that the endogenous plasmid is displaced therefrom. This step may comprise selection on suitable media, which may select for host cells in which the nucleic acid is established and by inference the plasmid would be absent. Hence, the nucleic acid molecule causes the plasmid to be displaced from the host cell, and also prevents cell death by virtue of its capability to neutralise the toxic effects of the plasmid's PSK system.

Once the plasmid has been displaced from the host cell, it may then be required to subsequently displace the nucleic acid molecule from the host cell to thereby provide a host lacking the plasmid and the nucleic acid molecule. Hence, preferably, the method according to the invention comprises a further step of subjecting the host cell to conditions such that the nucleic acid molecule is subsequently displaced therefrom, after the plasmid has been successfully displaced. This step may be achieved by a number of different ways, but preferably comprises subjecting the host cell to selective pressure, whereby the nucleic acid molecule is removed from the host cell, and then selecting for cells, which lack the nucleic acid molecule. Accordingly, it is preferred that the nucleic acid molecule comprises a suitable selectable marker. A preferred marker may include the sacB gene for use in *E. coli*, in which the presence of the sacB gene makes the host sensitive to sucrose. Hence, adding sucrose to media will prevent growth of a host carrying the sacB gene.

As described in the Examples, the inventors focussed their research on the F family of plasmids of *Escherichia coli*, and the broad-host-range IncP-1 family, which can be maintained in all Gram-negative bacterial species. Therefore, the inventors envisage that the method according to the invention may be readily applied to a much wider range of species and organisms. Hence, in one embodiment, the host cell from which the plasmid may be displaced may be a eukaryotic cell. It is known that many eukaryotic organisms harbour plasmids, which may need to be displaced, some of which may comprise a PSK system, and which therefore suffer the technical problem of host cell death upon displacement of that plasmid. For example, the host cell may be a yeast cell. For example, plasmids in a variety of yeast encode killer factors as well as the immunity to these factors. A specific example is the plasmid pGKL1 of *Kluyveromyces lactis* (Stark et al., Nucleic Acids Research 12, 6011-6030).

However, it is preferred that the host cell is a prokaryotic cell. It will be appreciated that suitable prokaryotes for use in the method of the invention include mycoplasma, blue-green alga, or bacteria (e.g. eubacteria or archaebacteria), and any of these organisms may have their endogenous plasmids displaced. Preferably, the host cell is a bacterial host cell, which may be gram positive or gram negative.

Suitable Gram-positive bacteria, which may be cured of their plasmids using the method of the invention, include the phylum Firmicutes, which includes *Bacillus* spp, *Lactobacil-* lus spp., *Lactococcus* spp., *Staphylococcus* spp, *Streptococcus* spp, *Listeria* spp, *Enterococcus* spp, and *Clostridium* spp.

Examples of plasmids harboured by *Bacillus* spp, and which may be cured using the method according to the invention include pPOD2000/pTAO1050 (Meijer et al., FEMS Microbiology Reviews 21, 1998, 337-368). Examples of plasmids harboured by *Staphylococcus* spp, and which may be cured using the method according to the invention include pI-1 (Aso, Y. J., Koga, H., Sashihara, T., Nagao, J. I., Kanemasa, Y., Nakayama, J. and Sonomoto, K., 2005. Plasmid 53, 164-178). Examples of plasmids harboured by *Streptococcus* spp, and which may be cured using the method according to the invention include pSM19035 (Zielenkiewicz, U. and Ceglowski, P., 2005. J. Bacteriol. 187, 6094-6105). Examples of plasmids harboured by *Listeria* spp, and which may be cured using the method according to the invention include an unnamed megaplasmid from strain C20 (Halami, P. M., Ramesh, A. and Chandrashekar, A., 2000. Food Microbiology 17, 475-483). Examples of plasmids harboured by *Enterococcus* spp, and which may be cured using the method according to the invention include pAD1 (Greenfield, T. J., Ehli, E., Kirshenmann, T., Franch, T., Gerdes, K. and Weaver, K. E., 2000. Mol. Microbiol. 37, 652-660). Examples of plasmids harboured by *Lactocobacillus* spp, and which may be cured using the method according to the invention include pLME300 (Gfeller, K. Y., Roth, M., Melle, L. and Teuber, M., 2003. Plasmid 50, 190-201).

Suitable Gram negative bacteria, which may be cured of their plasmids using the method of the invention include Proteobacteria. For example, Gram-negative bacteria may include Enterobacteriaceae spp, *Pseudomonas* spp, *Moraxella* spp, *Helicobacter* spp, *Stenotrophomonas* spp, *Bdellovibrio* spp, and *Legionella* spp.

A preferred host cell used in accordance with the method of the invention comprises *Enterobacter* spp, which is a genus of common Gram-negative facultatively-anaerobic bacteria of the family Enterobacteriaceae. On Gram staining, these cells are rod-shaped. Several of these bacteria are pathogenic and cause opportunistic infections in compromised (usually hospitalised) hosts. The urinary and respiratory tract are the most common sites of infection. Two clinically-important species from this genus are *Enterobacter aerogenes* and *Enterobacter cloacae*.

The Example provides specific details of the method according to the invention, and it will be seen that the inventors focussed their research on the F family of plasmids of *Escherichia coli*, and the broad-host-range IncP-1 family originally identified in *Pseudomonas aeruginosa* and *Enterobacter aerogenes* but in fact belonging generally to gram negative bacteria. Even though the inventors envisage that the method of the invention may be readily applied to a much wider range of species and organisms, a preferred host cell used in the method of the invention comprises *E. coli*. Another preferred host cell used in the method of the invention comprises *Pseudomonas* spp, and most preferably, *P. putida*.

Hence, an example of a preferred plasmid, which may be displaced from the host cell using the method according to the invention includes an F-family plasmid (for example from *E. coli*). The F-family plasmid (or F-like plasmid) will be known to the skilled technician and may also be referred to as: F agent, F factor, F genote, F-genote, fertility agent, and fertility factor plasmid (Firth, N., K. Ippen-Ihler, and R. Skurray, 1996. by F. C. Neidhart (ed), ASM, Washington 2377-2401).

Another example of a preferred plasmid, which may be displaced from the host cell using the method according to the invention includes a broad-host-range plasmid belonging to the *E. coli* Incompatibility (Inc) group P (IncP-1 in *Pseudomonas* species). Incompatibility groups (Inc groups) exist, e.g. for plasmids which occur in enterobacteria, and separate Inc groups exist for plasmids which occur in other bacteria. Some so-called 'promiscuous' plasmids can occur e.g. in both enterobacteria and *Pseudomonas* spp, and some of the plasmids have been allocated to an Inc group in both the enterobacterial and pseudomonad plasmid grouping schemes.

Hence, the plasmid may comprise an Enterobacterial Inc group plasmid. Enterobacterial Inc groups are designated by the prefix 'Inc' followed by a letter and sometimes a Roman numeral or a Greek letter. Some examples of suitable enterobacterial Inc group plasmids, which may be displaced using the method according to the invention may be independently selected from a group consisting of: IncFI (such as F plasmid, the Colicin plasmid, ColV-K94, and the R plasmid, R386); IncFII (such as the R1 plasmid, R6 and R100); Incα (sometimes written Incl1 or $IncI_1$), such as ColIb-P9, the delta plasmid and R64; Incγ (such as R621a); IncN (such as N3, R46, and R269N-1); and IncX (such as the R6K plasmid).

The plasmid may comprise a *Pseudomonas* Inc group plasmid. The skilled technician will appreciate that *Pseudomonas* Inc groups are designated IncP-1 to IncP-13, the numbers referring to each of 13 different types of replication system. Hence, the plasmid being displaced may be any one of the IncP-1 to IncP-13 plasmids. Some examples of suitable *Pseudomonas* Inc group plasmids, which may be displaced using the method according to the invention may be independently selected from a group consisting of: IncP-2 (such as the Cam plasmid, the Oct plasmid, and the R plasmid, pMG1); IncP-6 (such as the R plasmid, Rms149); IncP-7 (such as Rms148); IncP-8 (such as FP2); IncP-9 (such as R2, the Sal plasmid, and the Tol plasmid); IncP-10 (such as R91); Inc-11 (such as RP8 and R151); IncP-12 (such as R716); and IncP-13 (such as pMG25).

Examples of shared enterobacterial and pseudomonad Inc group plasmids which may be displaced using the method according to the invention may be independently selected from a group consisting of: IncC (i.e. IncP-3), such as R55; and IncQ (i.e. IncP-4), such as RSF1010.

However, preferred shared enterobacterial and pseudomonad Inc group plasmids, which may be displaced using the method of the invention includes IncP (i.e. IncP-1), such as IncP-1 alpha plasmids RP1, RP4, RK2, R68, and such as IncP-1 beta plasmids R751, R906, pADP1, pOU1, pJP4, pB3, pB4, pB8, pB10, and such as IncP-1 gamma plasmid pQKH54 and such as IncP-1 delta plasmid pEST4011 and The inventors realised that the *E. coli* plasmid, pO157 (as shown in FIG. 1; Burland, V., Shao, Y., Perna, N. T., Plunkett, G., Sofia, H. J. and Blattner, F. R., 1998. The complete DNA sequence and analysis of the large virulence plasmid of *Escherichia coli* O157: H7. Nucleic Acids Res. 26, 4196-4204; Makino, K., Ishii, K., Yasunaga, T., Hattori, M., Yokoyama, K., Yutsudo, C. H., Kubota, T., Yamaichi, Y., Iida, T., Yamamoto, K., Honda, T., Han, C. G., Ohtsubo, E., Kasamatsu, M., Hayashi, T., Kuhara, S, and Shinagawa, H., 1998. Complete nucleotide sequences of 93-kb and 3.3-kb plasmids of an enterohemorrhagic *Escherichia coli* O157:H7 derived from Sakai Outbreak. DNA Res. 5, 1-9.) is typical of many of the general F-like plasmids, possessing multiple replicons, stable inheritance functions, and PSK systems representative of other F incompatibility group plasmids. Therefore, the inventors devised a sophisticated approach for displacing any F-like plasmids by generating a recombinant displacement plasmid (referred to as pCURE1), which includes various segments from the genome of the plasmid, pO157. The displacement plasmid was then introduced into an *E. coli* host cell, and cultured appropriately. Using the recombinant plasmid and inventive endeavour involving detailed consideration of plasmid replication and stable inheritance systems, the inventors achieved a 100% efficient displacement of the resident endogenous plasmid (pO157) from *E. coli*.

Hence, in one preferred embodiment of the invention, the method preferably comprises displacing an F-like plasmid (for example, pO157) from a host cell (for example, *E. coli*). Preferably, the nucleic acid molecule that is introduced into the host cell comprises a vector, which preferably comprises a functional control region of at least one replicon from pO157, that represses replication and partitioning (i.e. copy number control regions) of pO157. Examples of suitable replicons that the recombinant nucleic acid molecule may comprise include repFIIA and repFIB, the sequences of which are shown in AB011548; coordinates 72000-73400 and 26000-28000. Preferably, the nucleic acid molecule comprises repFIIA and/or repFIB, but preferably comprises both replicons operatively linked together.

Preferably, the nucleic acid molecule introduced into the host cell comprises suitable control and antidote regions from identified PSK systems from pO157 that would normally decrease the survival of plasmid-free segregants. Examples of suitable PSK systems from pO157 include the flmA/C (hok/sok) system and the letA/letB (ccdA/ccdB) system, the sequences of which are shown in AB01158 coordinate 73000-75000 and 28000-29500 respectively. Hence, the nucleic acid molecule may comprise the sok gene of the hok/sok system and/or the letA gene from the letAB system. Preferably, the molecule comprises both the sok gene and the letA gene operatively linker together.

It is most preferred that the nucleic acid molecule comprises repFIIA, repFIB, sok, and letA operatively linked together such that each gene is expressed in the host cell. The inventors used PCR to amplify each of these regions of the post-segregational killing system loci (sok, and letA), and the replicons (repFIIA, repFIB). PCR will be known to the skilled technician, and details of suitable primers and PCR reaction conditions used to amplify suitable amounts of these features of the nucleic acid molecule are provided in the Examples. These PCR products were then introduced into a small unstable cloning vector, pAKE604 (El-Sayed, A. K., Hothersall, J. and Thomas, C. M., 2001. Microbiology-SGM 147, 2127-2139), as shown in FIG. 2.

The nucleotide sequence of pAKE604 (7219 bp) is identified as SEQ ID No. 1.

```
[SEQ ID No. 1]
TCGCGCGTTTCGGTGATGACGGTGAAAACCTCTGACACATGCAGCTCCCG
GAGACGGTCACAGCTTGTCTGTAAGCGGATGCCGGCAGCAGACAAGCCCG
TCAGGCCGCGTCAGCGGGTGTTGGCGGGTGTCGGGGCTGGCTTAACTATC
CGGCATCAGAGCAGATTGTACTGAGAGTGCACCATAATCGGCATTTTCTT
TTGCGTTTTTATTTGTTAACTGTTAATTGTCCTTGTTCAAGGATGCTGTC
TTTGACAACAGATGTTTCTTGCCTTTGATGTTCAGCAGGAAGCTAGGCG
CAAACGTTGATTGTTTGTCTGCGTAGAATCCTCTGTTTGTCATATAGCTT
GTAATCACGACATTGTTTCCTTTCGCTTGAGGTACAGCGAAGTGTGAGTA
AGTAAAGGTTACATCGTTAGGATCAAGATCCATTTTTAACACAAGGCCAG
TTTTGTTCAGCGGCTTGTATGGGCCAGTTAAAGAATTAGAAACATAACCA
AGCATGTAAATATCGTTAGACGTAATGCCGTCAATCGTCATTTTTGATCC
-continued
GCGGGAGTCAGTGAACAGATACCATTTGCCGTTCATTTTAAAGACGTTCG
CGCGTTCAATTTCATCTGTTACTGTGTTAGATGCAATCAGCGGTTTCATC
ACTTTTTTCAGTGTGTAATCATCGTTTAGCTCAATCATACCGAGAGCGCC
GTTTGCTAACTCAGCCGTGCGTTTTTATCGCTTTGCAGAACTTTTTGAC
TTTCTTGACGGAAGAATGATGTGCTTTTGCCATAGTATGCTTTGTTAAAT
AAAGATTCTTCGCCTTGGTAGCCATCTTCAGTTCCAGTGTTTGCTTCAAA
TACTAAGTATTTGTGGCCTTTATCTTCTACGTAGTGAGGATCTCTCAGCG
TATGGTTGTCGCCTGAGCTGTAGTTGCCTTCATCGATGAACTGCTGTACA
TTTTGATACGTTTTTCCGTCACCGTCAAAGATTGATTTATAATCCTCTAC
ACCGTTGATGTTCAAAGAGCTGTCTGATGCTGATACGTTAACTTGTGCAG
TTGTCAGTGTTTGTTTGCCGTAATGTTTACCGGAGAAATCAGTGTAGAAT
AAACGATTTTTCCGTCAGATGTAAATGTGGCTGAACCTGACCATTCTTG
TGTTTGGTCTTTTAGGATAGAATCATTTGCATCGAATTTGTCGCTGTCTT
TAAAGACGCGGCCAGCGTTTTTCCAGCTGTCAATAGAAGTTTCGCCGACT
TTTTGATAGAACATGTAAATCGATGTGTCATCCGCATTTTTAGGATCTCC
GGCTAATGCAAAGACGATGTGGTAGCCGTGATAGTTTGCGACAGTGCCGT
CAGCGTTTTGTAATGGCCAGCTGTCCCAAACGTCCAGGCCTTTTGCAGAA
GAGATATTTTTAATTGTGGACGAATCGAACTCAGGAACTTGATATTTTTC
ATTTTTTTGCTGTTCAGGGATTTGCAGCATATCATGGCGTGTAATATGGG
AAATGCCGTATGTTTCCTTATATGGCTTTTGGTTCGTTTCTTTCGCAAAC
GCTTGAGTTGCGCCTCCTGCCAGCAGTGCGGTAGTAAAGGTTAATACTGT
TGCTTGTTTTGCAAACTTTTTGATGTTCATCGTTCATGTCTCCTTTTTTA
TGTACTCTGTTAGCGGTCTGCTTCTTCCAGCCCTCCTGTTTGAAGATGGC
AAGTTAGTTACGCACAATAAAAAAAGACCTAAAATATGTAAGGGGTGACG
CCAAAGTATACACTTTGCCCTTTACACATTTTAGGTCTTGCCTGCTTTAT
CAGTAACAAACCCGCGCGATTTACTTTTCGACCTCATTCTATTAGACTCT
CGTTTGGATTGCAACTGGTCTATTTTCCTCTTTTGTTTGATAGAAAATCA
TAAAAGGATTTGCAGACTACGGGCCTAAAGAACTAAAAAATCTATCTGTT
TCTTTTCATTCTCTGTATTTTTATAGTTTCTGTTGCATGGGCATAAAGT
TGCCTTTTTAATCACAATTCAGAAAATATCATAATATCTCATTTCACTAA
ATAATAGTGAACGGCAGGTATATGTGATGGGTTAAAAAGGATCGATCCTC
TAGCTAGAGTCGATCTTCGCCAGCAGGGCGAGGATCGTGGCATCACCGAA
CCGCGCCGTGCGCGGGTCGTCGGTGAGCCAGAGTTTCAGCAGGCCGCCCA
GGCGGCCCAGGTCGCCATTGATGCGGGCCAGCTCGCGGACGTGCTCATAG
TCCACGACGCCCGTGATTTTGTAGCCCTGGCCGACGGCCAGCAGGTAGGC
CGACAGGCTCATGCCGGCCGCCGCCGCCTTTTCCTCAATCGCTCTTCGTT
CGTCTGGAAGGCAGTACACCTTGATAGGTGGGCTGCCCTTCCTGGTTGGC
TTGGTTTCATCAGCCATCCGCTTGCCCTCATCTGTTACGCCGGCGGTAGC
CGGCCAGCCTCGCAGAGCAGGATTCCCGTTGAGCACCGCCAGGTGCGAAT
AAGGGACAGTGAAGAAGGAACACCCGCTCGCGGGTGGGCCTACTTCACCT
ATCCTGCCCGGCTGACGCCGTTGGATACACCAAGGAAAGTCTACACGAAC
```

-continued

```
CCTTTGGCAAAATCCTGTATATCGTGCGAAAAAGGATGGATATACCGAAA
AAATCGCTATAATGACCCCGAAGCAGGGTTATGCAGCGGAAAAGCGCTGC
TTCCCTGCTGTTTTGTGGAATATCTACCGACTGGAAACAGGCAAATGCAG
GAAATTACTGAACTGAGGGGACAGGCGAGAGACGATGCCAAAGAGCTACA
CCGACGAGCTGGCCGAGTGGGTTGAATCCCGCGCGGCCAAGAAGCGCCGG
CGTGATGAGGCTGCGGTTGCGTTCCTGGCGGTGAGGGCGGATGTCGATAT
GCGTAAGGAGAAAATACCGCATCAGGCGCATGCATATTTGAATGTATTTA
GAAAAATAAACAAAAAGAGTTTGTAGAAACGCAAAAAGGCCATCCGTCAG
GATGGCCTTCTGCTTAATTTGATGCCTGGCAGTTTATGGCGGGCGTCCTG
CCCGCCACCCTCCGGGCCGTTGCTTCGCAACGTTCAAATCCGCTCCCGGC
GGATTTGTCCTACTCAGGAGAGCGTTCACCGACAAACAACAGATAAAACG
AAAGGCCCAGTCTTTCGACTGAGCCTTTCGTTTTATTTGATGCCTGGCAG
TTCCCTACTCTCGCATGGGAGACCCCACACTACCATCCGCGCTACGGCG
TTTCACTTCTGAGTTCGGCATGGGGTCAGGTGGGACCACCGCGCTACTGC
CGCCAGGCAAATTCTGTTTTATCAGACCGCTTCTGCGTTCTGATTTAATC
TGTATCAGGCTGAAAATCTTCTCTCATCCGCCAAAACAGCCAAGCTCGCC
ATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGG
CCAGTGCCAAGCTCATTACCCTGTTATCCCTACCCGGTGAATTCTCTAGA
AAGCTTCTGCAGCCATGGTCGACCCGGGGATCCGGGATTACCCTGTTATC
CCTAGAGCTTGGCGTAATCATGGTCATAGCTGTTTCCTGTGTGAAATTGT
TATCCGCTCACAATTCCACACAACATACGAGCCGGAAGCATAAAGTGTAA
AGCCTGGGGTGCCTAATGAGTGAGCTAACTCACATTAATTGCGTTGCGCT
CACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGG
TATCAGCTCACTCAAAGGCGGTAATACGGTTATCCACAGAATCAGGGGAT
AACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGG
GAAGCGTGGCGCTTTCTCATAGCTCACGCTGTAGGTATCTCAGTTCGGTG
TAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAA
GACACGACTTATCGCCACTGGCAGCAGCCACTGGTAACAGGATTAGCAGA
GCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAG
TTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAA
```

-continued

```
AAAAGGATCTCAAGAAGATCCTTTGATCTTTTCTACGGGGTCTGACGCTC
AGTGGAACGAAAACTCACGTTAAGGGATTTTGGTCATGAGATTATCAAAA
AGGATCTTCACCTAGATCCTTTTAAATTAAAAATGAAGTTTTAAATCAAT
CTAAAGTATATATGAGTAAACTTGGTCTGACAGTTACCAATGCTTAATCA
GTGAGGCACCTATCTCAGCGATCTGTCTATTTCGTTCATCCATAGTTGCC
TGACTCCCCGTCGTGTAGATAACTACGATACGGGAGGGCTTACCATCTGG
CCCCAGTGCTGCAATGATACCGCGACACCCACGCTCACCGGCTCCAGATT
TATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCC
GGTTCCCAACGATCAAGGCGAGTTACATGATCCCCCATGTTGTGCAAAAA
AGCGGTTAGCTCCTTCGGTCCTCCGATCGTTGTCAGAAGTAAGTTGGCCG
CAGTGTTATCACTCATGGTTATGGCAGCACTGCATAATTCTCTTACTGTC
ATGCCATCCGTAAGATGCTTTTCTGTGACTGGTGAGTACTCAACCAAGTC
ATTCTGAGAATAGTGTATGCGGCGACCGAGTTGCTCTTGCCCGGCGTCAA
TACGGGATAATACCGCGCCACATAGCAGAACTTTAAAAGTGCTCATCATT
GGAAAACGTTCTTCGGGGCGAAAACTCTCAAGGATCTTACCGCTGTTGAG
ATCCAGTTCGATGTAACCCACTCGTGCACCCAACTGATCTTCAGCATCTT
TTACTTTCACCAGCGTTTCTGGGTGAGCAAAAACAGGAAGGCAAAATGCC
GCAAAAAAGGGAATAAGGGCGACACGGAAATGTTGAATACTCATACTCTT
CCTTTTTCAATGGGGTGGCCGAAGAACTCCAGCATGAGATCCCCGCGCTG
GAGGATCATCCAGCCGGCGTCCCGGAAAACGATTCCGAAGCCCAACCTTT
CATAGAAGGCGGCGGTGGAATCGAAATCTCGTGATGGCAGGTTGGGCGTC
GCTTGGTCGGTCATTTCGAACCCCAGAGTCCCGCTCAGAAGAACTCGTCA
AGAAGGCGATAGAAGGCGATGCGCTGCGAATCGGGAGCGGCGATACCGTA
AAGCACGAGGAAGCGGTCAGCCCATTCGCCGCCAAGCTCTTCAGCAATAT
CACGGGTAGCCAACGCTATGTCCTGATAGCGGTCCGCCACACCCAGCCGG
CCACAGTCGATGAATCCAGAAAAGCGGCCATTTTCCACCATGATATTCGG
CAAGCAGGCATCGCCATGGGTCACGACGAGATCCTCGCCGTCGGGCATGC
GCGCCTTGAGCCTGGCGAACAGTTCGGCTGGCGCGAGCCCCTGATGCTCT
TCGTCCAGATCATCCTGATCGACAAGACCGGCTTCCATCCGAGTACGTGC
TCGCTCGATGCGATGTTTCGCTTGGTGGTCGAATGGGCAGGTAGCCGGAT
CAAGCGTATGCAGCCGCCGCATTGCATCAGCCATGATGGATACTTTCTCG
GCAGGAGCAAGGTGAGATGACAGGAGATCCTGCCCCGGCACTTCGCCCAA
TAGCAGCCAGTCCCTTCCCGCTTCAGTGACAACGTCGAGCACAGCTGCGC
AAGGAACGCCCGTCGTGGCCAGCCACGATAGCCGCGCTGCCTCGTCCTGC
AGTTCATTCAGGGCACCGGACAGGTCGGTCTTGACAAAAAGAACCGGGCG
CCCCTGCGCTGACAGCCGGAACACGGCGGCATCAGAGCAGCCGATTGTCT
GTTGTGCCCAGTCATAGCCGAATAGCCTCTCCACCCAAGCGGCCGGAGAA
CCTGCGTGCAATCCATCTTGTTCAATCATGCGAAACGATCCTCATCCTGT
```

```
CTCTTGATCAGATCTTGATCCCCTGCGCCATCAGATCCTTGGCGGAAGA
AAGCCATCCAGTTTACTTTGCAGGGCTTCCCAACCTTACCAGAGGGCGCC
CCAGCTGGCAATTCCGGTTCGCTTGCTGTCCATAAAACCGCCCAGTCTAG
CTATCGCCATGTAAGCCCACTGCAAGCTACCTGCTTTCTCTTTGCGCTTG
CGTTTTCCCTTGTCCAGATAGCCCAGTAGCTGACATTCATCCGGGGTCAG
CAGCCTTTCTGCGGACTGGCTTTCTACGTGTTCCGCTTCCTTTAGCAGCC
CTTGCGCCCTGAGTGCTTGCGGCAGCGTGAAGCTATTATTGAAGCATTTA
TCAGGGTTATTGTCTCATGAGCGGATACATATTTGAATGTATTTAGAAAA
ATAAACAAATAGGGGTTCCGCGCACATTTCCCCGAAAAGTGCCACCTGAC
GTCTAAGAAACCATTATTATCATGACATTAACCTATAAAAATAGGCGTAT
CACGAGGCGCCCTTTCGTC
```

The vector pAKE604 comprises a sacB marker gene from *Bacillus subtilis*, the sequence of which is shown in X02730. The presence of the sacB marker gene in Gram-negative bacteria may be counter-selected by growth in the presence of sucrose, i.e. a host cell harbouring the sacB gene will not grow in sucrose media. The resultant recombinant displacement vector was referred to as pCURE1. While the inventors have demonstrated the effective use of selecting for the sacB gene based on sucrose toxicity, they believe that other markers could be used. A potential problem with use of the sacB gene is that it may mutate which could cause problems during selection of the recombinant plasmid. Hence, other markers, which could be used on the recombinant nucleic acid molecule include the tetA gene with fusaric acid as the counter-selective agent (Maloy, S. R. and Nunn, D. W. (1981) J Bacteriol 145, 1110-1112). Another limitation is that the sacB counter selection should only work in Gram negative bacteria, so an alternative, more general strategy is to include a toxin gene such as hok, under the control of a tightly regulated promoter, such as the ara promoter from *E. coli*, so that addition of arabinose for example would induce the lethal gene and kill all plasmid positive bacteria. Hence, in one preferred embodiment, the nucleic acid molecule used in the method is pCURE1, substantially as illustrated in FIG. 3.

The nucleotide sequence of pCURE1 (10197 bp) is identified as SEQ ID No. 2.

```
[SEQ ID No. 2]
TCGCGCGTTTCGGTGATGACGGTGAAAACCTCTGACACATGCAGCTCCCG
GAGACGGTCACAGCTTGTCTGTAAGCGGATGCCGGGAGCAGACAAGCCCG
TCAGGGCGCGTCAGCGGGTGTTGGCGGGTGTCGGGGCTGGCTTAACTATG
CGGCATCAGAGCAGATTGTACTGAGAGTGCACCATAATCGGCATTTTCTT
TTGCGTTTTTATTTGTTAACTGTTAATTGTCCTTGTTCAAGGATGCTGTC
TTTGACAACAGATGTTTTCTTGCCTTTGATGTTCAGCAGGAAGCTAGGCG
CAAACGTTGATTGTTTGTCTGCGTAGAATCCTCTGTTTGTCATATAGCTT
GTAATCACGACATTGTTTCCTTTCGCTTGAGGTACAGCGAAGTGTGAGTA
AGTAAAGGTTACATCGTTAGGATCAAGATCCATTTTTAACACAAGGCCAG
TTTTGTTCAGCGGCTTGTATGGGCCAGTTAAAGAATTAGAAACATAACCA
AGCATGTAAATATCGTTAGACGTAATGCCGTCAATCGTCATTTTTGATCC
GCGGGAGTCAGTGAACAGATACCATTTGCCGTTCATTTTAAAGACGTTCG
CGCGTTCAATTTCATCTGTTACTGTGTTAGATGCAATCAGCGGTTTCATC
ACTTTTTTCAGTGTGTAATCATCGTTTAGCTCAATCATACCGAGAGCGCC
GTTTGCTAACTCAGCCGTGCGTTTTTATCGCTTTGCAGAAGTTTTTGAC
TTTCTTGACGGAAGAATGATGTGCTTTTGCCATAGTATGCTTTGTTAAAT
AAAGATTCTTCGCCTTGGTAGCCATCTTCAGTTCCAGTGTTTGCTTCAAA
TACTAAGTATTTGTGGCCTTTATCTTCTACGTAGTGAGGATCTCTCAGCG
TATGGTTGTCGCCTGAGCTGTAGTTGCCTTCATCGATGAACTGCTGTACA
TTTTGATACGTTTTTCCGTCACCGTCAAAGATTGATTTATAATCCTCTAC
ACCGTTGATGTTCAAAGAGCTGTCTGATGCTGATACGTTAACTTGTGCAG
TTGTCAGTGTTTGTTTGCCGTAATGTTTACCGGAGAAATCAGTGTAGAAT
AAACGGATTTTCCGTCAGATGTAAATGTGGCTGAACCTGACCATTCTTG
TGTTTGGTCTTTTAGGATAGAATCATTTGCATCGAATTTGTCGCTGTCTT
TAAAGACGCGGCCAGCGTTTTTCCAGCTGTCAATAGAAGTTTCGCCGACT
TTTTGATAGAACATGTAAATCGATGTGTCATCCGCATTTTTAGGATCTCC
GGCTAATGCAAAGACGATGTGGTAGCCGTGATAGTTTGCGACAGTGCCGT
CAGCGTTTTGTAATGGCCAGCTGTCCCAAACGTCCAGGCCTTTTGCAGAA
GAGATATTTTTAATTGTGGACGAATCGAACTCAGGAACTTGATATTTTTC
ATTTTTTTGCTGTTCAGGGATTTGCAGCATATCATGGCGTGTAATATGGG
AAATGCCGTATGTTTCCTTATATGGCTTTTGGTTCGTTTCTTTCGCAAAC
GCTTGAGTTGCGCCTCCTGCCAGCAGTGCGGTAGTAAAGGTTAATACTGT
TGCTTGTTTTGCAAACTTTTTGATGTTCATCGTTCATGTCTCCTTTTTTA
TGTACTGTGTTAGCGGTCTGCTTCTTCCAGCCCTCCTGTTTGAAGATGGC
AAGTTAGTTACGCACAATAAAAAAAGACCTAAAATATGTAAGGGGTGACG
CCAAAGTATACACTTTGCCCTTTACACATTTTAGGTCTTGCCTGCTTTAT
CAGTAACAAACCCGCGCGATTTACTTTTCGACCTCATTCTATTAGACTCT
CGTTTGGATTGCAACTGGTCTATTTTCCTCTTTTGTTTGATAGAAAATCA
TAAAAGGATTTGCAGACTACGGGCCTAAAGAACTAAAAAATCTATCTGTT
TCTTTTCATTCTCTGTATTTTTTATAGTTTCTGTTGCATGGGCATAAAGT
TGCCTTTTTAATCACAATTCAGAAAATATCATAATATCTCATTTCACTAA
ATAATAGTGAACGGCAGGTATATGTGATGGGTTAAAAAGGATCGATCCTC
TAGCTAGAGTCGATCTTCGCCAGCAGGGCGAGGATCGTGGCATCACCGAA
CCGCGCCGTGCGCGGGTCGTCGGTGAGCCAGAGTTTCAGCAGGCCGCCCA
GGCGGCCCAGGTCGCCATTGATGCGGGCCAGCTCGCGGACGTGCTCATAG
TCCACGACGCCCGTGATTTTGTAGCCCTGGCCGACGGCCAGCAGGTAGGC
CGACAGGCTCATGCCGGCCGCCGCCGCCTTTTCCTCAATCGCTCTTCGTT
CGTCTGGAAGGCAGTACACCTTGATAGGTGGGCTGCCCTTCCTGGTTGGC
TTGGTTTCATCAGCCATCCGCTTGCCCTCATCTGTTACGCCGGCGGTAGC
CGGCCAGCCTCGCAGAGCAGGATTCCCGTTGAGCACCGCCAGGTGCGAAT
AAGGGACAGTGAAGAAGGAACACCCGCTCGCGGGTGGGCCTACTTCACCT
ATCCTGCCCGGCTGACGCCGTTGGATACACCAAGGAAAGTCTACACGAAC
CCTTTGGCAAAATCCTGTATATCGTGCGAAAAAGGATGGATATACCGAAA
```

-continued

AAATCGCTATAATGACCCCGAAGCAGGGTTATGCAGCGGAAAAGCGCTGC
TTCCCTGCTGTTTTGTGGAATATCTACCGACTGGAAACAGGCAAATGCAG
GAAATTACTGAACTGAGGGGACAGGCGAGAGACGATGCCAAAGAGCTACA
CCGACGAGCTGGCCGAGTGGGTTGAATCCCGCGCGGCCAAGAAGCGCCGG
CGTGATGAGGCTGCGGTTGCGTTCCTGGCGGTGAGGGCGGATGTCGATAT
GCGTAAGGAGAAAATACCGCATCAGGCGCATGCATATTTGAATGTATTTA
GAAAAATAAACAAAAAGAGTTTGTAGAAACGCAAAAAGGCCATCCGTCAG
GATGGCCTTCTGCTTAATTTGATGCCTGGCAGTTTATGGCGGGCGTCCTG
CCCGCCACCCTCCGGGCCGTTGCTTCGCAACGTTCAAATCCGCTCCCGGC
GGATTTGTCCTACTCAGGAGAGCGTTCACCGACAAACAACAGATAAAACG
AAAGGCCCAGTCTTTCGACTGAGCCTTTCGTTTTATTTGATGCCTGGCAG
TTCCCTACTCTCGCATGGGGAGACCCCACACTACCATCGGCGCTACGGCG
TTTCACTTCTGAGTTCGGCATGGGGTCAGGTGGGACCACCGCGCTACTGC
CGCCAGGCAAATTCTGTTTTATCAGACCGCTTCTGCGTTCTGATTTAATC
TGTATCAGGCTGAAAATCTTCTCTCATCCGCCAAAACAGCCAAGCTCGCC
ATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGG
CCAGTGCCAAGCTCATTACCCTGTTATCCCTACCCGGTGAATTCCAACAC
ACACCAGACAAGAGAGCTGCGTGGTAGTTTCATGGCCTTCTTCTCCTTGC
GCAAAGCGCGGTAAGAGGCTATCCTGATGTTGTCTAAGCATGCAGGGGCC
TCGTGGGTTAATGAAAAATTAACTACGGGGCTTTTGTCCTTCTGCCACAC
AACACGGTAACAAACCACCTTCACGTCATGAGGCAGAAAGCCTCAAGCGC
CGGGCACATCATAGCCCATATACCAGCACGCTGACCACATTCACTTTTCC
TAAGCTTACATCCACAAACAGACGATAACGGCTCTCTCTTTTATAGGTGT
AAACCTTAAACTGCATTTCACCAGTCCCTGTTCTCGTCAGCAAAAGAGCC
GTTCATTTCAATAAACCGGGCGACCTCAGCCATCCCTTCCTGATTTTCCG
CTTTCCAGCGTTCGGCACGCAGACGACGGGCTTCATTCTGCATGGTTGTG
CTTACCAGACCGGAGATATTGACATCATATGCCTTGAGCAACTGATAGCT
GTCGCTGTCAACTGTCACTGTAATACGCTGCTTCATAGCACACCTCTTTT
TGACATACTTCGGGTATACATATCAGTATATATTCTTATGCCGCAAAAAT
CAGCGCGCAAATACGCATACTATTATCTGGCTTTTAGTAAGCCTTATGTA
TTTTACCTTTCGTTATGTTAACCAATAAAAATTAAAATCTGCCTTATAAA
AACAAAGCGTAATTACCGCATTCCCGTTTCGTATGGTCTAGAGGAGGCTC
GATCCAGTAAACAGATCCATGAATGATCAACAAAGGATCCATTAAAGATC
CCCATACCGCTGCAAACCTTGTCACTCATGGGCCGGGACCACGATCACAT
AAGCAGTGGCATGTTACTGATAAACTGTAACATGCTAATGATAAGCTGTA
TTCAGTAATCCATATACTGAAGTAAGTTAATGACATAAACTATGGTCAGT
ACGCCAGACTCAGCTGTTAAATACAGGCTGCAGGTTTTCTTCAGTCAGT
TAGCGGGGCTCTGACACACGATTTGCTGTTTATTCTTTTACTGTCCACAG
GCAGGAGGCTTTCTGGAAAACGAAAATTCAGACATCAAAAAACTGTTCGG

-continued

CGAGGTGGATAAGTCGTCCGGTGAGCTGGTGACACTGACACCAAACAATA
ACAACACCGTACAACCTGTGGCGCTGATGCGTCTGGGCGTTTTTGTACCG
ACCCTTAAATCACTGAAGAACAGTAAAAAAAATACACTGTCACGTACTGA
TGCCACGGAAGAGCTGACACGTCTTTCCCTGGCCCGTGCTGAGGGATTCG
ATAAGGTTGAGATCACCGGCCCCCGCCTGGATATGGATAACGATTTCAAG
ACCTGGGTGGGGATCATTCATTCCTTTGCCCGCCATAACGTAATTGGTGA
CAAAGTTGAACTGCCTTTTGTCGAGTTTGCAAAACTGTGTGGTATACCTT
CAAGCCAGTCATCACGCAGGCTGCGTGAGCGCATCAGCCCTTCCCTGAAA
CGCATTGCCGGTACCGTGATCTCCTTTTCCCGCACCGATGAGAAGCACAC
CCGGGAATACATCACCCATCTGGTACAGTCAGCCTACTACGATACTGAAC
GGGATATTGTTCAGTTACAGGCTGATCCCCGCCTTTTTGAACTGTACCAG
TTTGACAGAAAGGTCCTTCTCCAGCTTAAGGCGATTAATGCCCTGAAGCG
ACGGGAGTCCGCCCAGGCACTCTACACCTTTATAGAGCCTGCCCCGGG
ATCCGGCACCGGTATCGCTGCGCGGCTGCGTGCACGCCTCAATCTGAAG
TCTCCTGTATTTTCCCAGAACCAGACGGTCAGACGGGCAATGGAGCAGCT
GCGCGAGATTGGATATCTTGATTACACGGAGATCCAGCGGGGGCGGACAA
AACTCTTCTGCATTCACTACCGGCGTCCCCGGTTAAAAGCACCGAATGAT
GAGAGTAAGGAAAATCCGTTGCCACCTTCACCTGCGGAAAAAGTCAGTCC
GGAGATGCGGAGAAGCTTGCCCTGCTTGAGAAACTGGGCATCACGCTGG
ATGACCTGGAAAAACTCTTCAAATCCCGCTGAACATAAACTGTAGTCAGT
GAAGAGTGTTCCTTTACTGACTACAGCTTATATTATCAGGTGCAGTGAGT
GGTCTGCTCACTGCAGTTTATATTCAGTTTCCTGCAGTGCTGCCTGTAGC
TGAGCTGTCATCTGCCGGTCCCTTACGTGAGTCACCCCGTAACCTGATGC
TGAGGCATTGCTCCCTTCATAAAACATGACTTACTCACTACAGCTTATAT
ACATGCTCCAGCTTATGTTATGTCTGTTCTGCTGACCACAGCTTGTCGAC
TGAAGATCAGTCACACCATCCTGCACTTACAATGCGCAGAAGGAGCGAGC
ACAGAAAGAAGTCTTGAACTTTTCCGAGCATATAACTATACTCCCCGCAT
AGCTGAATTGTTGGCTATACGGTTTAAGTGGGCCCCGGTAATCTTCTCAG
TCGCCAAACTTTCTGAAGATTATCGGGGTTTTTGCTTTTCTGGCTCCTGT
AAATCCACATCAGAACCAGTTCCCTGCCACCTTACGGCGTGGCCAGCCAC
AAAATTCCTTAAACGATCAGTAATCTAGCACTAATCTTCTGAACACTCAA
GAATGTAAGCCCATCATCACACACATCGTTTTTGCGCTTCACTTTTTATC
AGTGCGGTCAGAACTTCAGCCTGAGTCAGGCCATCTTCATGACACATTTG
CATGAGCATGGCCTTATACTTTGGTTCAAGAAATACTTTTACTTCCTTGA
ACGAAGCTCTTTTACGGGCCACTGATAATCTTTGTTTCTCTGCATCAGAA
AGCGGATTCCCCTTTCTGTATGCTCGTTTTGCGCCAGATGAGGAAGTCAC
TGCATTTTCTGTCTGCGACATCTCGCCTCCTCAATACTTAAACAGGGATC
GTTTCGCAGAGGATACTACAGTTTTTTGAAATCAGCGACTTGAGAATTGT
GACGAAGATCCGGGATTACCCTGTTATCCCTAGAGCTTGGCGTAATCATG
GTCATAGCTGTTTCCTGTGTGAAATTGTTATCCGCTCACAATTCCACACA
ACATACGAGCCGGAAGCATAAAGTGTAAAGCCTGGGGTGCCTAATGAGTG

-continued

```
AGCTAACTCACATTAATTGCGTTGCGCTCACTGCCCGCTTTCCAGTCGGG
AAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTG
CGCTCGGTCGTTCGGCTGCGGCGAGCGGTATCAGCTCACTCAAAGGCGGT
AATACGGTTATCCACAGAATCAGGGGATAACGCAGGAAAGAACATGTGAG
CAAAAGGCCAGCAAAAGGCCAGGAACCGTAAAAAGGCCGCGTTGCTGGCG
TTTTTCCATAGGCTCCGCCCCCCTGACGAGCATCACAAAAATCGACGCTC
AAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGT
AACTATCGTCTTGAGTCCAACCCGGTAAGACACGACTTATCGCCACTGGC
AGCAGCCACTGGTAACAGGATTAGCAGAGCGAGGTATGTAGGCGGTGCTA
CAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCT
TTGATCTTTTCTACGGGGTCTGACGCTCAGTGGAACGAAAACTCACGTTA
AGGGATTTTGGTCATGAGATTATCAAAAAGGATCTTCACCTAGATCCTTT
TAAATTAAAAATGAAGTTTTAAATCAATCTAAAGTATATATGAGTAAACT
TGGTCTGACAGTTACCAATGCTTAATCAGTGAGGCACCTATCTCAGCGAT
CTGTCTATTTCGTTCATCCATAGTTGCCTGACTCCCCGTCGTGTAGATAA
CTACGATACGGGAGGGCTTACCATCTGGCCCCAGTGCTGCAATGATACCG
CGAGACCCACGCTCACCGGCTCCAGATTTATCAGCAATAAACCAGCCAGC
CGGAAGGGCCGAGCGCAGAAGTGGTCCTGCAACTTTATCCGCCTCCATCC
AGTCTATTAATTGTTGCCGGGAAGCTAGAGTAAGTAGTTCGCCAGTTAAT
AGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAG
TTACATGATCCCCCATGTTGTGCAAAAAAGCGGTTAGCTCCTTCGGTCCT
CCGATCGTTGTCAGAAGTAAGTTGGCCGCAGTGTTATCACTCATGGTTAT
GGCAGCACTGCATAATTCTCTTACTGTCATGCCATCCGTAAGATGCTTTT
CTGTGACTGGTGAGTACTCAACCAAGTCATTCTGAGAATAGTGTATGCGG
CGACCGAGTTGCTCTTGCCCGGCGTCAATACGGGATAATACCGCGCCACA
TAGCAGAACTTTAAAAGTGCTCATCATTGGAAAACGTTCTTCGGGGCGAA
AACTCTCAAGGATCTTACCGCTGTTGAGATCCAGTTCGATGTAACCCACT
CGTGCACCCAACTGATCTTCAGCATCTTTTACTTTCACCAGCGTTTCTGG
GTGAGCAAAAACAGGAAGGCAAAATGCCGCAAAAAAGGGAATAAGGGCGA
CACGGAAATGTTGAATACTCATACTCTTCCTTTTTCAATGGGGTGGGCGA
AGAACTCCAGCATGAGATCCCCGCGCTGGAGGATCATCCAGCCGGCGTCC
CGGAAAACGATTCCGAAGCCCAACCTTTCATAGAAGGCGGCGGTGGAATC
```

-continued

```
GAAATCTCGTGATGGCAGGTTGGGCGTCGCTTGGTCGGTCATTTCGAACC
CCAGAGTCCCGCTCAGAAGAACTCGTCAAGAAGGCGATAGAAGGCGATGC
GCTGCGAATCGGGAGCGGCGATACCGTAAAGCACGAGGAAGCGGTCAGCC
CATTCGCCGCCAAGCTCTTCAGCAATATCACGGGTAGCCAACGCTATGTC
CTGATAGCGGTCCGCCACACCCAGCCGGCCACAGTCGATGAATCCAGAAA
AGCGGCCATTTTCCACCATGATATTCGGCAAGCAGGCATCGCCATGGGTC
ACGACGAGATCCTCGCCGTCGGGCATGCGCGCCTTGAGCCTGGCGAACAG
TTCGGCTGGCGCGAGCCCCTGATGCTCTTCGTCCAGATCATCCTGATCGA
CAAGACCGGCTTCCATCCGAGTACGTGCTCGCTCGATGCGATGTTTCGCT
TGGTGGTCGAATGGGCAGGTAGCCGGATCAAGCGTATGCAGCCGCCGCAT
TGCATCAGCCATGATGGATACTTTCTCGGCAGGAGCAAGGTGAGATGACA
GGAGATCCTGCCCCGGCACTTCGCCCAATAGCAGCCAGTCCCTTCCCGCT
TCAGTGACAACGTCGAGCACAGCTGCGCAAGGAACGCCCGTCGTGGCCAG
CCACGATAGCCGCGCTGCCTCGTCCTGCAGTTCATTCAGGGCACCGGACA
GGTCGGTCTTGACAAAAAGAACCGGGCGCCCTGCGCTGACAGCCGGAAC
ACGGCGGCATCAGAGCAGCCGATTGTCTGTTGTGCCCAGTCATAGCCGAA
TAGCCTCTCCACCCAAGCGGCCGGAGAACCTGCGTGCAATCCATCTTGTT
CAATCATGCGAAACGATCCTCATCCTGTCTCTTGATCAGATCTTGATCCC
CTGCGCCATCAGATCCTTGGCGGCAAGAAAGCCATCCAGTTTACTTTGCA
GGGCTTCCCAACCTTACCAGAGGGCGCCCCAGCTGGCAATTCCGGTTCGC
TTGCTGTCCATAAAACCGCCCAGTCTAGCTATCGCCATGTAAGCCCACTG
CAAGCTACCTGCTTTCTCTTTGCGCTTGCGTTTTCCCTTGTCCAGATAGC
CCAGTAGCTGACATTCATCCGGGGTCAGCACCGTTTCTGCGGACTGGCTT
TCTACGTGTTCCGCTTCCTTTAGCAGCCCTTGCGCCCTGAGTGCTTGCGG
CAGCGTGAAGCTATTATTGAAGCATTTATCAGGGTTATTGTCTCATGAGC
GGATACATATTTGAATGTATTTAGAAAAATAAACAAATAGGGGTTCCGCG
CACATTTCCCCGAAAAGTGCCACCTGACGTCAAGAAACCATTATTATCA
TGACATTAACCTATAAAAATAGGCGTATCACGAGGCGCCCTTTCGTC
```

A further embodiment of the pCURE1 plasmid (10211 bp) is identified below as SEQ ID No. 28

[SEQ ID No. 28]
```
TCGCGCGTTTCGGTGATGACGGTGAAAACCTCTGACACATGCAGCTCCCG
GAGACGGTCACAGCTTGTCTGTAAGCGGATGCCGGGAGCAGACAAGCCCG
TCAGGGCGCGTCAGCGGGTGTTGGCGGGTGTCGGGGCTGGCTTAACTATG
CGGCATCAGAGCAGATTGTACTGAGAGTGCACCATAATCGGCATTTTCTT
TTGCGTTTTTATTTGTTAACTGTTAATTGTCCTTGTTCAAGGATGCTGTC
TTTGACAACAGATGTTTTCTTGCCTTTGATGTTCAGCAGGAAGCTAGGCG
CAAACGTTGATTGTTTGTCTGCGTAGAATCCTCTGTTTGTCATATAGCTT
GTAATCACGACATTGTTTCCTTTCGCTTGAGGTACAGCGAAGTGTGAGTA
AGTAAAGGTTACATCGTTAGGATCAAGATCCATTTTTAACACAAGGCCAG
TTTTGTTCAGCGGCTTGTATGGGCCAGTTAAAGAATTAGAAACATAACCA
```

```
AGCATGTAAATATCGTTAGACGTAATGCCGTCAATCGTCATTTTTGATCC
GCGGGAGTCAGTGAACAGATACCATTTGCCGTTCATTTTAAAGACGTTCG
CGCGTTCAATTTCATCTGTTACTGTGTTAGATGCAATCAGCGGTTTCATC
ACTTTTTTCAGTGTGTAATCATCGTTTAGCTCAATCATACCGAGAGCGCC
GTTTGCTAACTCAGCCGTGCGTTTTTTATCGCTTTGCAGAAGTTTTTGAC
TTTCTTGACGGAAGAATGATGTGCTTTTGCCATAGTATGCTTTGTTAAAT
AAAGATTCTTCGCCTTGGTAGCCATCTTCAGTTCCAGTGTTTGCTTCAAA
TACTAAGTATTTGTGGCCTTTATCTTCTACGTAGTGAGGATCTCTCAGCG
TATGGTTGTCGCCTGAGCTGTAGTTGCCTTCATCGATGAACTGCTGTACA
TTTTGATACGTTTTTCCGTCACCGTCAAAGATTGATTTATAATCCTCTAC
ACCGTTGATGTTCAAAGAGCTGTCTGATGCTGATACGTTAACTTGTGCAG
TTGTCAGTGTTTGTTTGCCGTAATGTTTACCGGAGAAATCAGTGTAGAAT
AAACGGATTTTTCCGTCAGATGTAAATGTGGCTGAACCTGACCATTCTTG
TGTTTGGTCTTTTAGGATAGAATCATTTGCATCGAATTTGTCGCTGTCTT
TAAAGACGCGGCCAGCGTTTTTCCAGCTGTCAATAGAAGTTTCGCCGACT
TTTTGATAGAACATGTAAATCGATGTGTCATCCGCATTTTTAGGATCTCC
GGCTAATGCAAAGACGATGTGGTAGCCGTGATAGTTTGCGACAGTGCCGT
CAGCGTTTTGTAATGGCCAGCTGTCCCAAACGTCCAGGCCTTTTGCAGAA
GAGATATTTTTAATTGTGGACGAATCGAACTCAGGAACTTGATATTTTTC
ATTTTTTTGCTGTTCAGGGATTTGCAGCATATCATGGCGTGTAATATGGG
AAATGCCGTATGTTTCCTTATATGGCTTTTGGTTCGTTTCTTTCGCAAAC
GCTTGAGTTGCGCCTCCTGCCAGCAGTGCGGTAGTAAAGGTTAATACTGT
TGCTTGTTTTGCAAACTTTTTGATGTTCATCGTTCATGTCTCCTTTTTA
TGTACTGTGTTAGCGGTCTGCTTCTTCCAGCCCTCCTGTTTGAAGATGGC
AAGTTAGTTACGCACAATAAAAAAAGACCTAAAATATGTAAGGGGTGACG
CCAAAGTATACACTTTGCCCTTTACACATTTTAGGTCTTGCCTGCTTTAT
CAGTAACAAACCCGCGCGATTTACTTTTCGACCTCATTCTATTAGACTCT
CGTTTGGATTGCAACTGGTCTATTTTCCTCTTTTGTTTGATAGAAAATCA
TAAAAGGATTTGCAGACTACGGGCCTAAAGAACTAAAAAATCTATCTGTT
TCTTTTCATTCTCTGTATTTTTATAGTTTCTGTTGCATGGGCATAAAGT
TGCCTTTTTAATCACAATTCAGAAAATATCATAATATCTCATTTCACTAA
ATAATAGTGAACGGCAGGTATATGTGATGGGTTAAAAAGGATCGATCCTC
TAGCTAGAGTCGATCTTCGCCAGCAGGGCGAGGATCGTGGCATCACCGAA
CCGCGCCGTGCGCGGTCGTCGGTGAGCCAGAGTTTCAGCAGGCCGCCCA
GGCGGCCCAGGTCGCCATTGATGCGGGCCAGCTCGCGGACGTGCTCATAG
TCCACGACGCCCGTGATTTTGTAGCCCTGGCCGACGGCCAGCAGGTAGGC
CGACAGGCTCATGCCGGCCGCCGCCGCCTTTTCCTCAATCGCTCTTCGTT
CGTCTGGAAGGCAGTACACCTTGATAGGTGGGCTGCCCTTCCTGGTTGGC
TTGGTTTCATCAGCCATCCGCTTGCCCTCATCTGTTACGCCGGCGGTAGC
CGGCCAGCCTCGCAGAGCAGGATTCCCGTTGAGCACCGCCAGGTGCGAAT
AAGGGACAGTGAAGAAGGAACACCCGCTCGCGGGTGGGCCTACTTCACCT
ATCCTGCCCGGCTGACGCCGTTGGATACACCAAGGAAAGTCTACACGAAC
CCTTTGGCAAAATCCTGTATATCGTGCGAAAAAGGATGGATATACCGAAA
AAATCGCTATAATGACCCCGAAGCAGGGTTATGCAGCGGAAAAGCGCTGC
TTCCCTGCTGTTTTGTGGAATATCTACCGACTGGAAACAGGCAAATGCAG
GAAATTACTGAACTGAGGGGACAGGCGAGAGACGATGCCAAAGAGCTACA
CCGACGAGCTGGCCGAGTGGGTTGAATCCCGCGCGGCCAAGAAGCGCCGG
CGTGATGAGGCTGCGGTTGCGTTCCTGGCGGTGAGGGCGGATGTCGATAT
GCGTAAGGAGAAAATACCGCATCAGGCGCATGCATATTTGAATGTATTTA
GAAAATAAACAAAAGAGTTTGTAGAAACGCAAAAAGGCCATCCGTCAG
GATGGCCTTCTGCTTAATTTGATGCCTGGCAGTTTATGGCGGGCGTCCTG
CCCGCCACCCTCCGGGCCGTTGCTTCGCAACGTTCAAATCCGCTCCCGGC
GGATTTGTCCTACTCAGGAGAGCGTTCACCGACAAACAACAGATAAAACG
AAAGGCCCAGTCTTTCGACTGAGCCTTTCGTTTTATTTGATGCCTGGCAG
TTCCCTACTCTCGCATGGGGAGACCCCACACTACCATCGGCGCTACGGCG
TTTCACTTCTGAGTTCGGCATGGGGTCAGGTGGGACCACCGCGCTACTGC
CGCCAGGCAAATTCTGTTTTATCAGACCGCTTCTGCGTTCTGATTTAATC
TGTATCAGGCTGAAAATCTTCTCTCATCCGCCAAAACAGCCAAGCTCGCC
ATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGG
CCAGTGCCAAGCTCATTCCCTGTTATCCCTACCCGGTGAATTCACTAGT
GATTATTCCAACACACACCAGACAAGAGAGCTGCGTGGTAGTTTCATGGC
CTTCTTCTCCTTGCGCAAAGCGCGGTAAGAGGCTATCCTGATGTTGTCTA
AGCATGCAGGGGCCTCGTGGGTTAATGAAAAATTAACTACGGGGCTTTTG
TCCTTCTGCCACACAACACGGTAACAAACCACCTTCACGTCATGAGGCAG
AAAGCCTCAAGCGCCGGGCACATCATAGCCCATATACCAGCACGCTGACC
ACATTCACTTTTCCTAAGCTTACATCCACAAACAGACGATAACGGCTCTC
TCTTTTATAGGTGTAAACCTTAAACTGCATTTCACCAGTCCCTGTTCTCG
TCAGCAAAAGAGCCGTTCATTTCAATAAACCGGGCGACCTCAGCCATCCC
TTCCTGATTTTCCGCTTTCCAGCGTTCGGCACGCAGACGACGGGCTTCAT
TCTGCATGGTTGTGCTTACCAGACCGGAGATATTGACATCATATGCCTTG
AGCAACTGATAGCTGTCGCTGTCAACTGTCACTGTAATACGCTGCTTCAT
AGCACACCTCTTTTTGACATACTTCGGGTATACATATCAGTATATATTCT
TATGCCGCAAAAATCAGCGCGCAAATACGCATACTATTATCTGGCTTTTA
GTAAGCCTTATGTATTTTACCTTTCGTTATGTTAACCAATAAAAATTAAA
ATCTGCCTTATAAAACAAAGCGTAATTACCGCATTCCCGTTTCGTATGG
TCTAGAGGAGGCTCGATCCAGTAAACAGATCCATGAATGATCAACAAAGG
ATCCATTAAAGATCCCCATACCGCTGCAAACCTTGTCACTCATGGGCCGG
GACCACGATCACATAAGCAGTGGCATGTTACTGATAAACTGTAACATGCT
AATGATAAGCTGTATTCAGTAATCCATATACTGAAGTAAGTTAATGACAT
AAACTATGGTCAGTACGCCAGACTCAGCTGTTAAATACAGGCTGCAGGTT
```

-continued

```
TTTCTTCAGTCAGTTAGCGGGGCTCTGACACACGATTTGCTGTTTATTCT
TTTACTGTCCACAGGCAGGAGGCTTTCTGGAAAACGAAAATTCAGACATC
AAAAAACTGTTCGGCGAGGTGGATAAGTCGTCCGGTGAGCTGGTGACACT
GACACCAAACAATAACAACACCGTACAACCTGTGGCGCTGATGCGTCTGG
GCGTTTTTGTACCGACCCTTAAATCACTGAAGAACAGTAAAAAAAATACA
CTGTCACGTACTGATGCCACGGAAGAGCTGACACGTCTTTCCCTGGCCCG
TGCTGAGGGATTCGATAAGGTTGAGATCACCGGCCCCCGCCTGGATATGG
ATAACGATTTCAAGACCTGGGTGGGGATCATTCATTCCTTTGCCCGCCAT
AACGTAATTGGTGACAAAGTTGAACTGCCTTTTGTCGAGTTTGCAAAACT
GTGTGGTATACCTTCAAGCCAGTCATCACGCAGGCTGCGTGAGCGCATCA
GCCCTTCCCTGAAACGCATTGCCGGTACCGTGATCTCCTTTTCCCGCACC
GATGAGAAGCACACCCGGGAATACATCACCCATCTGGTACAGTCAGCCTA
CTACGATACTGAACGGGATATTGTTCAGTTACAGGCTGATCCCCGCCTTT
TTGAACTGTACCAGTTTGACAGAAAGGTCCTTCTCCAGCTTAAGGCGATT
AATGCCCTGAAGCGACGGGAGTCCGCCCAGGCACTCTACACCTTTATAGA
GAGCCTGCCCCGGGATCCGGCACCGGTATCGCTGGCGCGGCTGCGTGCAC
GCCTCAATCTGAAGTCTCCTGTATTTTCCCAGAACCAGACGGTCAGACGG
GCAATGGAGCAGCTGCGCGAGATTGGATATCTTGATTACACGGAGATCCA
GCGGGGGCGGACAAAACTCTTCTGCATTCACTACCGGCGTCCCCGGTTAA
AAGCACCGAATGATGAGAGTAAGGAAAATCCGTTGCCACCTTCACCTGCG
GAAAAAGTCAGTCCGGAGATGGCGGAGAAGCTTGCCCTGCTTGAGAAACT
GGGCATCACGCTGGATGACCTGGAAAAACTCTTCAAATCCCGCTGAACAT
AAACTGTAGTCAGTGAAGAGTGTTCCTTTACTGACTACAGCTTATATTAT
CAGGTGCAGTGAGTGGTCTGCTCACTGCAGTTTATATTCAGTTTCCTGCA
GTGCTGCCAGTAGCTGAGCTGTCATCTGCCGGTCCCTTACGTGAGTCACC
CCGTAACCTGATGCTGAGGCATTGCTCCCTTCATAAAACATGACTTACTC
ACTACAGCTTATATACATGCTCCAGCTTATGTTATGTCTGTTCTGCTGAC
CACAGCTTGTCGACTGAAGATCAGTCACACCATCCTGCACTTACAATGCG
CAGAAGGAGCGAGCACAGAAAGAAGTCTTGAACTTTTCCGAGCATATAAC
TATACTCCCCGCATAGCTGAATTGTTGGCTATACGGTTTAAGTGGGCCCC
GGTAATCTTCTCAGTCGCCAAACTTTCTGAAGATTATCGGGGTTTTTGCT
TTTCTGGCTCCTGTAAATCCACATCAGAACCAGTTCCCTGCCACCTTACG
GCGTGGCCAGCCACAAAATTCCTTAAACGATCAGTAATCTAGCACTAATC
TTCTGAACACTCAAGAATGTAAGCCCATCATCACACACATCGTTTTTGCG
CTTCACTTTTTATCAGTGCGGTCAGAACTTCAGCCTGAGTCAGGCCATCT
TCATGACACATTTGCATGAGCATGGCCTTATACTTTGGTTCAAGAAATAC
TTTTACTTCCTTGAACGAAGCTCTTTTACGGGCCACTGATAATCTTTGTT
TCTCTGCATCAGAAAGCGGATTCCCCTTTCTGTATGCTCGTTTTGCGCCA
GATGAGGAAGTCACTGCATTTTCTGTCTGCGACATCTCGCCTCCTCAATA
CTTAAACAGGGATCGTTTCGCAGAGGATACTACAGTTTTTTGAAATCAGC
GACTTGAGAATTGTGACGAAGATCCGGGATTACCCTGTTATCCCTAGAGC
```

```
TTGGCGTAATCATGGTCATAGCTGTTTCCTGTGTGAAATTGTTATCCGCT
CACAATTCCACACAACATACGAGCCGGAAGCATAAAGTGTAAAGCCTGGG
GTGCCTAATGAGTGAGCTAACTCACATTAATTGCGTTGCGCTCACTGCCC
GCTTTCCAGTCGGGAAACCTGTCGTGCCAGCTGCATTAATGAATCGGCCA
ACGCGCGGGGAGAGGCGGTTTGCGTATTGGGCGCTCTTCCGCTTCCTCGC
TCACTGACTCGCTGCGCTCGGTCGTTCGGCTGCGGCGAGCGGTATCAGCT
CACTCAAAGGCGGTAATACGGTTATCCACAGAATCAGGGGATAACGCAGG
AAAGAACATGTGAGCAAAAGGCCAGCAAAAGGCCAGGAACCGTAAAAAGG
CCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCGT
TCGCTCCAAGCTGGGCTGTGTGCACGAACCCCCCGTTCAGCCCGACCGCT
GCGCCTTATCCGGTAACTATCGTCTTGAGTCCAACCCGGTAAGACACGAC
TTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACA
CTAGAAGGACAGTATTTGGTATCTGCGCTCTGCTGAAGCCAGTTACCTTC
GGAAAAAGAGTTGGTAGCTCTTGATCCGGCAAACAAACCACCGCTGGTAG
CGGTGGTTTTTTTGTTTGCAAGCAGCAGATTACGCGCAGAAAAAAAGGAT
CTCAAGAAGATCCTTTGATCTTTTCTACGGGGTCTGACGCTCAGTGGAAC
GAAAACTCACGTTAAGGGATTTTGGTCATGAGATTATCAAAAAGGATCTT
CACCTAGATCCTTTTAAATTAAAAATGAAGTTTTAAATCAATCTAAAGTA
TATATGAGTAAACTTGGTCTGACAGTTACCAATGCTTAATCAGTGAGGCA
CCTATCTCAGCGATCTGTCTATTTCGTTCATCCATAGTTGCCTGACTCCC
CGTCGTGTAGATAACTACGATACGGGAGGGCTTACCATCTGGCCCCAGTG
CTGCAATGATACCGCGAGACCCACGCTCACCGGCTCCAGATTTATCAGCA
ATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTA
GTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCA
ACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTA
TCACTCATGGTTATGGCAGCACTGCATAATTCTCTTACTGTCATGCCATC
CGTAAGATGCTTTTCTGTGACTGGTGAGTACTCAACCAAGTCATTCTGAG
AATAGTGTATGCGGCGACCGAGTTGCTCTTGCCCGGCGTCAATACGGGAT
AATACCGCGCCACATAGCAGAACTTTAAAAGTGCTCATCATTGGAAAACG
TTCTTCGGGGCGAAAACTCTCAAGGATCTTACCGCTGTTGAGATCCAGTT
CGATGTAACCCACTCGTGCACCCAACTGATCTTCAGCATCTTTTACTTTC
ACCAGCGTTTCTGGGTGAGCAAAAACAGGAAGGCAAAATGCCGCAAAAAA
GGGAATAAGGGCGACACGGAAATGTTGAATACTCATACTCTTCCTTTTTC
```

```
-continued
AATGGGTGGGCGAAGAACTCCAGCATGAGATCCCCGCGCTGGAGGATCA

TCCAGCCGGCGTCCCGGAAAACGATTCCGAAGCCCAACCTTTCATAGAAG

GCGGCGGTGGAATCGAAATCTCGTGATGGCAGGTTGGGCGTCGCTTGGTC

GGTCATTTCGAACCCCAGAGTCCCGCTCAGAAGAACTCGTCAAGAAGGCG

ATAGAAGGCGATGCGCTGCGAATCGGGAGCGGCGATACCGTAAAGCACGA

GGAAGCGGTCAGCCCATTCGCCGCCAAGCTCTTCAGCAATATCACGGGTA

GCCAACGCTATGTCCTGATAGCGGTCCGCCACACCCAGCCGGCCACAGTC

GATGAATCCAGAAAAGCGGCCATTTTCCACCATGATATTCGGCAAGCAGG

CATCGCCATGGGTCACGACGAGATCCTCGCCGTCGGGCATGCGCGCCTTG

AGCCTGGCGAACAGTTCGGCTGGCGCGAGCCCCTGATGCTCTTCGTCCAG

ATCATCCTGATCGACAAGACCGGCTTCCATCCGAGTACGTGCTCGCTCGA

TGCGATGTTTCGCTTGGTGGTCGAATGGGCAGGTAGCCGGATCAAGCGTA

TGCAGCCGCCGCATTGCATCAGCCATGATGGATACTTTCTCGGCAGGAGC

AAGGTGAGATGACAGGAGATCCTGCCCCGGCACTTCGCCCAATAGCAGCC

AGTCCCTTCCCGCTTCAGTGACAACGTCGAGCACAGCTGCGCAAGGAACG

CCCGTCGTGGCCAGCCACGATAGCCGCGCTGCCTCGTCCTGCAGTTCATT

CAGGGCACCGGACAGGTCGGTCTTGACAAAAAGAACCGGGCGCCCCTGCG

CTGACAGCCGGAACACGGCGGCATCAGAGCAGCCGATTGTCTGTTGTGCC

CAGTCATAGCCGAATAGCCTCTCCACCCAAGCGGCCGGAGAACCTGCGTG

CAATCCATCTTGTTCAATCATGCGAAACGATCCTCATCCTGTCTCTTGAT

CAGATCTTGATCCCCTGCGCCATCAGATCCTTGGCGGCAAGAAAGCCATC

CAGTTTACTTTGCAGGGCTTCCCAACCTTACCAGAGGGCGCCCCAGCTGG

CAATTCCGGTTCGCTTGCTGTCCATAAAACCGCCCAGTCTAGCTATCGCC

ATGTAAGCCCACTGCAAGCTACCTGCTTTCTCTTTGCGCTTGCGTTTTCC

CTTGTCCAGATAGCCCAGTAGCTGACATTCATCCGGGGTCAGCACCGTTT

CTGCGGACTGGCTTTCTACGTGTTCCGCTTCCTTTAGCAGCCCTTGCGCC

CTGAGTGCTTGCGGCAGCGTGAAGCTATTATTGAAGCATTTATCAGGGTT

ATTGTCTCATGAGCGGATACATATTTGAATGTATTTAGAAAAATAAACAA

ATAGGGGTTCCGCGCACATTTCCCCGAAAAGTGCCACCTGACGTCTAAGA

AACCATTATTATCATGACATTAACCTATAAAAATAGGCGTATCACGAGGC

GCCCTTTCGTC
```

Accordingly, in a second aspect of the invention, there is provided a recombinant vector pCURE1, substantially as illustrated in FIG. 3. Nucleic acid sequences for the pCURE1 vector are provided in SEQ ID No:2 and 28. Preferably the recombinant vector pCURE2 comprises the nucleic acid sequence provided in SEQ ID No. 28. Advantageously, pCURE1 may be used to displace an F-like plasmid (e.g. pO157) from a host cell, for example, E. coli.

The pCURE1 plasmid may be introduced into a host cell by any suitable means, for example, but conjugative transfer from a suitable donor cell (for example, S17-1), or by electroporation. Successful transformants may be readily selected for using known selection techniques, for example by plating the culture onto selective medium, which selects for transformants harbouring the displacement plasmid (e.g. medium selecting for the kanamycin gene on pCURE1).

Once the displacement plasmid has been introduced into the host cell, the endogenous plasmid (e.g. pO157) will be displaced. The method then preferably comprises displacing the displacement plasmid from the host cell, for example, by growing the bacteria in the absence of selection to allow plasmid loss and then selecting against the sacB gene on pCURE1. This results in displacement of both the endogenous pO157 plasmid and the pCURE1 displacement plasmid being displaced from the host cell.

The inventors then decided to create a derivative plasmid based on pCURE1, which derivative comprises additional replicons and PSK systems identified from DNA sequences of other F-like plasmids, such as pB171 (AB024946), p1658/97 (AF550679.1) pKDSC50 (AB040415) and pWR501 (AF348706).

Hence, in a preferred embodiment, the nucleic acid molecule comprises an antidote gene from at least one PSK system independently selected from flmA/flmB (hok/sok) from F (AP001918; 62824-62927); srnB/srnC from p1658/97 (AF550679) and pB171 (AB024946) (antisense RNA systems); and pemI/pemK from p1658/97 and pB171 (a toxin/anti-toxin system), sequences of which are shown in the sequence accessions shown in brackets. It is most preferred that the nucleic acid molecule comprises all antidote genes from each of these PSK systems.

Furthermore, preferably, the nucleic acid molecule comprises a replication system RepFIA (from F/pHCM1) and/or RepFIIA (from pKDSC50), sequences of which are shown in (AP001918, coordinates 49100-49500; and AB024946, coordinates 24400-24700). The resultant vector is referred to as pCURE2, and is capable of displacing a wide range of F-like plasmids. Hence, in another preferred embodiment, the nucleic acid molecule used in the method is pCURE2, substantially as illustrated in FIG. 4.

The nucleotide sequence of pCURE2 (12002 bp) is identified as SEQ ID No. 3.

```
[SEQ ID No. 3]
TCGCGCGTTTCGGTGATGACGGTGAAAACCTCTGACACATGCAGCTCCCG

GAGACGGTCACAGCTTGTCTGTAAGCGGATGCCGGGAGCAGACAAGCCCG

TCAGGGCGCGTCAGCGGGTGTTGGCGGGTGTCGGGGCTGGCTTAACTATG

CGGCATCAGAGCAGATTGTACTGAGAGTGCACCATAATCGGCATTTTCTT

TTGCGTTTTTATTTGTTAACTGTTAATTGTCCTTGTTCAAGGATGCTGTC

TTTGACAACAGATGTTTTCTTGCCTTTGATGTTCAGCAGGAAGCTAGGCG

CAAACGTTGATTGTTTGTCTGCGTAGAATCCTCTGTTTGTCATATAGCTT

GTAATCACGACATTGTTTCCTTTCGCTTGAGGTACAGCGAAGTGTGAGTA

AGTAAAGGTTACATCGTTAGGATCAAGATCCATTTTTAACACAAGGCCAG

TTTTGTTCAGCGGCTTGTATGGGCCAGTTAAAGAATTAGAAACATAACCA

AGCATGTAAATATCGTTAGACGTAATGCCGTCAATCGTCATTTTTGATCC

GCGGGAGTCAGTGAACAGATACCATTTGCCGTTCATTTTAAAGACGTTCG

CGCGTTCAATTTCATCTGTTACTGTGTTAGATGCAATCAGCGGTTTCATC

ACTTTTTTCAGTGTGTAATCATCGTTTAGCTCAATCATACCGAGAGCGCC

GTTTGCTAACTCAGCCGTGCGTTTTTTATCGCTTTGCAGAAGTTTTTGAC

TTTCTTGACGGAAGAATGATGTGCTTTTGCCATAGTATGCTTTGTTAAAT

AAAGATTCTTCGCCTTGGTAGCCATCTTCAGTTCCAGTGTTTGCTTCAAA
```

```
TACTAAGTATTTGTGGCCTTTATCTTCTACGTAGTGAGGATCTCTCAGCG
TATGGTTGTCGCCTGAGCTGTAGTTGCCTTCATCGATGAACTGCTGTACA
TTTTGATACGTTTTTCCGTCACCGTCAAAGATTGATTTATAATCCTCTAC
ACCGTTGATGTTCAAAGAGCTGTCTGATGCTGATACGTTAACTTGTGCAG
TTGTCAGTGTTTGTTTGCCGTAATGTTTACCGAGAAATCAGTGTAGAAT
AAACGGATTTTTCCGTCAGATGTAAATGTGGCTGAACCTGACCATTCTTG
TGTTTGGTCTTTTAGGATAGAATCATTTGCATCGAATTTGTCGCTGTCTT
TAAAGACGCGGCCAGCGTTTTTCCAGCTGTCAATAGAAGTTTCGCCGACT
TTTTGATAGAACATGTAAATCGATGTGTCATCCGCATTTTTAGGATCTCC
GGCTAATGCAAAGACGATGTGGTAGCCGTGATAGTTTGCGACAGTGCCGT
CAGCGTTTTGTAATGGCCAGCTGTCCCAAACGTCCAGGCCTTTTGCAGAA
GAGATATTTTTAATTGTGGACGAATCGAACTCAGGAACTTGATATTTTTC
ATTTTTTTGCTGTTCAGGGATTTGCAGCATATCATGGCGTGTAATATGGG
AAATGCCGTATGTTTCCTTATATGGCTTTTGGTTCGTTTCTTTCGCAAAC
GCTTGAGTTGCGCCTCCTGCCAGCAGTGCGGTAGTAAAGGTTAATACTGT
TGCTTGTTTTGCAAACTTTTTGATGTTCATCGTTCATGTCTCCTTTTTTA
TGTACTGTGTTAGCGGTCTGCTTCTTCCAGCCCTCCTGTTTGAAGATGGC
AAGTTAGTTACGCACAATAAAAAAAGACCTAAAATATGTAAGGGGTGACG
CCAAAGTATACACTTTGCCCTTTACACATTTTAGGTCTTGCCTGCTTTAT
CAGTAACAAACCCGCGCGATTTACTTTTCGACCTCATTCTATTAGACTCT
CGTTTGGATTGCAACTGGTCTATTTTCCTCTTTTGTTTGATAGAAAATCA
TAAAAGGATTTGCAGACTACGGGCCTAAAGAACTAAAAAATCTATCTGTT
TCTTTTCATTCTCTGTATTTTTATAGTTTCTGTTGCATGGGCATAAAGT
TGCCTTTTTAATCACAATTCAGAAAATATCATAATATCTCATTTCACTAA
ATAATAGTGAACGGCAGGTATATGTGATGGGTTAAAAAGGATCGATCCTC
TAGCTAGAGTCGATCTTCGCCAGCAGGGCGAGGATCGTGGCATCACCGAA
CCGCGCCGTGCGCGGGTCGTCGGTGAGCCAGAGTTTCAGCAGGCCGCCCA
GGCGGCCCAGGTCGCCATTGATGCGGGCCAGCTCGCGGACGTGCTCATAG
TCCACGACGCCCGTGATTTTGTAGCCCTGGCCGACGGCCAGCAGGTAGGC
CGACAGGCTCATGCCGGCCGCCGCGCCTTTTCCTCAATCGCTCTTCGTT
CGTCTGGAAGGCAGTACACCTTGATAGGTGGGCTGCCCTTCCTGGTTGGC
TTGGTTTCATCAGCCATCCGCTTGCCCTCATCTGTTACGCCGGCGGTAGC
CGGCCAGCCTCGCAGAGCAGGATTCCCGTTGAGCACCGCCAGGTGCGAAT
AAGGGACAGTGAAGAAGGAACACCCGCTCGCGGGTGGGCCTACTTCACCT
ATCCTGCCCGGCTGACGCCGTTGGATACACCAAGGAAAGTCTACACGAAC
CCTTTGGCAAAATCCTGTATATCGTGCGAAAAAGGATGGATATACCGAAA
AAATCGCTATAATGACCCCGAAGCAGGGTTATGCAGCGGAAAAGCGCTGC
TTCCCTGCTGTTTTGTGGAATATCTACCGACTGGAAACAGGCAAATGCAG
GAAATTACTGAACTGAGGGGACAGGCGAGAGACGATGCCAAAGAGCTACA
CCGACGAGCTGGCCGAGTGGGTTGAATCCCGCGCGGCCAAGAAGCGCCGG
CGTGATGAGGCTGCGGTTGCGTTCCTGGCGGTGAGGGCGGATGTCGATAT

GCGTAAGGAGAAAATACCGCATCAGGCGCATGCATATTTGAATGTATTTA
GAAAATAAACAAAAAGAGTTTGTAGAAACGCAAAAAGGCCATCCGTCAG
GATGGCCTTCTGCTTAATTTGATGCCTGGCAGTTTATGGCGGGCGTCCTG
CCCGCCACCCTCCGGGCCGTTGCTTCGCAACGTTCAAATCCGCTCCCGGC
GGATTTGTCCTACTCAGGAGAGCGTTCACCGACAAACAACAGATAAAACG
AAAGGCCCAGTCTTTCGACTGAGCCTTTCGTTTTATTTGATGCCTGGCAG
TTCCCTACTCTCGCATGGGAGACCCCACACTACCATCGGCGCTACGGCG
TTTCACTTCTGAGTTCGGCATGGGGTCAGGTGGGACCACCGCGCTACTGC
CGCCAGGCAAATTCTGTTTTATCAGACCGCTTCTGCGTTCTGATTTAATC
TGTATCAGGCTGAAAATCTTCTCTCATCCGCCAAAACAGCCAAGCTCGCC
ATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGG
CCAGTGCCAAGCTCATTACCCTGTTATCCCTACCCGGTGAATTCCAACAC
ACACCAGACAAGAGAGCTGCGTGGTAGTTTCATGGCCTTCTTCTCCTTGC
GCAAAGCGCGGTAAGAGGCTATCCTGATGTTGTCTAAGCATGCAGGGGCC
TCGTGGGTTAATGAAAAATTAACTACGGGGCTTTTGTCCTTCTGCCACAC
AACACGGTAACAAACCACCTTCACGTCATGAGGCAGAAAGCCTCAAGCGC
CGGGCACATCATAGCCCATATACCAGCACGCTGACCACATTCACTTTTCC
TAAGCTTACATCCACAAACAGACGATAACGGCTCTCTCTTTTATAGGTGT
AAACCTTAAACTGCATTTCACCAGTCCCTGTTCTCGTCAGCAAAAGAGCC
GTTCATTTCAATAAACCGGGCGACCTCAGCCATCCCTTCCTGATTTTCCG
CTTTCCAGCGTTCGGCACGCAGACGACGGGCTTCATTCTGCATGGTTGTG
CTTACCAGACCGGAGATATTGACATCATATGCCTTGAGCAACTGATAGCT
GTCGCTGTCAACTGTCACTGTAATACGCTGCTTCATAGCACACCTCTTTT
TGACATACTTCGGGTATACATATCAGTATATATTCTTATGCCGCAAAAAT
CAGCGCGCAAATACGCATACTATTATCTGGCTTTTAGTAAGCCTTATGTA
TTTTACCTTTCGTTATGTTAACCAATAAAAATTAAAATCTGCCTTATAAA
AACAAAGCGTAATTACCGCATTCCCGTTTCGTATGGTCTAGCACCACGCT
GGGTTTACTGTTTGGTTGAAAGTTATATTTTTATTAAACATTGTGCGTTA
AAGCCTGGTGTGTTTTTTTAGTGGATGTTATATTTAAATATAACTTTTAT
GGAGGTGAAGAATGCATACCACCCGACTGAAGAGGGTTGGCGGCTCAGTT
ATGCTGACCGTCCCACCGGCACTGCTGAATGCGCTGTCTCTGGGCACAGA
TAATGAAGTTGGCATGGTCATTGATAATGGCCGGCTGATTGTTGAGCCGT
ACAGACGCCCGCAATATTCACTGGCTGAGCTACTGGCACAGTGTGATCCG
AATGCTGAAATATCAGCTGAAGAACGAGAATGGCTGGATGCACCGGCGAC
TGGTCAGGAGGAAATCTGACATGGAAGAGGGGAAATCTGGCTTGTCTCG
CTGGATCGGGTACCTCTCGCACAGCGATTTTCGTGTCAGATAAGTAATA
TCAACAGTGTGAGACACACGATCAACACACACCAGACAAGGGAACTTCGT
GGTAGTTTCATGGCCTTCTTCTCCTTGCGCAAAGCGCGGTAAGAGGCTAT
CCTGATGTGGACTAGACATAGGGATGCCTCGTGGTGGTTAATGAAAATTA
```

-continued

```
ACTTACTACGGGCTATCTTCTTTCTGCCACACAACACGGCAACAAACCA
CCTTCACGTCATGAGGCAGAAAGCCTCAAGCGGCTAGAGGAGGCTCGATC
CAGTAAACAGATCCATGAATGATCAACAAAGGATCCATTAAAGATCCCCA
TACCGCTGCAAACCTTGTCACTCATGGGCCGGGACCACGATCACATAAGC
AGTGGCATGTTACTGATAAACTGTAACATGCTAATGATAAGCTGTATTCA
GTAATCCATATACTGAAGTAAGTTAATGACATAAACTATGGTCAGTACGC
CAGACTCAGCTGTTAAATACAGGCTGCAGGTTTTTCTTCAGTCAGTTAGC
GGGGCTCTGACACACGATTTGCTGTTTATTCTTTTACTGTCCACAGGCAG
GAGGCTTTCTGGAAAACGAAAATTCAGACATCAAAAAACTGTTCGGCGAG
GTGGATAAGTCGTCCGGTGAGCTGGTGACACTGACACCCAAACAATAACAA
CACCGTACAACCTGTGGCGCTGATGCGTCTGGGCGTTTTTGTACCGACCC
TTAAATCACTGAAGAACAGTAAAAAAAATACACTGTCACGTACTGATGCC
ACGGAAGAGCTGACACGTCTTTCCCTGGCCCGTGCTGAGGGATTCGATAA
GGTTGAGATCACCGGCCCCGCCTGGATATGGATAACGATTTCAAGACCT
GGGTGGGGATCATTCATTCCTTTGCCCGCCATAACGTAATTGGTGACAAA
GTTGAACTGCCTTTTGTCGAGTTTGCAAAACTGTGTGGTATACCTTCAAG
CCAGTCATCACGCAGGCTGCGTGAGCGCATCAGCCCTTCCCTGAAACGCA
TTGCCGGTACCGTGATCTCCTTTTCCCGCACCGATGAGAAGCACACCCGG
GAATACATCACCCATCTGGTACAGTCAGCCTACTACGATACTGAACGGGA
TATTGTTCAGTTACAGGCTGATCCCCGCCTTTTTGAACTGTACCAGTTTG
ACAGAAAGGTCCTTCTCCAGCTTAAGGCGATTAATGCCCTGAAGCGACGG
GAGTCCGCCCAGGCACTCTACACCTTTATAGAGAGCCTGCCCCGGGATCC
GGCACCGGTATCGCTGGCGCGGCTGCGTGCACGCCTCAATCTGAAGTCTC
CTGTATTTTCCCAGAACCAGACGGTCAGACGGGCAATGGAGCAGCTGCGC
GAGATTGGATATCTTGATTACACGGAGATCCAGCGGGGGCGGACAAAACT
CTTCTGCATTCACTACCGGCGTCCCCGGTTAAAAGCACCGAATGATGAGA
GTAAGGAAAATCCGTTGCCACCTTCACCTGCGGAAAAAGTCAGTCCGGAG
ATGGCGGAGAAGCTTGCCCTGCTTGAGAAACTGGGCATCACGCTGGATGA
CCTGGAAAAACTCTTCAAATCCCGCTGAACATAAACTGTAGTCAGTGAAG
AGTGTTCCTTTACTGACTACAGCTTATATTATCAGGTGCAGTGAGTGGTC
TGCTCACTGCAGTTTATATTCAGTTTCCTGCAGTGCTGCCTGTAGCTGAG
CTGTCATCTGCCGGTCCCTTACGTGAGTCACCCCGTAACCTGATGCTGAG
GCATTGCTCCCTTCATAAAACATGACTTACTCACTACAGCTTATATACAT
GCTCCAGCTTATGTTATGTCTGTTCTGCTGACCACAGCTTGTCGAGGGAA
CGGACTGGAAACAGACGTACTGACATCCCAGGAAACGATCTTGAAACGTA
AACCGTGCGCCAACACAGGTTACGTTCATAAAGTAAGTCGCTGATTTTAG
AAATCTGTAGTATTCTCTGCAAACGATCTAGGTTTGATCCTTGAGGGAGAC
AGAGATGTCGCAGATTGAAAATGCAGTAACTTCCTCATCGAAACGCATTT
ACAGAAAGGGTAATCCCTTATCTTCCGCTGAGAAGAAGAGATTATCTATT
TCACGAAAAAGACGACGCATAAAGAGCTCAATGTTTTCATACAAACAT
ACATAAAGAAAGCTTGCAGCAGCTTTGTGAAGAGACTGGAACTACTCAGG
```

-continued

```
CTCAAATGATTGAGCTACTAATTGAACGGGAAATGGCTAAAAGAGCCTGA
GATAAGAAGGTGAATGAGTAACTTTCTTGATCGTCTCGTCAGTGAGTGTT
AGATTGCTGATCGTCTAAAGAATTTTGATGGCTGGCCACGCCGTAAGGTG
GCAGGGAACTGGTTCTGATGAGGTGCCTACCCGGGACCAGAAAAGCAAAA
ACCCCGATAATCTTCTCATTTCTTGGCGGGAACGAAAGATTAACGGGGCC
TACTTAAACTGTATAGCCACCAATCAGGCTATGCAGGGAGTATAGTTTTA
TGCTCAGAAAATTTCAATACTTGTTTCTGTGGCATTTACTCCTTCCGTGC
ATTGTAAGTGCAGGCAGAAGTGACTGACACCCGAACACTGTTCACTCATT
ACCGACAGGGGATCCGCCAGACGACTCATATCGTATTTTCCTTCCGCGAT
ATCACTTCCATGACGACAGGATAGTCTGAGGGTTATCTGTCACAGATTTG
AGGGTGGTTCGTCACATTTGTTCTGACCTACTGAGGGTAATTTGTCACAG
TTTTGCTGTTTCCTTCAGCCTGCATGGATTTTCTCATACTTTTTGAACTG
TAATTTTTAAGGAAGCCAAATTTGAGGGCAGTTTGTCACAGTTGATTTCC
TTCTCTTTCCCTTCGTCATGTGACCTGATATCGGGGGTTAGTTCGTCATC
ATTGATGAGGGTTGATTATCACAGTTTATTACTCTGAATTGGCTATCCGC
TCGACTGAAGATCAGTCACACCATCCTGCACTTACAATGCGCAGAAGGAG
CGAGCACAGAAAGAAGTCTTGAACTTTTCCGAGCATATAACTATACTCCC
CGCATAGCTGAATTGTTGGCTATACGGTTTAAGTGGGCCCCGGTAATCTT
CTCAGTCGCCAAACTTTCTGAAGATTATCGGGGTTTTTGCTTTTCTGGCT
CCTGTAAATCCACATCAGAACCAGTTCCCTGCCACCTTACGGCGTGGCCA
GCCACAAAATTCCTTAAACGATCAGTAATCTAGCACTAATCTTCTGAACA
CTCAAGAATGTAAGCCCATCATCACACACATCGTTTTTGCGCTTCACTTT
TTATCAGTGCGGTCAGAACTTCAGCCTGAGTCAGGCCATCTTCATGACAC
ATTTGCATGAGCATGGCCTTATACTTTGGTTCAAGAAATACTTTTACTTC
CTTGAACGAAGCTCTTTTACGGGCCACTGATAATCTTTGTTTCTCTGCAT
CAGAAAGCGGATTCCCCTTTCTGTATGCTCGTTTTGCGCCAGATGAGGAA
GTCACTGCATTTTCTGTCTGCGACATCTCGCCTCCTCAATACTTAAACAG
GGATCGTTTCGCAGAGGATACTACAGTTTTTTGAAATCAGCGACTTGAGA
ATTGTGACGAAGATCCGGGATTACCCTGTTATCCCTAGAGCTTGGCGTAA
TCATGGTCATAGCTGTTTCCTGTGTGAAATTGTTATCCGCTCACAATTCC
ACACAACATACGAGCCGGAAGCATAAAGTGTAAAGCCTGGGGTGCCTAAT
GAGTGAGCTAACTCACATTAATTGCGTTGCGCTCACTGCCCGCTTTCCAG
TCGGGAAACCTGTCGTGCCAGCTGCATTAATGAATCGGCCAACGCGCGGG
GAGAGGCGGTTTGCGTATTGGGCGCTCTTCCGCTTCCTCGCTCACTGACT
CGCTGCGCTCGGTCGTTCGGCTGCGGCGAGCGGTATCAGCTCACTCAAAG
GCGGTAATACGGTTATCCACAGAATCAGGGGATAACGCAGGAAAGAACAT
GTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGA
CGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCT
```

```
CATAGCTCACGCTGTAGGTATCTCAGTTCGGTGTAGGTCGTTCGCTCCAA
GCTGGGCTGTGTGCACGAACCCCCCGTTCAGCCCGACCGCTGCGCCTTAT
CCGGTAACTATCGTCTTGAGTCCAACCCGGTAAGACACGACTTATCGCCA
CTGGCAGCAGCCACTGGTAACAGGATTAGCAGAGCGAGGTATGTAGGCGG
TGCTACAGAGTTCTTGAAGTGGTGGCCTAACTACGGCTACACTAGAAGGA
CAGTATTTGGTATCTGCGCTCTGCTGAAGCCAGTTACCTTCGGAAAAAGA
GTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCA
CGTTAAGGGATTTTGGTCATGAGATTATCAAAAAGGATCTTCACCTAGAT
CCTTTTAAATTAAAAATGAAGTTTTAAATCAATCTAAAGTATATATGAGT
AAACTTGGTCTGACAGTTACCAATGCTTAATCAGTGAGGCACCTATCTCA
GCGATCTGTCTATTTCGTTCATCCATAGTTGCCTGACTCCCCGTCGTGTA
GATAACTACGATACGGGAGGGCTTACCATCTGGCCCCAGTGCTGCAATGA
TACCGCGAGACCCACGCTCACCGGCTCCAGATTTATCAGCAATAAACCAG
CCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAG
TTAATAGTTTGCGCAACGTTGTTGCCATTGCTACAGGCATCGTGGTGTCA
CGCTCGTCGTTTGGTATGGCTTCATTCAGCTCCGGTTCCCAACGATCAAG
GCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATG
GTTATGGCAGCACTGCATAATTCTCTTACTGTCATGCCATCCGTAAGATG
CTTTTCTGTGACTGGTGAGTACTCAACCAAGTCATTCTGAGAATAGTGTA
TGCGGCGACCGAGTTGCTCTTGCCCGGCGTCAATACGGGATAATACCGCG
CCACATAGCAGAACTTTAAAAGTGCTCATCATTGGAAAACGTTCTTCGGG
GCGAAAACTCTCAAGGATCTTACCGCTGTTGAGATCCAGTTCGATGTAAC
CCACTCGTGCACCCAACTGATCTTCAGCATCTTTTACTTTCACCAGCGTT
TCTGGGTGAGCAAAAACAGGAAGGCAAAATGCCGCAAAAAAGGGAATAAG
GGCGACACGGAAATGTTGAATACTCATACTCTTCCTTTTTCAATGGGGTG
GGCGAAGAACTCCAGCATGAGATCCCCGCGCTGGAGGATCATCCAGCCGG
CGTCCCGGAAAACGATTCCGAAGCCCAACCTTTCATAGAAGGCGGCGGTG
GAATCGAAATCTCGTGATGGCAGGTTGGGCGTCGCTTGGTCGGTCATTTC
GAACCCCAGAGTCCCGCTCAGAAGAACTCGTCAAGAAGGCGATAGAAGGC
GATGCGCTGCGAATCGGGAGCGGCGATACCGTAAAGCACGAGGAAGCGGT
CAGCCCATTCGCCGCCAAGCTCTTCAGCAATATCACGGGTAGCCAACGCT
ATGTCCTGATAGCGGTCCGCCACACCCAGCCGGCCACAGTCGATGAATCC
AGAAAAGCGGCCATTTTCCACCATGATATTCGGCAAGCAGGCATCGCCAT
GGGTCACGACGAGATCCTCGCCGTCGGGCATGCGCGCCTTGAGCCTGGCG
AACAGTTCGGCTGGCGCGAGCCCCTGATGCTCTTCGTCCAGATCATCCTG
ATCGACAAGACCGGCTTCCATCCGAGTACGTGCTCGCTCGATGCGATGTT
TCGCTTGGTGGTCGAATGGGCAGGTAGCCGGATCAAGCGTATGCAGCCGC
```

```
CGCATTGCATCAGCCATGATGGATACTTTCTCGGCAGGAGCAAGGTGAGA
TGACAGGAGATCCTGCCCCGGCACTTCGCCCAATAGCAGCCAGTCCCTTC
CCGCTTCAGTGACAACGTCGAGCACAGCTGCGCAAGGAACGCCCGTCGTG
GCCAGCCACGATAGCCGCGCTGCCTCGTCCTGCAGTTCATTCAGGGCACC
GGACAGGTCGGTCTTGACAAAAGAACCGGGCGCCCCTGCGCTGACAGCC
GGAACACGGCGGCATCAGAGCAGCCGATTGTCTGTTGTGCCCAGTCATAG
CCGAATAGCCTCTCCACCCAAGCGGCCGGAGAACCTGCGTGCAATCCATC
TTGTTCAATCATGCGAAACGATCCTCATCCTGTCTCTTGATCAGATCTTG
ATCCCCTGCGCCATCAGATCCTTGGCGGCAAGAAAGCCATCCAGTTTACT
TTGCAGGGCTTCCCAACCTTACCAGAGGGCGCCCCAGCTGGCAATTCCGG
TTCGCTTGCTGTCCATAAAACCGCCCAGTCTAGCTATCGCCATGTAAGCC
CACTGCAAGCTACCTGCTTTCTCTTTGCGCTTGCGTTTTCCCTTGTCCAG
ATAGCCCAGTAGCTGACATTCATCCGGGGTCAGCACCGTTTCTGCGGACT
GGCTTTCTACGTGTTCCGCTTCCTTTAGCAGCCCTTGCGCCCTGAGTGCT
TGCCGGCAGCGTGAAGCTATTATTGAAGCATTTATCAGGGTTATTGTCTCA
TGAGCGGATACATATTTGAATGTATTTAGAAAAATAAACAAATAGGGGTT
CCGCGCACATTTCCCCGAAAAGTGCCACCTGACGTCAAGAAACCATTAT
TATCATGACATTAACCTATAAAAATAGGCGTATCACGAGGCGCCCTTTCG
TC
```

A further embodiment of the pCURE2 plasmid (12016 bp) is identified below as SEQ ID No. 29.

[SEQ ID No. 29]
```
TCGCGCGTTTCGGTGATGACGGTGAAAACCTCTGACACATGCAGCTCCCG
GAGACGGTCACAGCTTGTCTGTAAGCGGATGCCGGGAGCAGACAAGCCCG
TCAGGGCGCGTCAGCGGGTGTTGGCGGGTGTCGGGGCTGGCTTAACTATG
CGGCATCAGAGCAGATTGTACTGAGAGTGCACCATAATCGGCATTTTCTT
TTGCGTTTTTATTTGTTAACTGTTAATTGTCCTTGTTCAAGGATGCTGTC
TTTGACAACAGATGTTTTCTTGCCTTTGATGTTCAGCAGGAAGCTAGGCG
CAAACGTTGATTGTTTGTCTGCGTAGAATCCTCTGTTTGTCATATAGCTT
GTAATCACGACATTGTTTCCTTTCGCTTGAGGTACAGCGAAGTGTGAGTA
AGTAAAGGTTACATCGTTAGGATCAAGATCCATTTTTAACACAAGGCCAG
TTTTGTTCAGCGGCTTGTATGGGCCAGTTAAAGAATTAGAAACATAACCA
AGCATGTAAATATCGTTAGACGTAATGCCGTCAATCGTCATTTTTGATCC
GCGGGAGTCAGTGAACAGATACCATTTGCCGTTCATTTTAAAGACGTTCG
CGCGTTCAATTTCATCTGTTACTGTGTTAGATGCAATCAGCGGTTTCATC
ACTTTTTTCAGTGTGTAATCATCGTTTAGCTCAATCATACCGAGAGCGCC
GTTTGCTAACTCAGCCGTGCGTTTTTATCGCTTTGCAGAAGTTTTTGAC
TTTCTTGACGGAAGAATGATGTGCTTTTGCCATAGTATGCTTTGTTAAAT
AAAGATTCTTCGCCTTGGTAGCCATCTTCAGTTCCAGTGTTTGCTTCAAA
TACTAAGTATTTGTGGCCTTTATCTTCTACGTAGTGAGGATCTCTCAGCG
TATGGTTGTCGCCTGAGCTGTAGTTGCCTTCATCGATGAACTGCTGTACA
```

-continued

TTTTGATACGTTTTTCCGTCACCGTCAAAGATTGATTTATAATCCTCTAC
ACCGTTGATGTTCAAAGAGCTGTCTGATGCTGATACGTTAACTTGTGCAG
TTGTCAGTGTTTGTTTGCCGTAATGTTTACCGGAGAAATCAGTGTAGAAT
AAACGGATTTTTCCGTCAGATGTAAATGTGGCTGAACCTGACCATTCTTG
TGTTTGGTCTTTTAGGATAGAATCATTTGCATCGAATTTGTCGCTGTCTT
TAAAGACGCGGCCAGCGTTTTTCCAGCTGTCAATAGAAGTTTCGCCGACT
TTTTGATAGAACATGTAAATCGATGTGTCATCCGCATTTTTAGGATCTCC
GGCTAATGCAAAGACGATGTGGTAGCCGTGATAGTTTGCGACAGTGCCGT
CAGCGTTTTGTAATGGCCAGCTGTCCCAAACGTCCAGGCCTTTTGCAGAA
GAGATATTTTTAATTGTGGACGAATCGAACTCAGGAACTTGATATTTTTC
ATTTTTTTGCTGTTCAGGGATTTGCAGCATATCATGGCGTGTAATATGGG
AAATGCCGTATGTTTCCTTATATGGCTTTTGGTTCGTTTCTTTCGCAAAC
GCTTGAGTTGCGCCTCCTGCCAGCAGTGCGGTAGTAAAGGTTAATACTGT
TGCTTGTTTTGCAAACTTTTTGATGTTCATCGTTCATGTCTCCTTTTTA
TGTACTGTGTTAGCGGTCTGCTTCTTCCAGCCCTCCTGTTTGAAGATGGC
AAGTTAGTTACGCACAATAAAAAAAGACCTAAAATATGTAAGGGGTGACG
CCAAAGTATACACTTTGCCCTTTACACATTTTAGGTCTTGCCTGCTTTAT
CAGTAACAAACCCGCGCGATTTACTTTTCGACCTCATTCTATTAGACTCT
CGTTTGGATTGCAACTGGTCTATTTTCCTCTTTTGTTTGATAGAAAATCA
TAAAAGGATTTGCAGACTACGGGCCTAAAGAACTAAAAAATCTATCTGTT
TCTTTTCATTCTCTGTATTTTTTATAGTTTCTGTTGCATGGGCATAAAGT
TGCCTTTTTAATCACAATTCAGAAAATATCATAATATCTCATTTCACTAA
ATAATAGTGAACGGCAGGTATATGTGATGGGTTAAAAAGGATCGATCCTC
TAGCTAGAGTCGATCTTCGCCAGCAGGGCGAGGATCGTGGCATCACCGAA
CCGCGCCGTGCGCGGGTCGTCGGTGAGCCAGAGTTTCAGCAGGCCGCCCA
GGCGGCCCAGGTCGCCATTGATGCGGGCCAGCTCGCGGACGTGCTCATAG
TCCACGACGCCCGTGATTTTGTAGCCCTGGCCGACGGCCAGCAGGTAGGC
CGACAGGCTCATGCCGGCCGCCGCCGCCTTTTCCTCAATCGCTCTTCGTT
CGTCTGGAAGGCAGTACACCTTGATAGGTGGGCTGCCCTTCCTGGTTGGC
TTGGTTTCATCAGCCATCCGCTTGCCCTCATCTGTTACGCCGGCGGTAGC
CGGCCAGCCTCGCAGAGCAGGATTCCCGTTGAGCACCGCCAGGTGCGAAT
AAGGGACAGTGAAGAAGGAACACCCGCTCGCGGGTGGGCCTACTTCACCT
ATCCTGCCCGGCTGACGCCGTTGGATACACCAAGGAAAGTCTACACGAAC
CCTTTGGCAAAATCCTGTATATCGTGCGAAAAAGGATGGATATACCGAAA
AAATCGCTATAATGACCCCGAAGCAGGGTTATGCAGCGGAAAAGCGCTGC
TTCCCTGCTGTTTTGTGGAATATCTACCGACTGGAAACAGGCAAATGCAG
GAAATTACTGAACTGAGGGGACAGGCGAGAGACGATGCCAAAGAGCTACA
CCGACGAGCTGGCCGAGTGGGTTGAATCCCGCGCGGCCAAGAAGCGCCGG
CGTGATGAGGCTGCGGTTGCGTTCCTGGCGGTGAGGGCGGATGTCGATAT
GCGTAAGGAGAAAATACCGCATCAGGCGCATGCATATTTGAATGTATTTA
GAAAAATAAACAAAAAGAGTTTGTAGAAACGCAAAAAGGCCATCCGTCAG

-continued

GATGGCCTTCTGCTTAATTTGATGCCTGGCAGTTTATGGCGGGCGTCCTG
CCCGCCACCCTCCGGGCCGTTGCTTCGCAACGTTCAAATCCGCTCCCGGC
GGATTTGTCCTACTCAGGAGAGCGTTCACCGACAAACAACAGATAAAACG
AAAGGCCCAGTCTTTCGACTGAGCCTTTCGTTTTATTTGATGCCTGGCAG
TTCCCTACTCTCGCATGGGAGACCCCACACTACCATCGGCGCTACGGCG
TTTCACTTCTGAGTTCGGCATGGGGTCAGGTGGGACCACCGCGCTACTGC
CGCCAGGCAAATTCTGTTTTATCAGACCGCTTCTGCGTTCTGATTTAATC
TGTATCAGGCTGAAAATCTTCTCTCATCCGCCAAAACAGCCAAGCTCGCC
ATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGG
CCAGTGCCAAGCTCATTACCCTGTTATCCCTACCCGGTGAATTCACTAGT
GATTATTCCAACACACACCAGACAAGAGAGCTGCGTGGTAGTTTCATGGC
CTTCTTCTCCTTGCGCAAAGCGCGGTAAGAGGCTATCCTGATGTTGTCTA
AGCATGCAGGGGCCTCGTGGGTTAATGAAAAATTAACTACGGGGCTTTTG
TCCTTCTGCCACACAACACGGTAACAAACCACCTTCACGTCATGAGGCAG
AAAGCCTCAAGCGCCGGGCACATCATAGCCCATATACCAGCACGCTGACC
ACATTCACTTTTCCTAAGCTTACATCCACAAACAGACGATAACGGCTCTC
TCTTTTATAGGTGTAAACCTTAAACTGCATTTCACCAGTCCCTGTTCTCG
TCAGCAAAAGAGCCGTTCATTTCAATAAACCGGGCGACCTCAGCCATCCC
TTCCTGATTTTCCGCTTTCCAGCGTTCGGCACGCAGACGACGGGCTTCAT
TCTGCATGGTTGTGCTTACCAGACCGGAGATATTGACATCATATGCCTTG
AGCAACTGATAGCTGTCGCTGTCAACTGTCACTGTAATACGCTGCTTCAT
AGCACACCTCTTTTTGACATACTTCGGGTATACATATCAGTATATATTCT
TATGCCGCAAAAATCAGCGCGCAAATACGCATACTATTATCTGGCTTTTA
GTAAGCCTTATGTATTTTACCTTTCGTTATGTTAACCAATAAAAATTAAA
ATCTGCCTTATAAAACAAAGCGTAATTACCGCATTCCCGTTTCGTATGG
TCTAGCACCACGCTGGGTTTACTGTTTGGTTGAAAGTTATATTTTTATTA
AACATTGTGCGTTAAAGCCTGGTGTGTTTTTTTAGTGGATGTTATATTTA
AATATAACTTTTATGGAGGTGAAGAATGCATACCACCCGACTGAAGAGGG
TTGGCGGCTCAGTTATGCTGACCGTCCCACCGGCACTGCTGAATGCGCTG
TCTCTGGGCACAGATAATGAAGTTGGCATGGTCATTGATAATGGCCGGCT
GATTGTTGAGCCGTACAGACGCCCGCAATATTCACTGGCTGAGCTACTGG
CACAGTGTGATCCGAATGCTGAAATATCAGCTGAAGAACGAGAATGGCTG
GATGCACCGGCGACTGGTCAGGAGGAAATCGACATGGAAAGAGGGGAAA
TCTGGCTTGTCTCGCTGGATCGGGTACCTCTCGCACAGCGATTTTCGTGT
CAGATAAGTGAATATCAACAGTGTGAGACACACGATCAACACACACCAGA
CAAGGGAACTTCGTGGTAGTTTCATGGCCTTCTTCTCCTTGCGCAAAGCG
CGGTAAGAGGCTATCCTGATGTGGACTAGACATAGGGATGCCTCGTGGTG
GTTAATGAAAATTAACTTACTACGGGGCTATCTTCTTTCTGCCACACAAC
ACGGCAACAAACCACCTTCACGTCATGAGGCAGAAAGCCTCAAGCGGCTA

-continued

GAGGAGGCTCGATCCAGTAAACAGATCCATGAATGATCAACAAAGGATCC
ATTAAAGATCCCCATACCGCTGCAAACCTTGTCACTCATGGGCCGGGACC
ACGATCACATAAGCAGTGGCATGTTACTGATAAACTGTAACATGCTAATG
ATAAGCTGTATTCAGTAATCCATATACTGAAGTAAGTTAATGACATAAAC
TATGGTCAGTACGCCAGACTCAGCTGTTAAATACAGGCTGCAGGTTTTTC
TTCAGTCAGTTAGCGGGCTCTGACACACGATTTGCTGTTTATTCTTTTA
CTGTCCACAGGCAGGAGGCTTTCTGGAAAACGAAAATTCAGACATCAAAA
AACTGTTCGGCGAGGTGGATAAGTCGTCCGGTGAGCTGGTGACACTGACA
CCAAACAATAACAACACCGTACAACCTGTGGCGCTGATGCGTCTGGGCGT
TTTTGTACCGACCCTTAAATCACTGAAGAACAGTAAAAAAAATACACTGT
CACGTACTGATGCCACGGAAGAGCTGACACGTCTTTCCCTGGCCCGTGCT
GAGGGATTCGATAAGGTTGAGATCACCGGCCCCCGCCTGGATATGGATAA
CGATTTCAAGACCTGGGTGGGGATCATTCATTCCTTTGCCCGCCATAACG
TAATTGGTGACAAAGTTGAACTGCCTTTTGTCGAGTTTGCAAAACTGTGT
GGTATACCTTCAAGCCAGTCATCACGCAGGCTGCGTGAGCGCATCAGCCC
TTCCCTGAAACGCATTGCCGGTACCGTGATCTCCTTTTCCCGCACCGATG
AGAAGCACACCCGGAATACATCACCCATCTGGTACAGTCAGCCTACTAC
GATACTGAACGGGATATTGTTCAGTTACAGGCTGATCCCCGCCTTTTTGA
ACTGTACCAGTTTGACAGAAAGGTCCTTCTCCAGCTTAAGGCGATTAATG
CCCTGAAGCGACGGGAGTCCGCCCAGGCACTCTACACCTTTATAGAGAGC
CTGCCCCGGGATCCGGCACCGGTATCGCTGGCGCGGCTGCGTGCACGCCT
CAATCTGAAGTCTCCTGTATTTTCCCAGAACCAGACGGTCAGACGGGCAA
TGGAGCAGCTGCGCGAGATTGGATATCTTGATTACAGGAGATCCAGCGG
GGGCGGACAAAACTCTTCTGCATTCACTACCGGCGTCCCCGGTTAAAAGC
ACCGAATGATGAGAGTAAGGAAAATCCGTTGCCACCTTCACCTGCGGAAA
AAGTCAGTCCGGAGATGGCGGAGAAGCTTGCCCTGCTTGAGAAACTGGGC
ATCACGCTGGATGACCTGGAAAAACTCTTCAAATCCCGCTGAACATAAAC
TGTAGTCAGTGAAGAGTGTTCCTTTACTGACTACAGCTTATATTATCAGG
TGCAGTGAGTGGTCTGCTCACTGCAGTTTATATTCAGTTTCCTGCAGTGC
TGCCAGTAGCTGAGCTGTCATCTGCCGGTCCCTTACGTGAGTCACCCCGT
AACCTGATGCTGAGGCATTGCTCCCTTCATAAAACATGACTTACTCACTA
CAGCTTATATACATGCTCCAGCTTATGTTATGTCTGTTCTGCTGACCACA
GCTTGTCGAGGGAACGGACTGGAAACAGACGTACTGACATCCCAGGAAAC
GATCTTGAAACGTAAACCGTGCGCCAACACAGGTTACGTTCATAAAGTAA
GTCGCTGATTTTAGAAATCTGTAGTATTCTCTGCAAACGATCTAGGTTTG
ATCCTTGAGGAGACAGAGATGTCGCAGATTGAAAATGCAGTAACTTCCTC
ATCGAAACGCATTTACAGAAAGGGTAATCCCTTATCTTCCGCTGAGAAGA
AGAGATTATCTATTTCACGAAAAAAGACGACGCATAAAGAGCTCAATGTT
TTCATACAAAACATACATAAAGAAAGCTTGCAGCAGCTTTGTGAAGAGAC
TGGAACTACTCAGGCTCAAATGATTGAGCTACTAATTGAACGGGAAATGG
CTAAAAGAGCCTGAGATAAGAAGGTGAATGAGTAACTTTCTTGATCGTCT

-continued

CGTCAGTGAGTGTTAGATTGCTGATCGTCTAAAGAATTTTGATGGCTGGC
CACGCCGTAAGGTGGCAGGGAACTGGTTCTGATGAGGTGCCTACCCGGGA
CCAGAAAAGCAAAACCCCGATAATCTTCTCATTTCTTGGCGGGAACGAA
AGATTAACGGGCCTACTTAAACTGTATAGCCACCAATCAGGCTATGCAG
GGAGTATAGTTTTATGCTCAGAAAATTTCAATACTTGTTTCTGTGGCATT
TACTCCTTCCGTGCATTGTAAGTGCAGGCAGAAGTGACTGACACCCGAAC
ACTGTTCACTCATTACCGACAGGGGATCCGCCAGACGACTCATATCGTAT
TTTCCTTCCGCGATATCACTTCCATGACGACAGGATAGTCTGAGGGTTAT
CTGTCACAGATTTGAGGGTGGTTCGTCACATTTGTTCTGACCTACTGAGG
GTAATTTGTCACAGTTTTGCTGTTTCCTTCAGCCTGCATGGATTTTCTCA
TACTTTTTGAACTGTAATTTTTAAGGAAGCCAAATTTGAGGGCAGTTTGT
CACAGTTGATTTCCTTCTCTTTCCCTTCGTCATGTGACCTGATATCGGGG
GTTAGTTCGTCATCATTGATGAGGGTTGATTATCACAGTTTATTACTCTG
AATTGGCTATCCGCTCGACTGAAGATCAGTCACACCATCCTGCACTTACA
ATGCGCAGAAGGAGCGAGCACAGAAAGAAGTCTTGAACTTTTCCGAGCAT
ATAACTATACTCCCCGCATAGCTGAATTGTTGGCTATACGGTTTAAGTGG
GCCCCGGTAATCTTCTCAGTCGCCAAACTTTCTGAAGATTATCGGGGTTT
TTGCTTTTCTGGCTCCTGTAAATCCACATCAGAACCAGTTCCCTGCCACC
TTACGCGTGGCCAGCCACAAAATTCCTTAAACGATCAGTAATCTAGCAC
TAATCTTCTGAACACTCAAGAATGTAAGCCCATCATCACACACATCGTTT
TTGCGCTTCACTTTTTATCAGTGCGGTCAGAACTTCAGCCTGAGTCAGGC
CATCTTCATGACACATTTGCATGAGCATGGCCTTATACTTTGGTTCAAGA
AATACTTTTACTTCCTGAACGAAGCTCTTTTACGGGCCACTGATAATCT
TTGTTTCTCTGCATCAGAAAGCGGATTCCCCTTTCTGTATGCTCGTTTTG
CGCCAGATGAGGAAGTCACTGCATTTTCTGTCTGCGACATCTCGCCTCCT
CAATACTTAAACAGGGATCGTTTCGCAGAGGATACTACAGTTTTTTGAAA
TCAGCGACTTGAGAATTGTGACGAAGATCCGGGATTACCCTGTTATCCCT
AGAGCTTGGCGTAATCATGGTCATAGCTGTTTCCTGTGTGAAATTGTTAT
CCGCTCACAATTCCACACAACATACGAGCCGGAAGCATAAAGTGTAAAGC
CTGGGGTGCCTAATGAGTGAGCTAACTCACATTAATTGCGTTGCGCTCAC
TGCCCGCTTTCCAGTCGGGAAACCTGTCGTGCCAGCTGCATTAATGAATC
GGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTAT
CAGCTCACTCAAAGGCGGTAATACGGTTATCCACAGAATCAGGGGATAAC
GCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTA
TAAAGATACCAGGCGTTTCCCCCTGGAAGCTCCCTCGTGCGCTCTCCTGT
TCCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGA

-continued
```
CCGCTGCGCCTTATCCGGTAACTATCGTCTTGAGTCCAACCCGGTAAGAC

ACGACTTATCGCCACTGGCAGCAGCCACTGGTAACAGGATTAGCAGAGCG

AGGTATGTAGGCGGTGCTACAGAGTTCTTGAAGTGGTGGCCTAACTACGG

CTACACTAGAAGGACAGTATTTGGTATCTGCGCTCTGCTGAAGCCAGTTA

CCTTCGGAAAAAGAGTTGGTAGCTCTTGATCCGGCAAACAAACCACCGCT

GGTAGCGGTGGTTTTTTTGTTTGCAAGCAGCAGATTACGCGCAGAAAAAA

AGGATCTCAAGAAGATCCTTTGATCTTTTCTACGGGGTCTGACGCTCAGT

GGAACGAAAACTCACGTTAAGGGATTTTGGTCATGAGATTATCAAAAAGG

ATCTTCACCTAGATCCTTTTAAATTAAAAATGAAGTTTTAAATCAATCTA

AAGTATATATGAGTAAACTTGGTCTGACAGTTACCAATGCTTAATCAGTG

AGGCACCTATCTCAGCGATCTGTCTATTTCGTTCATCCATAGTTGCCTGA

CTCCCCGTCGTGTAGATAACTACGATACGGGAGGGCTTACCATCTGGCCC

CAGTGCTGCAATGATACCGCGAGACCCACGCTCACCGGCTCCAGATTTAT

CAGCAATAAACCAGCCAGCCGGAAGGGCCGAGCGCAGAAGTGGTCCTGCA

ACTTTATCCGCCTCCATCCAGTCTATTAATTGTTGCCGGGAAGCTAGAGT

AAGTAGTTCGCCAGTTAATAGTTTGCGCAACGTTGTTGCCATTGCTACAG

GCATCGTGGTGTCACGCTCGTCGTTTGGTATGGCTTCATTCAGCTCCGGT

TCCCAACGATCAAGGCGAGTTACATGATCCCCCATGTTGTGCAAAAAAGC

GGTTAGCTCCTTCGGTCCTCCGATCGTTGTCAGAAGTAAGTTGGCCGCAG

TGTTATCACTCATGGTTATGGCAGCACTGCATAATTCTCTTACTGTCATG

CCATCCGTAAGATGCTTTTCTGTGACTGGTGAGTACTCAACCAAGTCATT

CTGAGAATAGTGTATGCGGCGACCGAGTTGCTCTTGCCCGGCGTCAATAC

GGGATAATACCGCGCCACATAGCAGAACTTTAAAAGTGCTCATCATTGGA

AAACGTTCTTCGGGGCGAAAACTCTCAAGGATCTTACCGCTGTTGAGATC

CAGTTCGATGTAACCCACTCGTGCACCCAACTGATCTTCAGCATCTTTTA

CTTTCACCAGCGTTTCTGGGTGAGCAAAAACAGGAAGGCAAAATGCCGCA

AAAAAGGGAATAAGGGCGACACGGAAATGTTGAATACTCATACTCTTCCT

TTTTCAATGGGGTGGGCGAAGAACTCCAGCATGAGATCCCCGCGCTGGAG

GATCATCCAGCCGGCGTCCCGGAAAACGATTCCGAAGCCCAACCTTTCAT

AGAAGGCGGCGGTGGAATCGAAATCTCGTGATGGCAGGTTGGGCGTCGCT

TGGTCGGTCATTTCGAACCCCAGAGTCCCGCTCAGAAGAACTCGTCAAGA

AGGCGATAGAAGGCGATGCGCTGCGAATCGGGAGCGGCGATACCGTAAAG

CACGAGGAAGCGGTCAGCCCATTCGCCGCCAAGCTCTTCAGCAATATCAC

GGGTAGCCAACGCTATGTCCTGATAGCGGTCCGCCACACCCAGCCGGCCA

CAGTCGATGAATCCAGAAAAGCGGCCATTTTCCACCATGATATTCGGCAA

GCAGGCATCGCCATGGGTCACGACGAGATCCTCGCCGTCGGGCATGCGCG

CCTTGAGCCTGGCGAACAGTTCGGCTGGCGCGAGCCCCTGATGCTCTTCG

TCCAGATCATCCTGATCGACAAGACCGGCTTCCATCCGAGTACGTGCTCG

CTCGATGCGATGTTTCGCTTGGTGGTCGAATGGGCAGGTAGCCGGATCAA

GCGTATGCAGCCGCCGCATTGCATCAGCCATGATGGATACTTTCTCGGCA

GGAGCAAGGTGAGATGACAGGAGATCCTGCCCCGGCACTTCGCCCAATAG
```

-continued
```
CAGCCAGTCCCTTCCCGCTTCAGTGACAACGTCGAGCACAGCTGCGCAAG

GAACGCCCGTCGTGGCCAGCCACGATAGCCGCGCTGCCTCGTCCTGCAGT

TCATTCAGGGCACCGGACAGGTCGGTCTTGACAAAAAGAACCGGGCGCCC

CTGCGCTGACAGCCGGAACACGGCGGCATCAGAGCAGCCGATTGTCTGTT

GTGCCCAGTCATAGCCGAATAGCCTCTCCACCCAAGCGGCCGGAGAACCT

GCGTGCAATCCATCTTGTTCAATCATGCGAAACGATCCTCATCCTGTCTC

TTGATCAGATCTTGATCCCCTGCGCCATCAGATCCTTGGCGGCAAGAAAG

CCATCCAGTTTACTTTGCAGGGCTTCCCAACCTTACCAGAGGGCGCCCCA

GCTGGCAATTCCGGTTCGCTTGCTGTCCATAAAACCGCCCAGTCTAGCTA

TCGCCATGTAAGCCCACTGCAAGCTACCTGCTTTCTCTTTGCGCTTGCGT

TTTCCCTTGTCCAGATAGCCCAGTAGCTGACATTCATCCGGGGTCAGCAC

CGTTTCTGCGGACTGGCTTTCTACGTGTTCCGCTTCCTTTAGCAGCCCTT

GCGCCCTGAGTGCTTGCGGCAGCGTGAAGCTATTATTGAAGCATTTATCA

GGGTTATTGTCTCATGAGCGGATACATATTTGAATGTATTTAGAAAAATA

AACAAATAGGGGTTCCGCGCACATTTCCCCGAAAAGTGCCACCTGACGTC

TAAGAAACCATTATTATCATGACATTAACCTATAAAAATAGGCGTATCAC

GAGGCGCCCTTTCGTC
```

Accordingly, in a third aspect, there is provided a recombinant vector pCURE2, substantially as illustrated in FIG. 4. Nucleic acid sequences for the pCURE2 vector are provided in SEQ ID No:3 and 29. Preferably the recombinant vector pCURE2 comprises the nucleic acid sequence provided in SEQ ID No. 29. Advantageously, pCURE2 may be used against any plasmid suspected of being an F-like plasmid from a host cell. The inventors have successfully tested pCURE2 against a number of selected F-like plasmids with surprising efficacy. Using this plasmid, they were able to cure a much wider range of F incompatibility group plasmids.

The inventors then decided to create a third recombinant plasmid similar to pCURE1, but which also comprises segments of IncP-1. This was to create an IncP-1 displacement plasmid in order to demonstrate the general applicability of the method to curing IncP-α and IncP-β, plasmids.

Hence, in another preferred embodiment, the nucleic acid molecule comprises at least a region of IncP-1, the sequence of which is shown in L27758. Preferably, the molecule comprises segments from the IncP-1 regions: oriV, parD and korA/incC. Hence, the nucleic acid molecule used in the method is pCURE11, substantially as illustrated in FIG. 5.

The nucleotide sequence of pCURE11 (9419 bp) is identified as SEQ ID No. 4.

[SEQ ID No. 4]
```
TCGCGCGTTTCGGTGATGACGGTGAAAACCTCTGACACATGCAGCTCCCG

GAGACGGTCACAGCTTGTCTGTAAGCGGATGCCGGGAGCAGACAAGCCCG

TCAGGGCGCGTCAGCGGGTGTTGGCGGGTGTCGGGGCTGGCTTAACTATG

CGGCATCAGAGCAGATTGTACTGAGAGTGCACCATAATCGGCATTTTCTT

TTGCGTTTTTATTTGTTAACTGTTAATTGTCCTTGTTCAAGGATGCTGTC

TTTGACAACAGATGTTTTCTTGCCTTTGATGTTCAGCAGGAAGCTAGGCG

CAAACGTTGATTGTTTGTCTGCGTAGAATCCTCTGTTTGTCATATAGCTT
```

```
GTAATCACGACATTGTTTCCTTTCGCTTGAGGTACAGCGAAGTGTGAGTA
AGTAAAGGTTACATCGTTAGGATCAAGATCCATTTTTAACACAAGGCCAG
TTTTGTTCAGCGGCTTGTATGGGCCAGTTAAAGAATTAGAAACATAACCA
AGCATGTAAATATCGTTAGACGTAATGCCGTCAATCGTCATTTTTGATCC
GCGGGAGTCAGTGAACAGATACCATTTGCCGTTCATTTTAAAGACGTTCG
CGCGTTCAATTTCATCTGTTACTGTGTTAGATGCAATCAGCGGTTTCATC
ACTTTTTTCAGTGTGTAATCATCGTTTAGCTCAATCATACCGAGAGCGCC
GTTTGCTAACTCAGCCGTGCGTTTTTTATCGCTTTGCAGAAGTTTTTGAC
TTTCTTGACGGAAGAATGATGTGCTTTTGCCATAGTATGCTTTGTTAAAT
AAAGATTCTTCGCCTTGGTAGCCATCTTCAGTTCCAGTGTTTGCTTCAAA
TACTAAGTATTTGTGGCCTTTATCTTCTACGTAGTGAGGATCTCTCAGCG
TATGGTTGTCGCCTGAGCTGTAGTTGCCTTCATCGATGAACTGCTGTACA
TTTTGATACGTTTTTCCGTCACCGTCAAAGATTGATTTATAATCCTCTAC
ACCGTTGATGTTCAAAGAGCTGTCTGATGCTGATACGTTAACTTGTGCAG
TTGTCAGTGTTTGTTTGCCGTAATGTTTACCGGAGAAATCAGTGTAGAAT
AAACGGATTTTTCCGTCAGATGTAAATGTGGCTGAACCTGACCATTCTTG
TGTTTGGTCTTTTAGGATAGAATCATTTGCATCGAATTTGTCGCTGTCTT
TAAAGACGCGGCCAGCGTTTTTCCAGCTGTCAATAGAAGTTTCGCCGACT
TTTTGATAGAACATGTAAATCGATGTGTCATCCGCATTTTTAGGATCTCC
GGCTAATGCAAAGACGATGTGGTAGCCGTGATAGTTTGCGACAGTGCCGT
CAGCGTTTTGTAATGGCCAGCTGTCCCAAACGTCCAGGCCTTTTGCAGAA
GAGATATTTTAATTGTGGACGAATCGAACTCAGGAACTTGATATTTTTC
ATTTTTTTGCTGTTCAGGGATTTGCAGCATATCATGGCGTGTAATATGGG
AAATGCCGTATGTTTCCTTATATGGCTTTTGGTTCGTTTCTTTCGCAAAC
GCTTGAGTTGCGCCTCCTGCCAGCAGTGCGGTAGTAAAGGTTAATACTGT
TGCTTGTTTTGCAAACTTTTTGATGTTCATCGTTCATGTCTCCTTTTTA
TGTACTGTGTTAGCGTTCTGCTTCTTCCAGCCCTCCTGTTTGAAGATGGC
AAGTTAGTTACGCACAATAAAAAAAGACCTAAAATATGTAAGGGGTGACG
CCAAAGTATACACTTTGCCCTTTACACATTTTAGGTCTTGCCTGCTTTAT
CAGTAACAAACCCGCGCGATTTACTTTTCGACCTCATTCTATTAGACTCT
CGTTTGGATTGCAACTGGTCTATTTTCCTCTTTTGTTTGATAGAAAATCA
TAAAAGGATTTGCAGACTACGGGCCTAAAGAACTAAAAAATCTATCTGTT
TCTTTTCATTCTCTGTATTTTTTATAGTTTCTGTTGCATGGGCATAAAGT
TGCCTTTTTAATCACAATTCAGAAAATATCATAATATCTCATTTCACTAA
ATAATAGTGAACGGCAGGTATATGTGATGGGTTAAAAAGGATCGATCCTC
TAGCTAGAGTCGATCTTCGCCAGCAGGGCGAGGATCGTGGCATCACCGAA
CCGCGCCGTGCGCGGGTCGTCGGTGAGCCAGAGTTTCAGCAGGCCGCCCA
GGCGGCCCAGGTCGCCATTGATGCGGGCCAGCTCGCGGACGTGCTCATAG
TCCACGACGCCCGTGATTTTGTAGCCCTGGCCGACGGCCAGCAGGTAGGC
CGACAGGCTCATGCCGGCCGCCGCCGCCTTTTCCTCAATCGCTCTTCGTT
CGTCTGGAAGGCAGTACACCTTGATAGGTGGGCTGCCCTTCCTGGTTGGC

TTGGTTTCATCAGCCATCCGCTTGCCCTCATCTGTTACGCCGGCGGTAGC
CGGCCAGCCTCGCAGAGCAGGATTCCCGTTGAGCACCGCCAGGTGCGAAT
AAGGGACAGTGAAGAAGGAACACCCGCTCGCGGGTGGGCCTACTTCACCT
ATCCTGCCCGGCTGACGCCGTTGGATACACCAAGGAAAGTCTACACGAAC
CCTTTGGCAAAATCCTGTATATCGTGCGAAAAAGGATGGATATACCGAAA
AAATCGCTATAATGACCCCGAAGCAGGGTTATGCAGCGGAAAAGCGCTGC
TTCCCTGCTGTTTTGTGGAATATCTACCGACTGGAAACAGGCAAATGCAG
GAAATTACTGAACTGAGGGGACAGGCGAGAGACGATGCCAAAGAGCTACA
CCGACGAGCTGGCCGAGTGGGTTGAATCCCGCGCGGCCAAGAAGCGCCGG
CGTGATGAGGCTGCGGTTGCGTTCCTGGCGGTGAGGGCGGATGTCGATAT
GCGTAAGGAGAAAATACCGCATCAGGCGCATGCATATTTGAATGTATTTA
GAAAAATAAACAAAAAGAGTTTGTAGAAACGCAAAAAGGCCATCCGTCAG
GATGGCCTTCTGCTTAATTTGATGCCTGGCAGTTTATGGCGGGCGTCCTG
CCCGCCACCCTCCGGGCCGTTGCTTCGCAACGTTCAAATCCGCTCCCGGC
GGATTTGTCCTACTCAGGAGAGCGTTCACCGACAAACAACAGATAAAACG
AAAGGCCCAGTCTTTCGACTGAGCCTTTCGTTTTATTTGATGCCTGGCAG
TTCCCTACTCTCGCATGGGGAGACCCCACACTACCATCGGCGCTACGGCG
TTTCACTTCTGAGTTCGGCATGGGGTCAGGTGGGACCACCGCGCTACTGC
CGCCAGGCAAATTCTGTTTTATCAGACCGCTTCTGCGTTCTGATTTAATC
TGTATCAGGCTGAAAATCTTCTCTCATCCGCCAAAACAGCCAAGCTCGCC
ATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGG
CCAGTGCCAAGCTCATTACCCTGTTATCCCTACCCGGTGAATTCAGCGCA
TTTTCCCGACCTTAATGCGCCTCGCGCTGTAGCCTCACGCCCACATATGT
GCTAATGTGGTTACGTGTATTTTATGGAGGTTATCCAATGAGCCGCCTGA
CAATCGACATGACGGACCAGCAGCACCAGAGCCTGAAAGCCCTGGCCGCC
TTGCAGGGCAAGACCATTAAGCAATACGCCCTCGAACGTCTGTTCCCCGG
TGACGCTGATGCCGATCAGGCATGGCAGGAACTGAAAACCATGCTGGGA
ACCGCATCAACGATGGGCTTGCCGGCAAGGTGTCCACCAAGAGCGTCGGC
GAAATTCTTGATGAAGAACTCAGCGGGGATCGCGCTTGACGGCCTACATC
CTCACGGCTGGGATCTAAGGACGAGTTTTAGCGGCTAAAGGTGTTGACGT
GCGAGAAATGTTTAGCTAAACTTCTCTCATGTGCTGGCGGCTGTCACCGC
TATGTTCAACCAAGGCGCGGAGCAAATTATGGGTGTTATCCATGAAGAAA
CGGCTTACCGAAAGCCAGTTCCAGGAGGCGATCCAGGGGCTGGAAGTGGG
GCAGCAGACCATCGAGATAGCGCGGGCGTCTTAGTCGATGGGAAGCCAC
AGGCGACGTTCGCAACGTCGCTGGGACTGACCAGGGGCGCAGTGTCGCAA
GCGGTGCATCGCGTGTGGGCCGCGTTCGAGGACAAGAACTTGCCCGAGGG
GTACGCGCGGGTAACGGCGGTTCTGCCGGAACATCAGGCGTACATCGTCC
GGAAGTGGGAAGCGGACGCCAAGAAAAAACAGGAAACCAAACGATGAAAA
CTTTGGTCACGGCCAACCAGAAAGGCGGCGTCGGCAAGACTTCGACCCTT
```

-continued

```
GTGCATCTTGCCTTCGACTTTTTCGAGCGCGGCTTGCGGGTTGCCGTGAT
CGACCTGGACCCCCAGGGCAATGCGTCCTACACGCTCAAGGACTTTGCTA
CCGGCCTGCATGCAAGCAAGCTGTTCGGCGCTGTCCCTGCCGGCGGCTGG
ACCGAAACCGCACCCGCAGCCGGCGACGGCCAGGCCGCGCGCCTCGCCCT
CATCGAGTCCAACCCGGTACTGGCGAACGCCGAACGCCTGTCGCTGGACG
ACGCCCGCGAGCTGTTCGGGGCGAACATCAAGGCCCTGGCGAACCAAGGC
TTCGACGTGTGCCTGATCGACACGGCCCCGACCCTTGGCGTCGGCCTGGC
GGCCGCCCTCTTCGCGGCCGACTATGTGCTGTCCCCCATCGAGCTTGAGG
CGTACAGCATCCAGGGCATCAAGAAGATGGTCACGACCATTGCGAACGTG
CGCCAGAAGAACGCCAAGCTGCAATTCCTTGGCATGGTGCCCAGCAAGGT
CGATGCGCGGAATCCGCGCCACGCGCGCCACCAAGCCGAGCTGCTGGCCG
CGTACCCCAAGATGATGATTCCGGCCACCGTTGGCCTGCGCAGCAGCATC
GCCGATGCCCTCGCATCCGGTGTGCCGGTCTGGAAGATCAAGAAAACGGC
CGCGCGCAAGGCATCGAAAGAGGTTCGCGCCCTGGCTGATTACGTGTTCA
CGAAGATGGAGATTTCCCAATGACTGCGGCTCAAGCCAAGACCACCAGTC
GAGGCGTGGACTCAAGGCTCTCGCGAATGGCTCGCGTTGGAAACTTTCAT
TGACACTTGAGGGGCACCGCAGGGAAATTCTCGTCCTTGCGAGAACCGGC
TATGTCGTGCTGCGCATCGAGCCTGCGCCCTTGGCTTGTCTCGCCCCTCT
CCGCGTCGCTACGGGGCTTCCAGCGCCTTTCCGACGCTCACCGGGCTGGT
TGCCCTCGCCGCTGGGCTGGCGGCCGTCTATGGCCCTGCAAACGCGCCAG
AAACGCCGTCGAAGCCGTGTGCGAGACACCGCGGCCGCCGGCGTTGTGGA
TACCACGCGGAAAACTTGGCCCTCACTGACAGATGAGGGCGGACGTTGA
CACTTGAGGGGCCGACTCACCCGGCGCGGCGTTGACAGATGAGGGCAGG
CTCGATTTCGGCCGGCGACGTGGAGCTGGCCAGCCTCGCAAATCGGCGAA
AACGCCTGATTTTACGCGAGTTTCCCACAGATGATGTGGACAAGCCTGGG
GATAAGTGCCCTGCGGTATTGACACTTGAGGGGCGCGACTACTGACAGAT
GAGGGGCGCGATCCTTGACACTTGAGGGGCAGAGTGATGACAGATGAGGG
GCGCACCTATTGACATTTGAGGGGCTGGGATCCGGGATTACCCTGTTATC
CCTAGAGCTTGGCGTAATCATGGTCATAGCTGTTTCCTGTGTGAAATTGT
TATCCGCTCACAATTCCACACAACATACGAGCCGGAAGCATAAAGTGTAA
AGCCTGGGGTGCCTAATGAGTGAGCTAACTCACATTAATTGCGTTGCGCT
CACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGG
TATCAGCTCACTCAAAGGCGGTAATACGGTTATCCACAGAATCAGGGGAT
AACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGG
GAAGCGTGGCGCTTTCTCATAGCTCACGCTGTAGGTATCTCAGTTCGGTG
```

-continued

```
TAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAA
GACACGACTTATCGCCACTGGCAGCAGCCACTGGTAACAGGATTAGCAGA
GCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAG
TTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTC
AGTGGAACGAAAACTCACGTTAAGGGATTTTGGTCATGAGATTATCAAAA
AGGATCTTCACCTAGATCCTTTTAAATTAAAAATGAAGTTTTAAATCAAT
CTAAAGTATATATGAGTAAACTTGGTCTGACAGTTACCAATGCTTAATCA
GTGAGGCACCTATCTCAGCGATCTGTCTATTTCGTTCATCCATAGTTGCC
TGACTCCCCGTCGTGTAGATAACTACGATACGGGAGGGCTTACCATCTGG
CCCCAGTGCTGCAATGATACCGCGAGACCCACGCTCACCGGCTCCAGATT
TATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCC
GGTTCCCAACGATCAAGGCGAGTTACATGATCCCCCATGTTGTGCAAAAA
AGCGGTTAGCTCCTTCGGTCCTCCGATCGTTGTCAGAAGTAAGTTGGCCG
CAGTGTTATCACTCATGGTTATGGCAGCACTGCATAATTCTCTTACTGTC
ATGCCATCCGTAAGATGCTTTTCTGTGACTGGTGAGTACTCAACCAAGTC
ATTCTGAGAATAGTGTATGCGGCGACCGAGTTGCTCTTGCCCGGCGTCAA
TACGGGATAATACCGCGCCACATAGCAGAACTTTAAAAGTGCTCATCATT
GGAAAACGTTCTTCGGGGCGAAAACTCTCAAGGATCTTACCGCTGTTGAG
ATCCAGTTCGATGTAACCCACTCGTGCACCCAACTGATCTTCAGCATCTT
TTACTTTCACCAGCGTTTCTGGGTGAGCAAAAACAGGAAGGCAAAATGCC
GCAAAAAAGGGAATAAGGGCGACACGGAAATGTTGAATACTCATACTCTT
CCTTTTTCAATGGGGTGGGCGAAGAACTCCAGCATGAGATCCCCGCGCTG
GAGGATCATCCAGCCGGCGTCCCGGAAAACGATTCCGAAGCCCAACCTTT
CATAGAAGGCGGCGGTGGAATCGAAATCTCGTGATGGCAGGTTGGGCGTC
GCTTGGTCGGTCATTTCGAACCCCAGAGTCCCGCTCAGAAGAACTCGTCA
AGAAGGCGATAGAAGGCGATGCGCTGCGAATCGGGAGCGGCGATACCGTA
AAGCACGAGGAAGCGGTCAGCCCATTCGCCGCCAAGCTCTTCAGCAATAT
CACGGGTAGCCAACGCTATGTCCTGATAGCGGTCCGCCACACCCAGCCGG
CCACAGTCGATGAATCCAGAAAAGCGGCCATTTTCCACCATGATATTCGG
CAAGCAGGCATCGCCATGGGTCACGACGAGATCCTCGCCGTCGGGCATGC
GCGCCTTGAGCCTGGCGAACAGTTCGGCTGGCGCGAGCCCCTGATGCTCT
TCGTCCAGATCATCCTGATCGACAAGACCGGCTTCCATCCGAGTACGTGC
TCGCTCGATGCGATGTTTCGCTTGGTGGTCGAATGGGCAGGTAGCCGGAT
CAAGCGTATGCAGCCGCCGCATTGCATCAGCCATGATGGATACTTTCTCG
```

-continued
GCAGGAGCAAGGTGAGATGACAGGAGATCCTGCCCCGGCACTTCGCCCAA
TAGCAGCCAGTCCCTTCCCGCTTCAGTGACAACGTCGAGCACAGCTGCGC
AAGGAACGCCCGTCGTGGCCAGCCACGATAGCCGCGCTGCCTCGTCCTGC
AGTTCATTCAGGGCACCGGACAGGTCGGTCTTGACAAAAAGAACCGGGCG
CCCCTGCGCTGACAGCCGGAACACGGCGGCATCAGAGCAGCCGATTGTCT
GTTGTGCCCAGTCATAGCCGAATAGCCTCTCCACCCAAGCGGCCGGAGAA
CCTGCGTGCAATCCATCTTGTTCAATCATGCGAAACGATCCTCATCCTGT
CTCTTGATCAGATCTTGATCCCCTGCGCCATCAGATCCTTGGCGGCAAGA
AAGCCATCCAGTTTACTTTGCAGGGCTTCCCAACCTTACCAGAGGGCGCC
CCAGCTGGCAATTCCGGTTCGCTTGCTGTCCATAAAACCGCCCAGTCTAG
CTATCGCCATGTAAGCCCACTGCAAGCTACCTGCTTTCTCTTTGCGCTTG
CGTTTTCCCTTGTCCAGATAGCCCAGTAGCTGACATTCATCCGGGGTCAG
CACCGTTTCTGCGGACTGGCTTTCTACGTGTTCCGCTTCCTTTAGCAGCC
CTTGCGCCCTGAGTGCTTGCGGCAGCGTGAAGCTATTATTGAAGCATTTA
TCAGGGTTATTGTCTCATGAGCGGATACATATTTGAATGTATTTAGAAAA
ATAAACAAATAGGGGTTCCGCGCACATTTCCCCGAAAAGTGCCACCTGAC
GTCTAAGAAACCATTATTATCATGACATTAACCTATAAAAATAGGCGTAT
CACGAGGCGCCCTTTCGTC Accordingly, in a fourth aspect, there is provided a recombinant vector pCURE11, substantially as illustrated in FIG. 5. Advantageously, and preferably, pCURE11 may be used in the method according to the invention for curing IncP-α and IncP-β, plasmids from a host cell, such as *E. coli*.

The inventors then created a fourth recombinant displacement plasmid, which was based on pCURE11, and included an IncP-9 replicon. Hence, in another preferred embodiment, the nucleic acid molecule comprises an IncP-9 replicon, the sequence of which is shown in AF078924. Hence, the nucleic acid molecule used in the method is pCURE12, substantially as illustrated in FIG. 6.

The nucleotide sequence of pCURE12 (10733 bp) is identified as SEQ ID No. 5.

[SEQ ID No. 5]
TCGCGCGTTTCGGTGATGACGGTGAAAACCTCTGACACATGCAGCTCCCG
GAGACGGTCACAGCTTGTCTGTAAGCGGATGCCGGGAGCAGACAAGCCCG
TCAGGGCGCGTCAGCGGGTGTTGGCGGGTGTCGGGGCTGGCTTAACTATG
CGGCATCAGAGCAGATTGTACTGAGAGTGCACCATAATCGGCATTTTCTT
TTGCGTTTTTATTTGTTAACTGTTAATTGTCCTTGTTCAAGGATGCTGTC
TTTGACAACAGATGTTTTCTTGCCTTTGATGTTCAGCAGGAAGCTAGGCG
CAAACGTTGATTGTTTGTCTGCGTAGAATCCTCTGTTTGTCATATAGCTT
GTAATCACGACATTGTTTCCTTTCGCTTGAGGTACAGCGAAGTGTGAGTA
AGTAAAGGTTACATCGTTAGGATCAAGATCCATTTTTAACACAAGGCCAG
TTTTGTTCAGCGGCTTGTATGGGCCAGTTAAAGAATTAGAAACATAACCA
AGCATGTAAATATCGTTAGACGTAATGCCGTCAATCGTCATTTTTGATCC
GCGGGAGTCAGTGAACAGATACCATTTGCCGTTCATTTTAAAGACGTTCG

-continued
CGCGTTCAATTTCATCTGTTACTGTGTTAGATGCAATCAGCGGTTTCATC
ACTTTTTTCAGTGTGTAATCATCGTTTAGCTCAATCATACCGAGAGCGCC
GTTTGCTAACTCAGCCGTGCGTTTTTATCGCTTTGCAGAAGTTTTTGAC
TTTCTTGACGGAAGAATGATGTGCTTTTGCCATAGTATGCTTTGTTAAAT
AAAGATTCTTCGCCTTGGTAGCCATCTTCAGTTCCAGTGTTTGCTTCAAA
TACTAAGTATTTGTGGCCTTTATCTTCTACGTAGTGAGGATCTCTCAGCG
TATGGTTGTCGCCTGAGCTGTAGTTGCCTTCATCGATGAACTGCTGTACA
TTTTGATACGTTTTTCCGTCACCGTCAAAGATTGATTTATAATCCTCTAC
ACCGTTGATGTTCAAAGAGCTGTCTGATGCTGATACGTTAACTTGTGCAG
TTGTCAGTGTTTGTTTGCCGTAATGTTTACCGGAGAAATCAGTGTAGAAT
AAACGGATTTTTCCGTCAGATGTAAATGTGGCTGAACCTGACCATTCTTG
TGTTTGGTCTTTTAGGATAGAATCATTTGCATCGAATTTGTCGCTGTCTT
TAAAGACGCGGCCAGCGTTTTTCCAGCTGTCAATAGAAGTTTCGCCGACT
TTTTGATAGAACATGTAAATCGATGTGTCATCCGCATTTTTAGGATCTCC
GGCTAATGCAAAGACGATGTGGTAGCCGTGATAGTTTGCGACAGTGCCGT
CAGCGTTTTGTAATGGCCAGCTGTCCCAAACGTCCAGGCCTTTTGCAGAA
GAGATATTTTAATTGTGGACGAATCGAACTCAGGAACTTGATATTTTTC
ATTTTTTTGCTGTTCAGGGATTTGCAGCATATCATGGCGTGTAATATGGG
AAATGCCGTATGTTTCCTTATATGGCTTTTGGTTCGTTTCTTTCGCAAAC
GCTTGAGTTGCGCCTCCTGCCAGCAGTGCGGTAGTAAAGGTTAATACTGT
TGCTTGTTTTGCAAACTTTTTGATGTTCATCGTTCATGTCTCCTTTTTA
TGTACTGTGTTAGCGGTCTGCTTCTTCCAGCCCTCCTGTTTGAAGATGGC
AAGTTAGTTACGCACAATAAAAAAAGACCTAAAATATGTAAGGGGTGACG
CCAAAGTATACACTTTGCCCTTTACACATTTTAGGTCTTGCCTGCTTTAT
CAGTAACAAACCCGCGCGATTTACTTTTCGACCTCATTCTATTAGACTCT
CGTTTGGATTGCAACTGGTCTATTTTCCTCTTTTGTTTGATAGAAAATCA
TAAAAGGATTTGCAGACTACGGGCCTAAAGAACTAAAAAATCTATCTGTT
TCTTTTCATTCTCTGTATTTTTTATAGTTTCTGTTGCATGGGCATAAAGT
TGCCTTTTTAATCACAATTCAGAAAATATCATAATATCTCATTTCACTAA
ATAATAGTGAACGGCAGGTATATGTGATGGGTTAAAAAGGATCGATCCTC
TAGCTAGAGTCGATCTTCGCCAGCAGGGCGAGGATCGTGGCATCACCGAA
CCGCGCCGTGCGCGGGTCGTCGGTGAGCCAGAGTTTCAGCAGGCCGCCCA
GGCGGCCCAGGTCGCCATTGATGCGGGCCAGCTCGCGGACGTGCTCATAG
TCCACGACGCCCGTGATTTTGTAGCCCTGGCCGACGGCCAGCAGGTAGGC
CGACAGGCTCATGCCGGCCGCCGCCGCCTTTTCCTCAATCGCTCTTCGTT
CGTCTGGAAGGCAGTACACCTTGATAGGTGGGCTGCCCTTCCTGGTTGGC
TTGGTTTCATCAGCCATCCGCTTGCCCTCATCTGTTACGCCGGCGGTAGC
CGGCCAGCCTCGCAGAGCAGGATTCCCGTTGAGCACCGCCAGGTGCGAAT
AAGGGACAGTGAAGAGGAACACCCGCTCGCGGGTGGGCCTACTTCACCT
ATCCTGCCCGGCTGACGCCGTTGGATACACCAAGGAAAGTCTACACGAAC
CCTTTGGCAAAATCCTGTATATCGTGCGAAAAAGGATGGATATACCGAAA -continued AAATCGCTATAATGACCCCGAAGCAGGGTTATGCAGCGGAAAAGCGCTGC
TTCCCTGCTGTTTTGTGGAATATCTACCGACTGGAAACAGGCAAATGCAG
GAAATTACTGAACTGAGGGGACAGGCGAGAGACGATGCCAAAGAGCTACA
CCGACGAGCTGGCCGAGTGGGTTGAATCCCGCGCGGCCAAGAAGCGCCGG
CGTGATGAGGCTGCGGTTGCGTTCCTGGCGGTGAGGGCGGATGTCGATAT
GCGTAAGGAGAAAATACCGCATCAGGCGCATGCATATTTGAATGTATTTA
GAAAAATAAACAAAAAGAGTTTGTAGAAACGCAAAAAGGCCATCCGTCAG
GATGGCCTTCTGCTTAATTTGATGCCTGGCAGTTTATGCGGGCGTCCTG
CCCGCCACCCTCCGGGCCGTTGCTTCGCAACGTTCAAATCCGCTCCCGGC
GGATTTGTCCTACTCAGGAGAGCGTTCACCGACAAACAACAGATAAAACG
AAAGGCCCAGTCTTTCGACTGAGCCTTTCGTTTTATTTGATGCCTGGCAG
TTCCCTACTCTCGCATGGGGAGACCCCACACTACCATCGGCGCTACGGCG
TTTCACTTCTGAGTTCGGCATGGGGTCAGGTGGGACCACCGCGCTACTGC
CGCCAGGCAAATTCTGTTTTATCAGACCGCTTCTGCGTTCTGATTTAATC
TGTATCAGGCTGAAAATCTTCTCTCATCCGCCAAAACAGCCAAGCTCGCC
ATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGG
CCAGTGCCAAGCTCATTACCCTGTTATCCCTACCCGGTGAATTCAGCGCA
TTTTCCCGACCTTAATGCGCCTCGCGCTGTAGCCTCACGCCCACATATGT
GCTAATGTGGTTACGTGTATTTTATGGAGGTTATCCAATGAGCCGCCTGA
CAATCGACATGACGGACCAGCAGCACCAGAGCCTGAAAGCCCTGGCCGCC
TTGCAGGGCAAGACCATTAAGCAATACGCCCTCGAACGTCTGTTCCCCGG
TGACGCTGATGCCGATCAGGCATGGCAGGAACTGAAAACCATGCTGGGGA
ACCGCATCAACGATGGGCTTGCCGGCAAGGTGTCCACCAAGAGCGTCGGC
GAAATTCTTGATGAAGAACTCAGCGGGGATCGCGCTTGACGGCCTACATC
CTCACGGCTGGGATCTAAGGACGAGTTTTAGCGGCTAAAGGTGTTGACGT
GCGAGAAATGTTTAGCTAAACTTCTCTCATGTGCTGGCGGCTGTCACCGC
TATGTTCAACCAAGGCGCGGAGCAAATTATGGGTGTTATCCATGAAGAAA
CGGCTTACCGAAAGCCAGTTCCAGGAGGCGATCCAGGGGCTGGAAGTGGG
GCAGCAGACCATCGAGATAGCGCGGGGCGTCTTAGTCGATGGGAAGCCAC
AGGCGACGTTCGCAACGTCGCTGGGACTGACCAGGGGCGCAGTGTCGCAA
GCGGTGCATCGCGTGTGGGCCGCGTTCGAGGACAAGAACTTGCCCGAGGG
GTACGCGCGGGTAACGGCGGTTCTGCCGGAACATCAGGCGTACATCGTCC
GGAAGTGGGAAGCGGACGCCAAGAAAAAACAGGAAACCAAACGATGAAAA
CTTTGGTCACGGCCAACCAGAAAGGCGGCGTCGGCAAGACTTCGACCCTT
GTGCATCTTGCCTTCGACTTTTTCGAGCGCGGCTTGCGGGTTGCCGTGAT
CGACCTGGACCCCCAGGGCAATGCGTCCTACACGCTCAAGGACTTTGCTA
CCGGCCTGCATGCAAGCAAGCTGTTCGGCGCTGTCCCTGCCGGCGGCTGG
ACCGAAACCGCACCCGCAGCCGGCGACGGCCAGGCCGCGCGCCTCGCCCT
CATCGAGTCCAACCCGGTACTGGCGAACGCCGAACGGCTGTCGCTGGACG -continued ACGCCCGCGAGCTGTTCGGGGCGAACATCAAGGCCCTGGCGAACCAAGGC
TTCGACGTGTGCCTGATCGACACGGCCCCGACCCTTGGCGTCGGCCTGGC
GGCCGCCCTCTTCGCGGCCGACTATGTGCTGTCCCCCATCGAGCTTGAGG
CGTACAGCATCCAGGGCATCAAGAAGATGGTCACGACCATTGCGAACGTG
CGCCAGAAGAACGCCAAGCTGCAATTCCTTGGCATGGTGCCCAGCAAGGT
CGATGCGCGGAATCCGCGCCACGCGCGCCACCAAGCCGAGCTGCTGGCCG
CGTACCCCAAGATGATGATTCCGGCCACCGTTGGCCTGCGCAGCAGCATC
GCCGATGCCCTCGCATCCGGTGTGCCGGTCTGGAAGATCAAGAAAACGGC
CGCGCGCAAGGCATCGAAAGAGGTTCGCGCCCTGGCTGATTACGTGTTCA
CGAAGATGGAGATTTCCCAATGACTGCGGCTCAAGCCAAGACCACCAGTC
GAGGCGTGGACTCAAGGCTCTCGCGAATGGCTCGCGTTGGAAACTTTCAT
TGAACTTGAGGGGCACCGCAGGGAAATTCTCGTCCTTGCGAGAACCGGC
TATGTCGTGCTGCGCATCGAGCCTGCGCCCTTGGCTTGTCTCGCCCCTCT
CCGCGTCGCTACGGGCTTCCAGCGCCTTTCCGACGCTCACCGGGCTGGT
TGCCCTCGCCGCTGGGCTGGCGGCCGTCTATGGCCCTGCAAACGCGCCAG
AAACGCCGTCGAAGCCGTGTGCGAGACACCGCGGCCGCCGGCGTTGTGGA
TACCACGCGGAAAACTTGGCCCTCACTGACAGATGAGGGGCGGACGTTGA
CACTTGAGGGGCCGACTCACCCGGCGCGGCGTTGACAGATGAGGGGCAGG
CTCGATTTCGGCCGGCGACGTGGAGCTGGCCAGCCTCGCAAATCGGCGAA
AACGCCTGATTTTACGCGAGTTTCCCACAGATGATGTGGACAAGCCTGGG
GATAAGTGCCCTGCGGTATTGACACTTGAGGGGCGCGACTACTGACAGAT
GAGGGGCGCGATCCTTGACACTTGAGGGGCAGAGTGATGACAGATGAGGG
GCGCACCTATTGACATTTGAGGGGCTGGGATCAAGCTTCGTGATGAGCTG
TCAGTCGAGCCGGGCGGGAATGGGTGACTAGCGCAGGCGCAGCCGGAGTC
TGTCAGCCATTCACGGCTGGCCGCCGCCGGCAGGCGACTTTGAGGCCCTA
ACAGCCAAGGCAAATGCAGCTGGGGTTAGGAGATCATAAGAACGATGACT
TGCCGACCCTTGAAATTCGCGGCCTGCAGGCTTGCACCTCGCTCACTGTA
TGCACGAACCCCCGATCATCATCCGTGAGCGACCGTCGCTCACAATCTAT
GAGCTATCCCTAGCTCATTATCCATGAGCTAGGTTAGGTCACCCCTATGAG
CTACCCCCCCTTCATGAGTTACCCCTAGCTCATATGTGAGAGATATCTCA
CAGGATTTGAGAGATAACGTGCACGGATGAGCTACCCATCGCTCACTAGA
TGAGCTAGGGTATGCGTGAACCATGAACGATATCTAACAAATATGCACGA
TATCGATCACGCAATTGCACCGTAGGAGGCCCAATGGCCAATGACAAAAA
CGAGATCCGCGCCTATGCGCAGCCTGCCCAGCGCGGTACATGGGTACAGA
CTGAGCGCGCCGGTCATGAGGCATGGCCGCACTGACTGCACAGGCACCC
CGCGCAGCACAGTTGATGCACATCCTGGTACAGCACATGGATAAGCAAGG
CGCGCTGATCATCAGCCAGGCCACGCTGGCCAAGCTGATGGAAACGTCCG
TGGCCACCACCAAACGCGCCATCGCCATCCTGACCAAGCACAACTGGATC
CAGACCATCAGTGTGGGTGGCCAACGGGGTGGCACGCTCGCTTATGTAGT
GAACAGCCGGATTGCATGGGCGGACAAGAGGGACAACCTTCAGTTTGCCC
TGTTCAACGCTCGGGTACTGGTTTCTACCGAGGATCAGGCTGATTTGGGC -continued

```
GATGCCAAGCTCAAGCAGCTGCCGACAATGGAAGACGGCGACATTCAGCT
ACCTGCGGGTCCAGGTATGGATCCGCCTGCGCAGGAGTCGCTGGAGGGAA
TGTTGCCTGATATGCCCTCTATTCCCCACGGTAACTGAGGCAAGGACCAA
GGAGGGTGCTTTATGTGGAAGATCGAATTCAGTAAGGATGACCACGGCAT
AGGTCAGTTCGGCGGCAGTGTACGAATGAATGATCCAGCACTGTGGCCGG
TTACGCCGGATACAAACGTTCCCCTCACGCCGCTCTGTACCTTGACCGAG
GCACTGTTGCCCGTCCGGTTCTTGCCACCTGGCATGGCCATGACCGTGTT
CATTGCGCCGAACCGGAAGGCCAACGGCTTCAACTTGTCGACGATCCGGG
ATTACCCTGTTATCCCTAGAGCTTGGCGTAATCATGGTCATAGCTGTTTC
CTGTGTGAAATTGTTATCCGCTCACAATTCCACACAACATACGAGCCGGA
AGCATAAAGTGTAAAGCCTGGGGTGCCTAATGAGTGAGCTAACTCACATT
AATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATT
GGGCGCTCTTCCGCTTCCTCGCTCACTGACTCGCTGCGCTCGGTCGTTCG
GCTGCGGCGAGCGGTATCAGCTCACTCAAAGGCGGTAATACGGTTATCCA
CAGAATCAGGGGATAACGCAGGAAAGAACATGTGAGCAAAAGGCCAGCAA
AAGGCCAGGAACCGTAAAAAGGCCGCGTTGCTGGCGTTTTTCCATAGGCT
CCGCCCCCCTGACGAGCATCACAAAAATCGACGCTCAAGTCAGAGGTGGC
GAAACCCGACAGGACTATAAAGATACCAGGCGTTTCCCCCTGGAAGCTCC
CTCGTGCGCTCTCCTGTTCCGACCCTGCCGCTTACCGGATACCTGTCCGC
CTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAA
CCCCCCGTTCAGCCCGACCGCTGCGCCTTATCCGGTAACTATCGTCTTGA
GTCCAACCCGGTAAGACACGACTTATCGCCACTGGCAGCAGCCACTGGTA
ACAGGATTAGCAGAGCGAGGTATGTAGGCGGTGCTACAGAGTTCTTGAAG
TGGTGGCCTAACTACGGCTACACTAGAAGGACAGTATTTGGTATCTGCGC
TCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTAC
GGGGTCTGACGCTCAGTGGAACGAAAACTCACGTTAAGGGATTTTGGTCA
TGAGATTATCAAAAAGGATCTTCACCTAGATCCTTTTAAATTAAAAATGA
AGTTTTAAATCAATCTAAAGTATATATGAGTAAACTTGGTCTGACAGTTA
CCAATGCTTAATCAGTGAGGCACCTATCTCAGCGATCTGTCTATTTCGTT
CATCCATAGTTGCCTGACTCCCCGTCGTGTAGATAACTACGATACGGGAG
GGCTTACCATCTGGCCCCAGTGCTGCAATGATACCGCGAGACCCACGCTC
ACCGGCTCCAGATTTATCAGCAATAAACCAGCCAGCCGGAAGGGCCGAGC
GCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGT
TGTTGCCATTGCTACAGGCATCGTGGTGTCACGCTCGTCGTTTGGTATGG
CTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAG
AAGTAAGTTGGCCGCAGTGTTATCACTCATGGTTATGGCAGCACTGCATA
ATTCTCTTACTGTCATGCCATCCGTAAGATGCTTTTCTGTGACTGGTGAG
TACTCAACCAAGTCATTCTGAGAATAGTGTATGCGGCGACCGAGTTGCTC
TTGCCCGGCGTCAATACGGGATAATACCGCGCCACATAGCAGAACTTTAA
AAGTGCTCATCATTGGAAAACGTTCTTCGGGGCGAAAACTCTCAAGGATC
TTACCGCTGTTGAGATCCAGTTCGATGTAACCCACTCGTGCACCCAACTG
ATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGA
ATACTCATACTCTTCCTTTTTCAATGGGGTGGGCGAAGAACTCCAGCATG
AGATCCCCGCGCTGGAGGATCATCCAGCCGGCGTCCCGGAAAACGATTCC
GAAGCCCAACCTTTCATAGAAGGCGGCGGTGGAATCGAAATCTCGTGATG
GCAGGTTGGGCGTCGCTTGGTCGGTCATTTCGAACCCCAGAGTCCCGCTC
AGAAGAACTCGTCAAGAAGGCGATAGAAGGCGATGCGCTGCGAATCGGGA
GCGGCGATACCGTAAAGCACGAGGAAGCGGTCAGCCCATTCGCCGCCAAG
CTCTTCAGCAATATCACGGGTAGCCAACGCTATGTCCTGATAGCGGTCCG
CCACACCCAGCCGGCCACAGTCGATGAATCCAGAAAAGCGGCCATTTTCC
ACCATGATATTCGGCAAGCAGGCATCGCCATGGGTCACGACGAGATCCTC
GCCGTCGGGCATGCGCGCCTTGAGCCTGGCGAACAGTTCGGCTGGCGCGA
GCCCCTGATGCTCTTCGTCCAGATCATCCTGATCGACAAGACCGGCTTCC
ATCCGAGTACGTGCTCGCTCGATGCGATGTTTCGCTTGGTGGTCGAATGG
GCAGGTAGCCGGATCAAGCGTATGCAGCCGCCGCATTGCATCAGCCATGA
TGGATACTTTCTCGGCAGGAGCAAGGTGAGATGACAGGAGATCCTGCCCC
GGCACTTCGCCCAATAGCAGCCAGTCCCTTCCCGCTTCAGTGACAACGTC
GAGCACAGCTGCGCAAGGAACGCCCGTCGTGGCCAGCCACGATAGCCGCG
CTGCCTCGTCCTGCAGTTCATTCAGGGCACCGGACAGGTCGGTCTTGACA
AAAAGAACCGGGCGCCCCTGCGCTGACAGCCGGAACACGGCGGCATCAGA
GCAGCCGATTGTCTGTTGTGCCCAGTCATAGCCGAATAGCCTCTCCACCC
AAGCGGCCGGAGAACCTGCGTGCAATCCATCTTGTTCAATCATGCGAAAC
GATCCTCATCCTGTCTCTTGATCAGATCTTGATCCCCTGCGCCATCAGAT
CCTTGGCGGCAAGAAAGCCATCCAGTTTACTTTGCAGGGCTTCCCAACCT
TACCAGAGGGCGCCCCAGCTGGCAATTCCGGTTCGCTTGCTGTCCATAAA
ACCGCCCAGTCTAGCTATCGCCATGTAAGCCCACTGCAAGCTACCTGCTT
TCTCTTTGCGCTTGCGTTTTCCCTTGTCCAGATAGCCCAGTAGCTGACAT
TCATCCGGGGTCAGCACCGTTTCTGCGGACTGGCTTTCTACGTGTTCCGC
TTCCTTTAGCAGCCCTTGCGCCCTGAGTGCTTGCGGCAGCGTGAAGCTAT
TATTGAAGCATTTATCAGGGTTATTGTCTCATGAGCGGATACATATTTGA
ATGTATTTAGAAAAATAAACAAATAGGGGTTCCGCGCACATTTCCCCGAA
AAGTGCCACCTGACGTCTAAGAAACCATTATTATCATGACATTAACCTAT
AAAAATAGGCGTATCACGAGGCGCCCTTTCGTC
```

Accordingly, in a fifth aspect, there is provided a recombinant vector pCURE12, substantially as illustrated in FIG. 6. Advantageously, pCURE12 may be used in the method according to the invention for curing plasmids from *Pseudomonas* spp, and most preferably, from *P. putida*.

As described in the Examples, the inventors have successfully demonstrated that each of the recombinant displacement plasmids, pCURE1, pCURE2, pCURE11, and pCURE12, may be introduced into a bacterial host cell, for example by either direct transformation (e.g. electroporation) or by conjugation (e.g. from S17-1). Furthermore, the inventors were surprised to find that each of these displacement plasmids could be used with high efficiency to displace or cure susceptible resident endogenous plasmids from 100% of host cells transformed with the recombinant displacement plasmid. Subsequent growth in the absence of any selection followed by plating on sucrose (for the sacB gene) allowed the isolation of many strains without either plasmid (i.e. the endogenous plasmid or the recombinant plasmid).

Hence, according to a sixth aspect, there is provided a cell containing a recombinant vector according to any of the second to fifth aspects.

Preferably, the cell is a prokaryote, and more preferably, a bacterial cell. It is preferred that the cell is a Gram-negative cell, which may be an Enterobacterium (e.g. *E. coli*) or *Pseudomonas* spp. (e.g. *P. putida*)

According to a seventh aspect of the invention, there is provided a kit comprising a recombinant vector according to any one of the second to fifth aspects, and at least one of (i) a vector, which is substantially identical to the recombinant vector but lacking sequences needed for displacement; (ii) a bacterial strain to allow conjugative transfer of the recombinant vector to the host of the plasmid to be displaced, and optionally, (iii) an instruction manual. Preferably, the kit comprises all of (i) to (iii).

It will be appreciated that the method, constructs and kit according to the invention may be put a variety of commercial uses to study any bacteria, which affect plants, animals and humans. Hence, the method, constructs and kit according to the invention may be used as an R&D tool, or for therapeutic uses, or in agriculture.

For example, in R&D, the method, constructs and kit according to the invention may be used in a further aspect of the invention to establish the specific virulence (such as attachment apparatus) or disease-causing (such as production of a toxin that acts on the host) properties conferred by plasmids. Furthermore, in another aspect, the method, constructs and kit according to the invention may be used to determine the resistance properties (such as resistance to antibiotics, to the immune system, or other host defences such as reactive chemical species produced in the phagosome) conferred by plasmids. For example, in a still further aspect, the method, constructs and kit according to the invention may be used to determine the sensitivity (such as to phage that may attach specifically to the pilus or other surface appendages or proteins encoded by the plasmid) conferred by plasmids. For example, in another aspect, the method, constructs and kit according to the invention may also be used to determine which antibiotics are most effective against plasmid-induced biofilms.

The plasmid curing technology disclosed herein provides for therapeutic applications by allowing the targeting of bacteria which have plasmids, which plasmids possess virulence determinants genes such as anti-biotic resistance and other virulence-related genes. As such, this technology can be administered to an individual, animal or other organism or body or surface to allow specific bacteria to be targeted by the displacement of specific plasmids which have associated virulence determinants genes, thereby allowing said bacteria to be killed or weakened or made more vulnerable to being targeted by other therapeutic agents. The data generated in the lab on the displacement of plasmids in live bacteria exemplifies its use as a therapeutic in the targeting of bacterial pathogens.

One example of a therapeutic use of the method, constructs and kit according to the invention envisaged by the inventors is to remove the pathogenic element of a bacterial infection but leave the commensal functions. In vivo delivery techniques may include any of:—(i) Phage therapy (for example, using bacterial viruses); (ii) naked DNA delivery as part of unit that contains uptake sequences for commonly transformable bacteria such as *Haemophilus*; and (iii) Donor bacterium that promotes conjugative transfer of resident DNA.

Alternatively, in another aspect of the invention, the method, constructs and kit according to the invention may be applied to development of probiotic strains that would be harmless in themselves and could be rendered immune to invasion by plasmids carrying virulence and resistance determinants. The inventors believe that if this were combined with the ability to donate an element that would cause the loss of plasmids from other bacteria, then this would also have commercial potential.

In agriculture, the method, constructs and kit according to the invention may be used in a further aspect of the invention in a method to develop crop protection products to remove pathogenic/parasitic actions by soil or plant based bacteria. E.g. Ti plasmids (tumour inducing) in *Agrobacterium*, reside in the soil and passes plasmid into the plant. This results in tumours/galls on the plant, which produce complex amino acids, which the bacteria can then use as a C and N source.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which:—

FIG. 1 shows a plasmid map of pO157 indicating the regions that are predicted to be responsible for replication and stable inheritance. The map shows how dispersed the two replicons and the two post-segregational killing systems are on the genome. Included in the map are a PpiI site (SEQ ID NO: 30) at nucleotide 72950, a PpiI site (SEQ ID NO:31) at nucleotide 72982; a PpiI site (SEQ ID NO: 32) at nucleotide 89454; and a PpiI site (SEQ ID NO: 33) at nucleotide 89486.

FIG. 2 shows a plasmid map of pAKE604. Only selected restriction sites used for the construction of the plasmid are shown, although additional sites recognised by these enzymes are also shown;

FIG. 3 shows plasmid maps of pCURE1. The plasmid map shown in part 1 of this figure is that of a plasmid having the nucleic acid sequence of SEQ ID No. 2. The plasmid map shown in part 2 of this figure is that of a plasmid having the nucleic acid sequence of SEQ ID No. 28. Only selected restriction sites used for the construction of the plasmid are shown, although additional sites recognised by these enzymes are also shown;

FIG. 4 shows plasmid maps of pCURE2. The plasmid map shown in part 1 of this figure is that of a plasmid having the nucleic acid sequence of SEQ ID No. 3. The plasmid map shown in part 2 of this figure is that of a plasmid having the nucleic acid sequence of SEQ ID No. 29. Only selected restriction sites used for the construction of the plasmid are shown, although additional sites recognised by these enzymes are also shown;

FIG. 5 shows a plasmid map of pCURE11. Only selected restriction sites used for the construction of the plasmid are shown, although additional sites recognised by these enzymes are also shown; and FIG. 6 shows a plasmid map of pCURE12. Only selected restriction sites used for the construction of the plasmid are shown, although additional sites recognised by these enzymes are also shown;

FIG. 7 is a gel demonstrating curing of pO157 by pCURE1. Starting from *E. coli* O157 either pAKE604 or pCURE1 was introduced by transformation. All transformants with pAKE604 retained the pO157 on the basis of plasmid profile, while all with pCURE1 had lost pO157;

FIG. 8 is a gel demonstrating the loss of pCURE1 by selection of sucrose resistant clones from derivatives of *E. coli* O157 from which pO157 had been displaced by the presence of pCURE1;

FIG. 9 is a gel demonstrating curing of IncP-1beta plasmid by pCURE11. Starting from a strain that carries just pRK24 either pAKE604 or pCURE11 were introduced by transformation. All transformants with pAKE604 retained the pRK24 on the basis of antibiotic resistance and plasmid profile, while all with pCURE11 had lost pRK24;

FIG. 10 is a gel demonstrating sucrose selection of bacteria that have lost pCURE11; and FIG. 11 is a gel demonstrating curing of IncP-1beta plasmid by pCURE11. Starting from a strain that carries just R751 either pAKE604 or pCURE11 were introduced by transformation. All transformants with pAKE604 retained the R751 on the basis of antibiotic resistance and plasmid profile, while all with pCURE11 had lost R751.

EXAMPLES

Outline of the Method of the Invention

The inventors set out to devise a new strategy for the efficient and stress-free displacement (curing) of endogenous plasmids from bacterial hosts. The method according to the invention has been designed to make it straightforward and non-stressful to displace any plasmid so long as its DNA sequence or other detailed genetic profile is available.

The method involves generating a series of recombinant displacement plasmid vectors that are inherently unstable in the host so that it is lost, albeit at low frequency, in the absence of selection. For application in *Escherichia coli*, the vector used is based on the pMB1 replicon. However, for use in other Gram-negative bacteria, a broad host range replicon (from the IncP-9 plasmid pM3) has been introduced allowing it to replicate in many other hosts. Selection for hosts harbouring the recombinant displacement vector is achieved by the presence of a gene conferring resistance to the antibiotic kanamycin, although other antibiotic selections could be used. The displacement plasmid also carries a gene called sacB that makes the host bacterial cell that carries it sensitive to sucrose if it is a Gram-negative bacterium (i.e. it is a counter-selective marker). Into the displacement plasmid, there are incorporated parts of the replication system of the endogenous parental plasmid that is to be displaced. Hence, the parts of the replication system in the displacement plasmid interfere with the parental plasmid, thereby displacing it from the host.

Many plasmids also carry gene sets that result in death of bacteria that have lost their endogenous plasmid. These work by encoding a toxin and an antidote produced by the endogenous plasmid. Hence, when the endogenous plasmid is lost, the antidote is degraded and the toxin remains and kills the bacterium. Hence, a unique feature of the method according to the invention involves incorporating the antidote gene into the recombinant displacement plasmid. Hence, the displacement vector consists of a combination of genes responsible for replication of the displacement plasmid in the host, and also genes encoding the regulatory parts of post-segregational killing systems (e.g. the antidote protein or antisense RNA) for displacing the endogenous plasmid, such that the host remains alive after displacement.

Once constructed, the recombinant displacement plasmid is introduced directly into a bacterial strain carrying the unwanted endogenous plasmid by transformation. Alternatively, the displacement plasmid is introduced into an *E. coli* strain S17-1. The displacement plasmid is then introduced into a bacterial strain carrying the unwanted endogenous plasmid by conjugative transfer from the *E. coli* strain S17-1 and selected on agar that does not support growth of the donor bacteria but also contains kanamycin to select for the transferred displacement plasmid. The resident endogenous plasmid is then displaced, and after purifying to single colonies on selective agar and growth in the absence of any selection at all, segregants that have also lost the displacement plasmid are selected because they can grow in the presence of sucrose (inability to grow on sucrose is indicative of the presence of the sacB gene on the displacement plasmid).

Summary of Displacement Plasmids Constructed

Plasmid pCURE1 (as shown in FIG. 3) consists of the following sequence segments: pAKE604 (7219 bp) cut at EcoRI (coordinate 3589 bp) and BamHI (coordinate 3628 bp) sites with the following inserts: flmC (coordinates 73732-73988), letA (coordinates 51692-52170), repFIB (coordinates 48289-49890) and RepFIIAcopAB (coordinates 2351-3053) from pO157 (AF074613).

Plasmid pCURE2 (as shown in FIG. 4) consists of pCURE1 with the following additional sequence segments: RepFICincC from F (AP001918, coordinates 49141-49476), reFIIAcopAB from pKDSC50 (NC_002638, coordinates 24300-25062), pemI from p1658/97 (AF550679, coordinates 40448-40857) and sok from p1658/97 (coordinates 124521-124270)

Plasmid pCURE11 (as shown in FIG. 5) consists of pAKE604 cut at EcoRI and BamHI sites with the following sequence inserts: parD (coordinates 35029-35395), korA/incC (coordinates 58936-59466) and oriV (coordinates 12366-12992) from RK2 (L27758).

Plasmid pCURE12 (as shown in FIG. 6) consists of pCURE11 with the following additional sequence segment: oriV-rep from pM3/pMT2 (AF078924, coordinates 2385-3694).

The first displacement plasmid produced, pCURE1, was designed to cure pO157 from its host *E. coli* O157. Plasmid pO157 was chosen because it contains replicons and PSK systems representative of other F incompatibility group plasmids (as shown in FIG. 1). It contains parts of the functional control regions of the two replicons (repFIIA and repFIB) from pO157. It also contains the control/antidote regions from the identified post-segregational killing systems from pO157 (sok of the hok/sok system and letA from the letAB system). Plasmid pCURE1 was shown to displace pO157 with 100% efficiency.

A derivative plasmid, pCURE2 (FIG. 4), was then created by incorporating into pCURE1 all additional replicons and psk systems identified from DNA sequences of F-like plasmids. These were: PSK systems—hok/sok from F, srnB/srnC from p1658/97 and pB171 (antisense RNA systems) and pemI/pemK from p1658/97 and pB171 (a toxin/anti-toxin system); replication systems—RepFIA from F/pHCM1 and RepFIIA from pKDSC50. The result was a plasmid (pCURE2) that is capable of displacing a wide range of F-like plasmids, and may be used against any plasmid suspected of being an F-like plasmid. It has been successfully tested against some selected F-like plasmids.

A further plasmid displacement constructed (pCURE11, shown in FIG. 5) was based on pCURE1, and which also contained segments from the IncP-1 regions oriV, parD and korA/incC. This plasmid (pCURE11) was used effectively to displace IncP-1 plasmids from E. coli. An IncP-9 replicon was introduced into pCURE11 to create pCURE12, thereby allowing it to replicate in Pseudomonas species. This has been shown to cause IncP-1 plasmid displacement from Pseudomonas species.

Materials and Methods
Bacterial Strain, Plasmids and Growth Conditions

For E. coli K12, the strains used were as follows: DH5α F⁻ endA1 hsdR17($r_K^- m_K^+$) supE44 thi-1 recA1 gyrA96 relA1 deoR Δ(lacZYA-argF)-U169 Φ80lacZΔM15 λ⁻phoA (5); S17-1, a strain with the IncP-1 alpha transfer genes integrated into the chromosome so that it will mobilise a plasmid containing $oriT_{RK2}$ (Bio-Technology. 1:784-791, 1983). E. coli O157:H7 Sakai strain stx- was derived by directed mutation of the toxin gene with an antibiotic resistance cassette. The specific strain used in these studies was derived in Japan in Professor Chihiro Sasakawa's laboratory as detailed below, using the Sakai strain of E. coli O157 (T Hayashi et al., DNA Research 8, 11-32, 2001).

The stx1- stx2- double-negative strain was constructed by first making an insertion of a blunted PstI fragment from the Km resistance gene into the SwaI site of the stxA2 gene (essentially the same method as used for construction of a nonpolar eae mutant previously described (Infection and immunity 68: 5943-5952, 2000). In addition, a 624 bp BsiWI (cgtacg) fragment from a part of stxA1 gene and the 5' flanking region was deleted. All results were confirmed by PCR in Japan and independently in the UK (Edinburgh, Dr David Smith). The non-toxigenic phenotype of the strain was confirmed in Japan using RPLA (reversed passive latex agglutination) with anti-Stx 1 or 2 antibody-conjugated latex beads (Denka Seiken, Tokyo, Japan). The mutant strain showed essentially the same characteristics of adherence to Caco-2 cells, growth rate in vitro, type III secretion and FAS test in comparison to its parent (i.e. shows the virulence factors expected of a enteropathogenic E. coli—see comments below). In addition, the non-toxigenic nature of the strain has been confirmed both by PCR and by the Vero cell assay by David Smith, at the University of Edinburgh.

For Pseudomonas putida, the strain used was KT2440 hsdR1, hsdM (Environmental Microbiology, 4:799-808, 2003).

Growth of all E. coli was at 37° C., while P. putida was grown at 30° C. The standard medium was LB, or Lagar (LB solidified with 1.5% w/v agar). Antibiotics used at standard concentrations were as follows: kanamycin, 50 μg/ml; penicillin 150 μg/ml (broth), or 300 μg/ml (agar); streptomycin, 30 μg/ml, 100 μg/ml chloramphenicol. In general, standard microbiological techniques were used for growth, transformation (by calcium chloride treatment) and manipulation of bacteria. (Sambrook, J., E. F. Fritsch, and T. Maniatis, 1989, Molecular Cloning: a Laboratory Manual, 2nd ed. Cold Spring Harbour Laboratory, New York.). Conjugative transfer was achieved using stationary phase cultures which were mixed in the ratio 1:10 (donor to recipient), filtered onto a sterile nylon membrane, placed on the surface of an L agar plate for at least 1 h and then resuspended in saline or LB before plating on selective L agar plates.

DNA Isolation, Manipulation and Sequencing

Crude, small-scale purification of plasmid DNA during plasmid construction work used the modified Birnboim and Doly preparation (Nucleic Acids Research, 7,1513-1523, 1979). PCR products for sequencing or further study were cloned using the Promega pGEM-T Easy vector system. Agarose gels were run in TAE (Sambrook, J., E. F. Fritsch, and T. Maniatis 1989. Molecular Cloning: A Laboratory Manual, 2nd ed. Cold Spring Harbour Laboratory, New York). DNA sequencing was carried out using the Big dye terminating kit manufactured by PE-ABI, which is based on chain termination method (Proceedings of the National Academy of Science USA. 74:4563-4567). This was used in accordance with the manufacturers guidelines.

The sequencing PCR cycling programme involved 25 cycles of denaturation at 96° C. for 30 sec, annealing at 50° C. for 15 sec and extension at 60° C. for 4 min. The ramping time was set to 1°/sec. The sequence reactions were run on an ABI 3700 DNA sequencer (Functional Genomics lab, University of Birmingham).

Polymerase Chain Reaction

PCR reactions were performed as described by Mullis, K., Faloona, F., Scharf, S., Saiki, R., Horn, G. and Erhlich, H., 1986. Specific enzymatic amplification of DNA in vitro: the polymerase chain reaction. Cold Spring Harbor Symposium of Quantitative Biology 51, 263-273. Primers were designed to flank the region of interest with extra restriction sites for cloning if needed. Primers were synthesised by Alta Bioscience, University of Birmingham. Table 1 below lists all primers designed and used in this study.

TABLE 1

Primers used in this work

| Sequence (all sequences are written 5'-3') | Coordinates | Plasmid template | Genetic region |
|---|---|---|---|
| ACATTAAACGAGAGTAATCCCC [SEQ ID No. 6] | 2351-2372 | pO157 (AF074613) | repFIIA copAB |
| GTCGACTGAAGATCAGTCACACCATCC [SEQ ID No. 7] | 3033-3053 | pO157 (AF074613) | repFIIA copAB |
| GCTGACAAGCTGTGGTCAGCAGAAC [SEQ ID No. 8] | 48289-48307 | pO157 (AF074613) | repFIB |
| TCTAGAGGAGGCTCGATCCAGTAAAC [SEQ ID No. 9] | 49890-49871 | pO157 (AF074613) | repFIB |

TABLE 1-continued

Primers used in this work

| Sequence (all sequences are written 5'-3') | Coordinates | Plasmid template | Genetic region |
|---|---|---|---|
| TCTAGACCATACGAAACGGGAATGC [SEQ ID No. 10] | 51692-51710 | pO157 (AF074613) | letA (ccdA) |
| AAGCTTACATCCACAAACAGACGATAAC [SEQ ID No. 11] | 52170-52149 | pO157 (AF074613) | letA (ccdA) |
| AAGCTTAGGAAAAGTGAATGTGGTCAG [SEQ ID No. 12] | 73,732-73,752 | pO157 (AF074613) | flmB (sok) |
| GAATTCCAACACACACCAGACAAGAG [SEQ ID No. 13] | 73,988-73,969 | pO157 (AF074613) | flmA (sok) |
| GGATCCGCCAGACGACTCATA [SEQ ID No. 14] | 49,141-49,157 | F (AP001918) | repFIA incC |
| CTCGAGCGGATAGCCAATTCAGA [SEQ ID No. 15] | 49,459-49,476 | F (AP001918) | repFIA incC |
| CTCGAGGGAACGGACTGGAAACA [SEQ ID No. 16] | 24,300-24,317 | pKDSC50 (NC_002638) | repFIIA copAB |
| GGATCCCGTGTCGGTAATGAGTGAA [SEQ ID No. 17] | 25,062-25,046 | pKDSC50 (NC_002638) | repFIIA copAB |
| GCTAGCACCACGCTGGGTTTACTG [SEQ ID No. 18] | 40,448-40,466 | p1658/97; pB171 (AF550679) | pemI |
| GGATCCAGCGAGACAAGCCAGATT [SEQ ID No. 19] | 40,857-40,840 | p1658/97; pB171 (AF550679) | pemI |
| CTGGTACCTCTCGCACAGCGATTTTC [SEQ ID No. 20] | 124,521-124,504 | p1658/97; pB171 (AF550679) | sok |
| TTGCTAGCCGCTTGAGGCTTTCTGC [SEQ ID No. 21] | 124,254-124,270 | p1658/97; pB171 (AF550679) | sok |
| GGATCCCAGCCCCTCAAATGTCAA [SEQ ID No. 22] | 12,366-12385 | RK2 (L27758) | oriV |
| CTCGAGGCGTGGACTCAAGGCTCT [SEQ ID No. 23] | 12,992-12973 | RK2 (L27758) | oriV |
| GTCGACTGGTGGTCTTGGCTTGAG [SEQ ID No. 24] | 58,236-58253 | RK2 (L27758) | korA-incC |
| AGATCTAAGGACGAGTTTTAGCGG [SEQ ID No. 25] | 59,466-59449 | RK2 (L27758) | korA-incC |
| GAATTCAGCGCATTTTCCCGAC [SEQ ID No. 26] | 35,029-35044 | RK2 (L27758) | parD |
| GGATCCCAGCCGTGAGGATGTAGG [SEQ ID No. 27] | 35,395-35377 | RK2 (L27758) | parD |

The DNA polymerases used were Expand High Fidelity system, manufactured by Boehringer Mannheim, for gene cloning and Taq polymerase for confirmation of chromosomal genotype. Glycerol was also added to the diagnostic PCR reactions to a final concentration of 5%. PCR product purification was achieved using a HIGH pure purification kit manufactured by Roche. Standard PCR conditions were as follows: denaturation at 94° C. for 4 min; 10 cycles of denaturation at 94° C. for 30 sec, annealing at 59° C. for 30 sec, annealing at 57° C. for 15 sec, extension at 72° C. for 1.2 min; 20 cycles of denaturation at 94° C. for 30 sec, annealing at 59° C. for 30 sec, annealing at 57° C. for 15 sec, extension at 72° C. for 1.2 min with an increment of 5 sec every cycle; final extension at 72° C. for 7 min.

General Design and Construction of the pCURE Plasmids

The method of the invention involves a plasmid vector that is inherently unstable so that it is lost, albeit at low frequency, in the absence of selection. For application in *Escherichia coli* the vector used, pAKE604 (Chemistry & Biology. 10:419-430, 2003), is based on the pMB1 replicon. Selection is achieved by the presence of a gene conferring resistance to the antibiotic kanamycin. The plasmid also carries the sacB gene, encoding levan sucrase that polymerises fructose from sucrose onto a sucrose starter unit in the periplasm, making the bacteria that carry it sensitive to sucrose so that plasmid-free segregants can be isolated easily. Into this vector are incorporated parts of the replication system of the plasmid to be displaced so that they will interfere with the parental plasmid.

Starting from a plasmid whose sequence is known, the inventors identified any genes annotated as putative replication functions on the basis of BLAST searches, as well as any with similarity to known PKS systems. By comparison with molecular genetics of related replication systems, the inventors ascertained whether any putative replication system is intact and what elements are likely either to repress expression of a vital component of the system (for example, a transcriptional repressor, an antisense RNA or other translational regulator), or a competitor for a vital step in the process (for example, a replication origin).

PCR primers were then designed to amplify one or more of these key elements so that the combination should have a very good chance of blocking replication of the endogenous plasmid. Similarly for the PKS systems identified in the endogenous plasmid, the inventors either identified the putative antidote protein in a proteic system or the region encoding the repressor antisense RNA. Again, primers were designed for amplification of the regions that will neutralise the killing effect of the putative PKS system. The primers were designed in such a way that the products have combinations of different restriction sites so that all the fragments can be cloned together without regenerating the restriction sites. This means that common sites can be used repeatedly allowing the same basic strategy for cloning can be used more than once For example, fragments with BamHI and BglII sites can be joined together due to the common sticky end (3'CTAG 5') generated by these enzymes, but neither site is regenerated after ligation ($G^V$GATCC and $A^V$GATCT go to GGATCT). This therefore creates multifunctional DNA tracts, which are relatively devoid of restriction sites.

The PCR products were then cloned into a vector such as pGEM-T Easy where the sequence was checked before joining the fragments together and insertion into pAKE604. The inventors chose the vector pAKE604 as the cloning vector in their experiments because it has a high copy number, which they believed would assist in the curing of lower copy number plasmids, and also ensure that the anti-sense RNA/antitoxins it expresses completely titrate (and therefore neutralise) any endogenous toxins. Furthermore, pAKE604 is unstable and confers a sucrose sensitivity phenotype on its host resulting from its sacB gene, allowing its counter-selection on sucrose nutrient agar (see section "Screen for sucrose sensitivity"). The vector pAKE604 also carries functional penicillin and kanamycin resistance genes allowing its selection. This bacteria with pAKE604 will grow on Lagar with kanamycin at 50 µg/ml and penicillin at 150 µg/ml.

Plasmids used or constructed during this work are described in Table 2 below.

TABLE 2

Previously described plasmids used in this work

| Plasmid name | Size | Selectable marker | Key properties | Reference and/or accession number |
|---|---|---|---|---|
| pAKE604 | 7219 bp | $Km^R$, $Ap^R$ | Suicide plasmid | El Sayed et al., 2001 |
| pGEM-TEasy | | | Vector for cloning PCR products | Promega |
| pO157 | 92,077 bp | None | F-like plasmid | Burland et al., 1998 |
| F | 99,159 bp | None | F plasmid | AP001918 |
| p1658/97 | 125,491 bp | $Su^R$, $EtBr^R$, $S^R$, $Tb^R$, $Gm^R$ | F-like plasmid | AF550679 |
| PKDSC50 | 49,503 bp | | F-like plasmid | Venkatesan et al., 2001 |
| RK2 | 60,099 bp | $Km^R$, $Tc^R$, $Ap^R$ | IncP-1α archetype | Pansegrau et al., 1994 |
| PRK24 | 65.2 kb | $Tc^R$, $Ap^R$ | IncP-1α Km sensitive | Meyer et al., 1977 |
| R751 | 53,339 bp | $Tp^R$ | IncP-1β archetype | Thorsted et al., 1998 |
| pCURE1 | 10,197 bp | $Km^R$, $Ap^R$ | pO157 displacement vcector | This work |
| pCURE2 | 12,002 bp | $Km^R$, $Ap^R$ | General IncF displacement vector | This work |
| pCURE11 | 9,419 bp | $Km^R$, $Ap^R$ | IncP displacement vector | This work |
| pCURE12 | 10,733 bp | $Km^R$, $Ap^R$ | Broad host range IncP displacement vector | This work |

References From Table 2

Burland, V., Shao, Y., Perna, N. T., Plunkett, G., Sofia, H. J. and Blattner, F. R., 1998. The complete DNA sequence and analysis of the large virulence plasmid of *Escherichia coli* O157:H7. Nucleic Acids Res. 26, 4196-4204.

El-Sayed, A. K., Hothersall, J. and Thomas, C. M., 2001. Quorum-sensing-dependent regulation of biosynthesis of the polyketide antibiotic mupirocin in *Pseudomonas fluorescens* NCIMB 10586. Microbiology-Sgm 147, 2127-2139.

Meyer, R., Figurski, D. and Helinski, D. R., 1977. Physical and genetic studies with restriction endonucleases on the broad host-range plasmid RK2. Mol. Gen. Genet. 152, 129-135.

Pansegrau, W., Lanka, E., Barth, P. T., Figurski, D. H., Guiney, D. G., Haas, D., Helinski, D. R., Schwab, H., Stanisich, V. A. and Thomas, C. M., 1994. Complete nucleotide sequence of Birmingham IncP-alpha plasmids—compilation and comparative analysis. J. Mol. Biol. 239, 623-663.

Thorsted, P. A., Macartney, D. P., Akhtar, P., Haines, A. S., Ali, N., Davidson, P., Stafford, T., Pocklington, M. J., Pansegrau, W., Wilkins, B. M., Lanka, E. and Thomas, C. N., 1998. Complete sequence of the IncP beta plasmid R751: implications for evolution and organisation of the IncP backbone. J. Mol. Biol. 282, 969-990.

Venkatesan, M. M., Goldberg, M. B., Rose, D. J., Grotbeck, E. J., Burland, V. and Blattner, F. R., 2001. Complete DNA sequence and analysis of the large virulence plasmid of *Shigella flexneri*. Infect. Immun. 69, 3271-3285.

Screen for Sucrose Sensitivity

It is vital that the functionality of the sacB gene is checked periodically, and especially before its use to select for bacteria that have lost the pCURE plasmids (after displacement of the endogenous plasmid). An overnight culture carrying the plasmid with sacB was grown under selection to ensure a high percentage of plasmid carriage. The culture was then serially diluted and spread on Lagar and Lagar+5% (w/v) sucrose. The plates were grown O/N at 37° C. or 30° C., after which time the number of colonies on each type of plate were counted. Typically this gave <0.1% sucrose resistant colonies indicating that essentially all the bacteria spread failed to survive.

Standard Plasmid Curing Experiment

The newly constructed recombinant displacement plasmid was introduced into a bacterial strain carrying the unwanted endogenous plasmid. This could be achieved by either transformation of competent bacteria using standard techniques, or by conjugative transfer from the E. coli strain S17-1. Transformants or transconjugants were selected for on agar that does not support growth of the donor bacteria (e.g. S17-1, if conjugation was used), but also contains kanamycin to select the transferred plasmid. Transformants or transconjugants were purified to single colonies on selective agar and then a selection of clones checked for the presence/absence of the resident endogenous plasmid on the basis of selectable markers carried by the plasmid, by screening for an endogenous plasmid band after extraction of plasmid DNA using standard techniques, or by PCR for a region encoded by the endogenous plasmid. Successful displacement was signified by a lack of the appropriate band.

Assuming efficient displacement of the endogenous plasmid, purified colonies were then check for their sensitivity to sucrose. A sucrose sensitive colony demonstrated that it still carried the recombinant displacement plasmid harbouring the functional sacB gene. The colony was grown in LB in the absence of any selection, and segregants that have also lost the displacement plasmid were positively selected for by growth on Lagar in the presence of sucrose. Sucrose resistant colonies were checked for the absence of the pCURE displacement plasmid.

Results (1) Design and Construction of pCURE1

The first displacement plasmid produced, pCURE1, was designed to cure pO157 from its host E. coli O157. Plasmid pO157 was chosen because of the interest to determine the effect of this plasmid on its host, but it served a useful test since it contains replicons and PSK systems representative of other F incompatibility group plasmids (Nucleic Acids Research. 26:4196-4204, 1998).

Referring to FIG. 1, there is shown a plasmid map of pO157 indicating the regions that are predicted to be responsible for replication and stable inheritance. This includes: the two replicons repFIIA and repFIB; the active partition locus sopABC; a multimer resolution system resD; and two post-segregational killing systems designated ccdAB (letAB) and parB (hok/sok). Plasmid pCURE1 was designed to contain parts of the functional control regions of the two replicons and the control/antidote regions from the identified post-segregational killing systems (sok of the hok/sok system and letA from the letAB system). For the FIIA replicon, the inventors chose to amplify the region encoding the antisense RNA, CopA, that indirectly blocks translation of the rep gene by directly blocking translation of short open reading frames whose translation is essential for rep translation due to translational coupling.

For the repFIB replicon, the inventors selected the combination of the rep gene and associated repeated sequences to which Rep binds (iterons) which both combine to give the control of replication since it is thought that inhibition occurs by "handcuffing" between Rep binding sites. For the repFIIA replicon, the copA locus was chosen since this encodes an antisense RNA that blocks translation of the rep gene. For the sok/flmB region just the antisense RNA region was chosen so as to prevent translation of the hok/flmA gene. For the let/ccd region the letA region encoding the antidote protein was chosen so as to prevent letB/ccdB from being translated. Primers were designed to amplify each of these loci and these are listed in Table 1. PCR was performed using these primers and the product cloned into pGEM-Teasy. The sequence of the cloned segment was checked and then sequentially joined together. In the case of the sok/flmB product sequencing showed that the primer incorporating the EcoRI site [SEQ ID No. 13] had been slightly truncated so EcoRI digestion created a fragment that included DNA as far as the EcoRI site flanking the insertion site in the pGEM-Teasy vector. The copA and the repFIB segment were released from the pGEM-T clones by BglII-SalI and SalI-XbaI digests respectively, mixed and then ligated with pAKE604 cut with BamHI and XbaI. The let and flmB/sok segments were released from the pGEM-T clones by XbaI-HindIII and HindIII-EcoRI digests respectively, mixed and then ligated with pAKE604 cut with XbaI and EcoRI. Transformants in DH5α were checked for the combined inserts by restriction analysis. The let-sok segment was then released by XbaI-EcoRI digestion and ligated with the pAKE604 derivative that already contained rep and cop, cut with XbaI and EcoRI. Transformants in DH5a were checked for the combined inserts by restriction analysis. The resulting plasmid was designated pCURE1, and is shown in FIG. 3.

Sucrose sensitivity conferred by pCURE1 was checked as described above after the plasmid had been transformed into E. coli DH5α cells, selecting resistance to kanamycin as described in Materials and Methods. A transformant colony was then grown with and without selection for pCURE1 by inoculating it into LB with or without 50 μg/ml Km. When transformants were grown with selection, the percentage of cells in the population that were sucrose resistant was 0.04% while in the absence of selection it was 0.13%, thereby suggesting loss of pCURE1 plasmid, and the sacB gene. This suggests that pCURE1 is a little unstable, being lost in the absence of selection so that more plasmid-free, and thus sucrose-resistant bacteria accumulate during growth in the absence of selection.

Loss of pCURE1 from colonies that grew on sucrose was then confirmed by streaking 12 colonies from sucrose plates onto Lagar+Km followed by LA without kanamycin. Cells only grew on Lagar plates. These results confirm that pCURE1 confers sucrose sensitivity, showing that the rate at which pCURE1 is lost is greater when there is no selection pressure for it, and that segregants that have lost pCURE1 can be selected with sucrose. Accordingly, the inventors concluded that sacB was a tight selectable marker.

(2) Validation of the Curing Capacity pCURE1

E. coli O157:H7 stx- (which harbours the endogenous plasmid pO157), was transformed with the displacement plasmid, pCURE1, under selection by kamamycin. The transformants were purified on Lagar with kanamycin and five clones tested for the presence of pO157 by isolation of DNA and gel electrophoresis. All five clones had lost the plasmid. A selection of pO157-negative transformants were then streaked onto a sucrose plate to identify sucrose-sensitive colonies—all clones had retained this phenotype. One clone was grown overnight in LB in the absence of selection and then a 0.1 ml aliquot spread on Lagar with sucrose. Sucrose-resistant colonies arose at approximately $10^{-3}$, and when DNA from these was analysed by standard plasmid isolation and gel electrophoresis the pO157 DNA was found to be no longer be visible. To check that the plasmid had not integrated into the chromosome PCR was performed to show that none of the pO157 sequences could be amplified. We therefore conclude that pO157 had been completely displaced.

Displacement of pO157 by pCURE1 was then shown in a further eleven transformants by visualising minipreps of E. coli O157:H7 stx-, [pCURE1], E. coli O157:H7 stx- and E. coli O157:H7 stx-[pAKE604] on a 0.8% gel (see FIG. 7). The gel clearly shows that the pO157 band was missing from pCURE1 transformants but not pAKE604 negative control transformants. Sucrose sensitivity was also confirmed in three transformants as before. In addition, twelve transformants that grew on sucrose were shown to have lost pCURE1 by minipreps (see FIG. 8). A further four pCURE1 constructs were transformed into E. coli DH5α. A transformant from each plate was then grown without selection for pCURE1 to establish rate of plasmid loss as before. The results were similar to those obtained before and confirmed pCURE1 confers sucrose sensitivity. The results are shown in Table 3.

TABLE 3

Demonstration of sucrose sensitivity of bacteria carrying pCURE1

| | Number of cells (cfu · ml$^{-1}$) | | | |
|---|---|---|---|---|
| | pCURE1clone 1 | pCURE1clone 2 | pCURE1clone 3 | pCURE1clone 4 |
| LA | $5.8 \times 10^8$ | $10.8 \times 10^8$ | $12.7 \times 10^8$ | $7.4 \times 10^8$ |
| LA + sucrose | $11 \times 10^5$ | $10 \times 10^5$ | $22 \times 10^5$ | $7 \times 10^5$ |
| % cells that lost pCURE1 | 0.19 | 0.09 | 0.17 | 0.09 |

(3) Construction of pCURE2

A derivative of pCURE 1 was then constructed, that may be used to cure a more diverse range of the F incompatibility group plasmids. This displacement plasmid was called pCURE2, which is shown in FIG. 6.

pCURE2 was designed by blasting the pO157 replicons and post-segregational killing systems (PSK) represented in pCURE1, which are repFIIA, repFIB, let toxin/anti-toxin system and flm anti-sense RNA system, DNA sequences against representative plasmids from each of the FI, FII, FI/II incompatibility groups. Replicons or PSK systems not present in pCURE1 or those that had identities less then 80% were cloned into pCURE1.

These were: PSK systems—hok/sok from F, srnB/snC from p1658/97 and pB171 (antisense RNA systems) and pemI/pemK from p1658/97 and pB171 (a toxin/anti-toxin system); replication systems—RepFIA from F/pHCM1 and RepFIIA from pKDSC50. These regions coupled to pAKE604 high copy number should be sufficient to switch the replicons off.

Primers were designed as listed in Table 1. The antisense RNAs sok and srnC were amplified by PCR from F and p1658/97 respectively and the pemI anti-toxin from p1658/97, and the products cloned into pGEM-Teasy. The incC region of F repFIA replicon contains five direct repeats that are the same consensus as those in the origin and consequently bind RepE, the replication initiator protein; it is involved in copy number control and confers incompatibility. The repFIIA replicon is regulated by repressor copB and antisense RNA copA. IncC and copA/copB regions were therefore amplified from F and pKDSC50 respectively using the primers listed in Table 1 and again cloned into pGEM-TEasy. Repeated attempts to amplify and clone sok of F were unsuccessful and must eventually be repeated. The resulting plasmids with the PCR products that were obtained were verified by restriction digest, and then sequencing of the insert. The pKDSC50 copAB plasmid was then cut with BamHI and NcoI both of which cut to one side of the insert and IncC from the repFIA replicon of F was inserted on a BamHI-NcoI fragment released from its pGEM-T derivative. The combined region was then excised on an XhoI fragment and inserted into the SalI site between the pO157 repFIIB cop and the repFIB segment in pCURE1, giving pCURE1A. In a similar way we attempted to amplify the chosen segments of the identified psk systems. This was successful for the pemI gene of p1658/97; pB171 and the sok gene of p1685/97 but not for the srnC gene of F. The PCR products were cloned into pGEM-Teasy and checked as above. The pGEM-Teasy plasmid with pemI was then cut with KpnI and PstI and sok was introduced on a KpnI-PstI fragment. The resulting plasmid with both genes was then cut with NheI, releasing a fragment with both genes which was then ligated into the XbaI site of pCURE1A, yielding pCURE2.

The result was a plasmid (pCURE2) as shown in FIG. 4, which should be capable of displacing a wide range of F-like plasmids. Its ability to cause displacement was tested against pKDSC50—the results demonstrated that all clones (8/8 tested) into which pCURE2 had been introduced lost the resident plasmid. Further testing is necessary to show whether it will cause displacement of essentially any new IncF-like plasmid.

(4) Design and Construction of pCURE 11

A third displacement plasmid called pCURE11 was constructed by amplifying the oriV region and parD, korA and incC genes from the IncP-1α plasmid RK2 using PCR and cloning them into pAKE604. Referring to FIG. 5, there is shown a plasmid map of pCURE11. oriV is the replication origin of the first IncP-1α replicon that was sequenced. The amplified region includes its nine iterons, which should be sufficient to titrate trfA replication initiator protein away from intergenic oriV and possibly block access to it by host proteins through handcuffing (Kittell, B. L. and Helinski, D. R., 1991. Iteron inhibition of Plasmid RK2 replication in vitro—evidence for intermolecular coupling of replication origins as a mechanism for RK2 replication control. Proc. Natl. Acad. Sci. U.S.A. 88, 1389-1393). ParD is an anti-toxin to a post-segregational killing system encoded by parE whose polypeptide product targets DNA gyrase (Jiang, Y., Pogliano, J., Helinski, D. R. and Konieczny, I., 2002. ParE toxin encoded by the broad-host-range plasmid RK2 is an inhibitor of *Escherichia coli* gyrase. Mol. Microbiol. 44, 971-979.) and autogenously regulates a two-gene operon. KorA and IncC are products of central control region (ccr) genes, with the KorA regulon including (and repressing) the trfA gene, which is essential for replication (Pansegrau, W., Lanka, E., Barth, P. T., Figurski, D. H., Guiney, D. G., Haas, D., Helinski, D. R., Schwab, H., Stanisich, V. A. and Thomas, C. M., 1994. Complete nucleotide sequence of Birmingham IncP-alpha plasmids—compilation and comparative analysis. J. Mol. Biol. 239, 623-663). These regions were amplified by PCR and cloned into pAKE604 as described herein.

(5) Validation of pCURE11 Curing Properties

The ability of pCURE11 to displace IncP-1α plasmids from their host was tested using RK2 (Ap$^R$, Tc$^R$, Km$^R$) derivative pRK24 (Ap$^R$, Tc$^R$, Km$^S$). pRK24 had been modified so that it is kanamycin sensitive (Meyer, R., Figurski, D. and Helinski, D. R., 1977. Physical and genetic studies with restriction endonucleases on the broad host-range plasmid RK2. Mol. Gen. Genet. 152, 129-135); this allows selection of pCURE11 (Km$^R$, Pn$^R$). Curing of pRK24 can be identified using its unique tetracycline resistance. Two pCURE11 constructs (pCURE11 clones 3 and 8) as well as pAKE604 were introduced into *E. coli* DH5α [RK24] by transformation, pAKE604 being used as a negative control in subsequent screening. Transformants were selected using kanamycin.

Twenty of both the pCURE11clone3 and 8 transformants, *E. coli* DH5α [RK24] [pCURE11] and five pAKE604 transformants were streaked onto a 5×5 grid on LA+0.1 μg/ml Tc+50 μg/ml Km plates. This tetracycline concentration was sufficient to induce tetracycline resistance but not to kill *E. coli* cells.

The transformants were then replica plated first onto LA+10 μg/ml Tc followed by Lagar+50 μg/ml Km. This tetracycline concentration was sufficient to select for pRK24. This was confirmed by parallel *E. coli* DH5α and *E. coli* DH5α [pRK24] control tests at both Tc concentrations. pAKE604 transformants grew on both Tc 10 μg/ml and Km plates, whereas pCURE11 transformants only grew on the Km plate. This indicates that pCURE11 transformants have lost pRK24, whereas those transformed with parent pAKE604 vector had not. pCURE11 IncP-1α curing ability was further verified by visualising the presence of the different plasmids on a gel. The gel showed that pCURE11 had displaced pRK24 from *E. coli* DH5a, where as pAKE604 parent vector had not (see FIG. 9).

Single colonies of *E. coli* DH5α [pRK24], that had been transformed with pCURE11 clone 3 and 8 were purified to single colonies on selective agar, tested for sucrose sensitivity and then grown without selection for pCURE11. The results showed that pCURE11 transformants do demonstrate sucrose sensitivity and the loss of pCURE11 was greater when transformants were grown without kanamycin selection. Confirmation that transformants that grew on sucrose had lost pCURE11 as opposed to having a mutant sacB gene, was determined by running plasmid profiles on eight colonies from the sucrose plates, along side the original *E. coli* DH5α [pRK24], pCURE11 transformants used in the stability test. The gel showed that while the original colonies contained pCURE11, the colonies that grew on sucrose had lost it (see FIG. 10).

TABLE 4

Demonstration of loss of pCURE11 in the absence of selection, on the basis of increase in the number of sucrose resistant bacteria

| plate and dilution | pCURE11 selection | | No pCURE11 selection | |
|---|---|---|---|---|
| | pCURE11.3 | pCURE11.8 | pCURE11.3 | pCURE11.8 |
| LA + 5% sucrose | | | | |
| $1 \times 10^{-4}$ | 49 | 75 | | |
| $1 \times 10^{-5}$ | 20 | 14 | 628 | 165 |
| original number of cells (cfu · ml−1) | $20 \times 10^{-6}$ | $14 \times 10^{-6}$ | $62.8 \times 10^{-7}$ | $16.5 \times 10^{-7}$ |
| LA | | | | |
| $1 \times 10^{-6}$ | 364 | 109 | 342 | 175 |
| original number of cells (cfu · ml−1) | $36.4 \times 10^{-8}$ | $10.9 \times 10^{-8}$ | $34.2 \times 10^{-8}$ | $17.5 \times 10^{-8}$ |
| % plasmid loss | 0.55 | 1.28 | 18 | 9.43 |

These results clearly demonstrate that pCURE11 can cure a IncP-1 plasmid from *E. coli* and that pCURE11 free segregants can then be selected for by growing transformants without selection and than plating cultures on sucrose.

(6) Screening of IncP-β Curing Activity

The ability of pCURE11 to cure IncP-β plasmids from their host was investigated using IncP-β plasmid R751 (trimethoprim resistant). pCURE11.3, pCURE11.8 and pAKE604 were transformed into *E. coli* NEM[R751] and selected for using Lagar+50 μg/ml Km plates. Twenty of both pCURE11 construct transformants and five pAKE604 transformants were then streaked onto a 5×5 grid on 100 μg/ml trimethoprim plates. Only the pAKE604 transformants grew, indicating that pCURE11 transformants had lost R751. Further confirmation that pCURE11 had cured R751 was obtained through screening the profile or small scale plasmid DNA extraction samples. The gel showed pCURE11 transformants had lost R751, whereas pAKE604 transformants had not (see FIG. 11).

(7) Construction of pCURE12

To demonstrate the use of this curing system in other Gram-negative bacteria, the oriV-rep region of IncP-9 plasmid pM3 was introduced into pCURE11, thereby creating pCURE12. This was done using the plasmid pACT1 (Sevastsyanovich, Y. R., Titok, M. A., Krasowiak, R., Bingle, L. E. H. and Thomas, C. M., 2005. Ability of IncP-9 plasmid pM3 to replicate in *E. coli* is dependent on both rep and par functions. Mol. Microbiol. 57, 819-833) which was cut with HindIII and SalI which released a 1309 bp fragment which was then ligated with a derivative of pCURE11 that had been modified by inserting a linker to introduce sites for these two enzymes.

Referring to FIG. 6, there is shown a plasmid map of pCURE12. The plasmid was transformed into *Pseudomonas* species (*P. putida*). This allowed the construct to replicate in *pseudomonas* species and consequently cure them of IncP plasmids.

Discussion

The inventors set out to test the effectiveness of curing plasmids that incorporate genetic regions, which neutralise the action of PSK systems encoded on the plasmid to be displaced. This key point is a surprising extrapolation of other curing vectors that have been reported by other groups both in terms of blocking replication of the resident plasmid using parts of replicon joined to an unstable plasmid carrying a sacB gene to allow selection of segregants. However, where this specific strategy was used, the purpose was to displace relatively simple repABC plasmid systems where the stable inheritance of the plasmid is driven by the combination of a replication and a segregational stability (active partitioning system) system apparently lacking a PKS system (Genes and Genetic Systems. 77:1-9, 2002).

While this is a widespread replicon type, there are many plasmids where this would be feasible and the inventors have targeted two such plasmid families. The results demonstrate that this approach can be 100% efficient and, from the apparent numbers of bacteria recovered at each stage, does not involve any loss of viability of the host bacteria due to the displacement at any stage. This significantly contrasts with the previously published attempt to displace pO157, which only used the incompatibility of a miniplasmid derived from pO157 and where success was very limited indeed, i.e. only 7 out of 41 colonies screened having lost the plasmid (Infection and Immunity, 69:6660-6669, 2001).

The inventors of the present invention believe that the principle described herein would work equally efficiently in any bacteria given a suitable vector. Given that the inventors were attempting to displace IncP-1 plasmids, they did not actually use the IncP-1 replicon as the basis for allowing the pAKE604 vector in species outside the Enterics. They used the IncP-9 replicon, which has a narrower host range and is unstable outside *Pseudomonas* species (Microbiology and Virology. 8:18-23, 1991), although this clearly has some advantages such as the fact that once it has been used to successfully displace the unwanted resident plasmid, it would be rapidly lost from the population. The inventors extended the range of plasmids available and included the IncP-1 replicon in one set. The inventors believe it will be interesting to take sequenced strains of Gram-negative bacteria for which little is known about their endogenous plasmids apart from their DNA sequence, and see to what extent one can predict enough information to design appropriate pCURE plasmids for effective curing of their endogenous plasmid. The inventors also plan to exploit Gram negative-Gram positive shuttle vectors to extend the principle outside of the Gram-negative bacteria. These will work in exactly the same way as described above, but will utilise a replicon that can function in Gram-positive bacteria to carry the segments that will interfere with replication of the unwanted resident plasmid as well as neutralising the effect of the psk systems on the unwanted plasmid.

The methods described herein depend on one having access to sequence information that allows one to predict what genetic loci will interfere with stable inheritance of the plasmid. This may limit the technology to strains of bacteria for which the DNA sequence is known. However, sequencing of new plasmids has revealed that many of them carry genes related to systems that are already known, and thus for which one can make very accurate predictions using bioinformatics. The available sequence information can be used to build an array that can be used to screen the DNA of any new plasmids after it has been fragmented and labelled to determine which known stable inheritance functions it carries. It could then be targeted by a pCURE plasmid "off the shelf" or a custom designed pCURE plasmid created.

The batteries of genetic loci that cause efficient exclusion of plasmids from chosen bacteria can be used in a variety of contexts, medical and agricultural. For example, in probiotic bacteria for use in an Intensive Therapy Unit, a suitable displacement plasmid could be used to prevent the acquisition of plasmids that might confer antibiotic resistance. Similarly, they might be used to prevent resistance to antibiotic resistance spreading in veterinary contexts. For these purposes, the inventors envisage the genes to be integrated into the chromosome so that the strain was effectively stable, rather than in an unstable plasmid. This would be achieved by inserting the essential rep and psk functions from the pCURE plasmids into the middle of a DNA segment from a non-essential part of the chromosome and then using this to allow the DNA to be recombined into the chromosome by homologous recombination.

Summary

In summary, the method according to the present invention provides a series of custom-built displacement plasmids, which may be introduced into a host cell, thereby causing the endogenous plasmid to be displaced from future generations. The resultant culture may then be purified to remove any cells containing the original plasmid. A sacB tag (which affords sucrose intolerance on the host cell) on the displacement plasmid is used to select for plasmid-free bacterial cells (because those with the sacB tag die). These plasmid-free cells may then be used to, for example, compare the characteristics of cells with and without the original plasmid. The recombinant displacement plasmid contains necessary sections of the original endogenous plasmid DNA, i.e. those regions that control replication and also post segregational killing (PSK).

The method according to the invention has been proven to work for *E. coli* O157, and is believed to work for related pathogenic strains with similar plasmids. It is preferred that the method is used for curing plasmids from Gram-negative bacteria. However, it is envisaged that the final products may be broad spectrum (i.e. designed to work for a range of species/strains) or species/strain specific.

The invention claimed is:

1. A method of displacing a plasmid comprising a post-segregational killing system from a host cell, the method comprising:
(a) introducing a recombinant nucleic acid molecule into a host cell harbouring a plasmid comprising a post-segregational killing (PSK) system or systems, and
(b) subjecting the host cell containing the recombinant nucleic acid molecule to conditions whereby competition or replication inhibition causes said plasmid to be displaced from the host cell,
wherein the recombinant nucleic acid molecule is adapted to neutralize toxic effects of the plasmid's post-segregational killing system or systems by encoding:
(i) a regulator protein, which is adapted to modulate expression of a toxin gene of the plasmid's PSK system into mRNA; or
(ii) an antisense RNA, which is adapted to bind to and prevent toxic action of any toxic mRNA; or
(iii) an antidote protein, which is adapted to bind to and prevent toxic action of a toxic protein; or
(iv) a DNA modification enzyme, which is adapted to prevent toxic action of any restriction endonuclease; or
(v) an immunity protein, which is adapted to prevent toxic action of any toxin protein; or
(vi) a combination thereof,
and wherein the nucleic acid molecule is also adapted to outcompete or inhibit replication of the plasmid, and
wherein the plasmid to be displaced is an F-like plasmid and the recombinant nucleic acid molecule comprises repFIIA, repFIB, sok and letA operatively linked together such that each gene is expressed in the host cell.

2. A method of displacing a plasmid comprising a post-segregational killing system from a host cell, the method comprising:
(a) introducing a recombinant nucleic acid molecule into a host cell harbouring a plasmid comprising a post-segregational killing (PSK) system or systems, and
(b) subjecting the host cell containing the recombinant nucleic acid molecule to conditions whereby competition or replication inhibition causes said plasmid to be displaced from the host cell,
wherein the recombinant nucleic acid molecule is adapted to neutralize toxic effects of the plasmid's post-segregational killing system or systems by encoding:
(i) a regulator protein, which is adapted to modulate expression of a toxin gene of the plasmid's PSK system into mRNA; or
(ii) an antisense RNA, which is adapted to bind to and prevent toxic action of any toxic mRNA; or
(iii) an antidote protein, which is adapted to bind to and prevent toxic action of a toxic protein; or
(iv) a DNA modification enzyme, which is adapted to prevent toxic action of any restriction endonuclease; or
(v) an immunity protein, which is adapted to prevent toxic action of any toxin protein; or
(vi) a combination thereof,
and wherein the nucleic acid molecule is also adapted to outcompete or inhibit replication of the plasmid, and
wherein the recombinant nucleic acid molecule comprises a plasmid selected from the group consisting of SEQ ID NO:2, SEQ ID NO:3, SEQ ID NO:4; SEQ ID NO:5, SEQ ID NO:28, and SEQ ID NO:29.

* * * * *